(12) United States Patent
Nebel et al.

(10) Patent No.: US 6,339,046 B1
(45) Date of Patent: *Jan. 15, 2002

(54) PYRAZDE HERBICIDES

(75) Inventors: Kurt Nebel, Hochwald (CH); Juraj Tuleja, Bratislava (SK); Georg Pissiotas, Lörrach (DE); Hans-Georg Brunner, Lausen (CH)

(73) Assignee: Syngenta Investment Corporation, Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/959,437

(22) Filed: Oct. 28, 1997

(30) Foreign Application Priority Data

Oct. 29, 1996 (CH) ................................................ 2668/96

(51) Int. Cl.[7] ........................ A01N 43/56; C07D 231/14

(52) U.S. Cl. .................................... 504/280; 548/375.1

(58) Field of Search ........................ 548/375.1; 504/280

(56) References Cited

U.S. PATENT DOCUMENTS

| 4,452,981 A | 6/1984 | Nagano et al. |
| 4,881,967 A | 11/1989 | Semple |
| 4,940,485 A | 7/1990 | Bohner et al. |

FOREIGN PATENT DOCUMENTS

| EP | 259265 | 3/1988 |
| EP | 361114 | 4/1990 |
| EP | 061741 | 10/1992 |
| EP | 561319 | 9/1993 |
| EP | 617033 | 9/1994 |
| EP | 796856 | 9/1997 |
| JP | 2300173 | 12/1990 |
| JP | 3072460 | 3/1991 |
| JP | 3093774 | 4/1991 |
| WO | 96/01254 | 1/1996 |
| WO | 97/00246 | 1/1997 |

OTHER PUBLICATIONS

Derwent Abstract No. 91–159355/22 (of JP–A–03 093 774), (1991).
Derwent Abstract No. 91–031992/05 (of JP–A–02 300 173), (1991).
Derwent Abstract No. 91–136056/19 (of JP–A–03 072 460), (1991).

(List continued on next page.)

Primary Examiner—Robert W. Ramsuer
(74) Attorney, Agent, or Firm—William A. Teoli, Jr.

(57) ABSTRACT

Compounds of the formula I

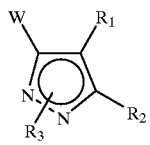
(I)

in which
$R_1$ is $C_1$–$C_4$alkyl;
$R_2$ is cyano or $NH_2C(S)$—;
$R_3$ is hydrogen, $C_1$–$C_4$alkyl, $C_1$–$C_4$haloalkyl, $C_3$- or $C_4$alkenyl, $C_3$- or $C_4$alkynyl, $C_3$–$C_8$haloalkenyl, NC—$CH_2$—, HOC(O)—$CH_2$— or $C_1$–$C_4$alkoxy-C(O)—$CH_2$—;
W is a group

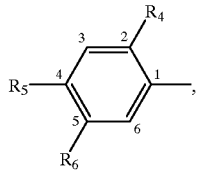
($W_1$)

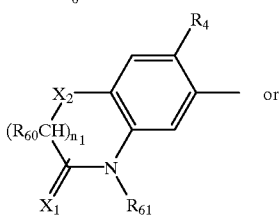

($W_2$)

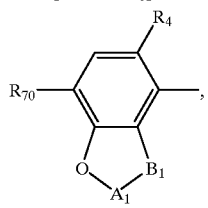

($W_3$)

and
$R_4$ to $R_6$, $R_{60}$, $R_{61}$, $R_{70}$, $X_1$, $X_2$, $n_1$ and $A_1$—$B_1$ are as defined in claim 1, and the pyrazole N-oxide, agronomically acceptable salts and stereomers of these compounds of the formula I, with the exclusion of the compound of the formula

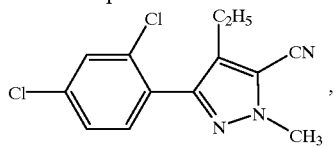

have good selective herbicidal properties when used pre- and post-emergence. The preparation of these compounds and their use as herbicidally active ingredients are described.

15 Claims, No Drawings

OTHER PUBLICATIONS

Comprehensive Organic Transformations, Editor R.C. Larock, VCH Publishers, Inc., New York, 1989, pp. 685–686.

Vogel's Textbook of Practical Organic Chemistry, Longman 1989, pages 938 et. seq., 1006 et. seq. and 1084 et. seq.

Advanced Organic Chemistry, Editor J. Mar., 3$^{rd}$ Edition, McGraw–Hill Book Company, New York, 1985, pages 816 et. seq. and 1057 et. seq.

Advanced Organic Chemistry, Editor J. Mar., 4$^{th}$ Edition, McGraw–Hill Book Company, New York, 1985, pages 932 et. seq.

Organikum, Editor J.A. Barth Leipzig, 1993, pp. 439–441 (Abstract enclosed).

Aust. J. Chem., 32, pp. 1727–1734, 1979.

J. Chem. Soc., Perkin Trans. II, pp. 382–394, 1974.

J. Heterocyclic Chem., 20, pp. 277–279, 1983.

J. Heterocyclic Chem., 19, pp. 1173–1177, 1982.

Khim. Geterotsikl. Soedin, pp. 914–917, 1990.

Ber. Deutsch. Chem. Ges., 26, pp. 2053–2059, 1893 (Abstract enclosed).

Chem. Ber. 99, pp. 1769–1770, 1966 (Abstract enclosed).

Arch. Pharm., 264, pp. 337–355, 1926 (Abstract enclosed).

Liebigs Annalen, 437, pp. 297–308, 1924 (Abstract enclosed).

Methodicum Chimicum, vol. 6, Georg Thieme Verlag, Stuttgart, 1974, pp. 768–773 (Abstract enclosed).

Methoden der Organischen Chemie (Methods of Organic Chemistry) (Houben–Weyl), vol. E5, Georg Thieme Verlag Stuttgart, pp. 1242–1245, 1985 (Abstract enclosed).

Methoden der Organischen Chemie (Mehods of Organic Chemistry) (Houben–Weyl), vol. E8b, Georg Thieme Verlag Stuttgart, pp. 399–405, 1994 (Abstract enclosed).

Pyrazoles, Pyrazolines, Pyrazolidines Indazoles and Condensed Rings, Editor R.H. Wiley, interscience Publishers, New York, page 1 et seq., 1967 (Title page)).

Comprehensive Heterocyclic Chemistry, Editors A.R. Katritzky and C.W. Rees, Pergamon Press, Oxford, 1987 (Title page).

Comprehensive Organic Functional Group Transformations, Editors A.R. Katritzky, O. Meth–Cohn, C.W. Rees, Pergamon Press, Oxford, 1995 (Title page).

Organic Reactions, vol. 18, pp. 1–97, 1970.

Organic Synthesis, 49, pp. 81–85, 1969.

J. Chem. Soc., pp. 1297–1302, 1954.

J. Organomet. Chem., 71, pp. 325–333, 1974.

J. Am. Chem. Soc., 54, pp. 2960–2964, 1932.

J. Am. Chem. Soc., 79, pp. 723–725, 1957.

Tetrahedron Letters No. 18, pp. 1585–1586, 1979.

J. Heterocyclic Chem., 21, pp. 1849–1856, 1984.

J. Am. Chem. Soc., 61, pp. 1940–1942, 1939.

J. Chem. Soc., Chem. Commun., pp. 1549–1550, 1995.

Liebigs Ann., 641, pp. 63–70, 1961 (Abstract enclosed).

J. Chem. Soc., pp. 491–501, 1943.

Synthesis, p. 287, 1989.

Org. Synth., Collect. vol. V, pp. 412–414, 1973.

J. Am. Chem. Soc., 93, pp. 746–752, 1971.

J. Org. Chem., 54, pp. 6096–6100, 1989.

J. Org. Chem., 39, pp. 3318–3331, 1974.

J. Org. Chem., vol. 40, No. 4, pp. 532–534, 1975.

Tetrahedron Lett., vol. 25, No. 21, pp. 2271–2274, 1984.

Tetrahedron Lett., vol; 27, No. 33, pp. 3931–3934, 1986.

Organic Reactions, 27, pp. 345–390, 1982.

Organic Reactions, 11, pp. 189–260, 1960.

Sulfonation and Related Reactions, Editor Gilbert, Interscience Publishers, New York, 1965 (Title page and table of contents).

Heterocycles, vol. 29, No. 8, pp. 1595–1600, 1989.

PYRAZDE HERBICIDES

The present invention relates to novel herbicidally active substituted pyrazole derivatives, to processes for their preparation, to compositions comprising these compounds, and to their use for controlling weeds, in particular in crops of useful plants, for example cereals, maize, rice, cotton, soya, oilseed rape, sorghum, sugar cane, sugar beet, sunflowers, vegetables and fodder plants, or for inhibiting the growth of plants.

Herbicidally active pyrozole compounds have been disclosed and are described, for example, in JP-A-03 093 774, JP-A-02 300 173, JP-A-03 072 460, EP-A-0 361 114 and WO 96/01254.

There have now been found novel substituted pyrazole derivatives which have herbicidal and growth-inhibiting properties.

The present invention thus relates to compounds of the formula I

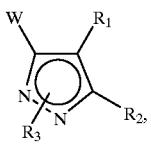

(I)

in which
$R_1$ is $C_1$–$C_4$alkyl;
$R_2$ is cyano or $NH_2C(S)$—;
$R_3$ is hydrogen, $C_1$–$C_4$alkyl, $C_1$–$C_4$haloalkyl, $C_3$- or $C_4$alkenyl, $C_3$- or $C_4$alkynyl, $C_3$–$C_8$haloalkenyl, NC—$CH_2$—, HOC(O)—$CH_2$- or $C_1$–$C_4$alkoxy-C(O)—$CH_2$—;
W is a group

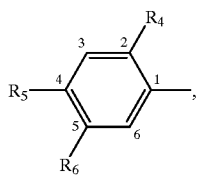

(W₁)

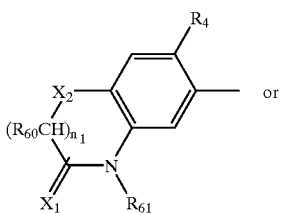

(W₂)

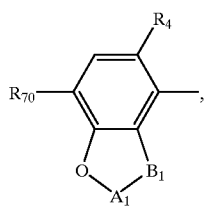

(W₃)

$R_4$ is hydrogen, fluorine, chlorine, bromine or methyl;
$R_5$ is hydrogen, halogen, methyl, ethyl, cyano, trifluoromethyl, nitro, amino, hydroxy, $C_1$–$C_4$haloalkoxy, HOC(O)—$C_1$–$C_4$alkoxy, CIC(O)—$C_1$–$C_4$alkoxy, $C_1$–$C_4$alkoxycarbonyl-$C_1$–$C_4$alkoxy, mercapto, $C_1$–$C_4$alkylthio, HOC(O)—$C_1$–$C_4$alkylthio, $C_1$–$C_4$alkoxycarbonyl-$C_1$–$C_4$alkylthio, benzyloxy or benzyloxy which is mono- to trisubstituted by halogen, $C_1$–$C_4$alkyl or $C_1$–$C_4$haloalkyl;
$R_6$ is hydrogen, halogen, cyano, nitro, amino, $CIS(O)_2$—, $R_{10}NH$ or $R_{10}R_{11}N$;
$R_{10}$ and $R_{11}$ independently of one another are $C_1$–$C_8$alkyl, $C_3$–$C_8$alkenyl, $C_3$–$C_8$alkynyl, $C_3$–$C_6$cycloalkyl, $C_1$–$C_8$haloalkyl, $C_3$–$C_8$haloalkenyl, $C_1$–$C_4$alkylcarbonyl, $C_1$–$C_4$haloalkylcarbonyl, $C_1$–$C_4$alkylsulfonyl, $C_1$–$C_4$haloalkylsulfonyl, benzoyl, benzoyl which is mono- to trisubstituted by $C_1$–$C_4$alkyl, $C_1$–$C_4$haloalkyl or halogen, or are benzyl or benzyl which is mono- to trisubstituted by $C_1$–$C_4$alkyl, $C_1$–$C_4$haloalkyl or halogen; or
$R_6$ is —$OR_{20}$;
$R_{20}$ is hydrogen, $C_1$–$C_8$alkyl, $C_3$–$C_8$alkenyl, $C_3$–$C_8$alkynyl, $C_1$–$C_8$haloalkyl,

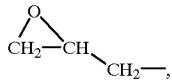

$C_3$–$C_8$haloalkenyl, $C_3$–$C_6$cycloalkyl,

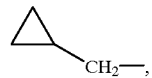

$C_1$–$C_4$alkoxy-$C_1$–$C_4$alkyl, $C_1$–$C_4$alkenyloxy-$C_1$–$C_4$alkyl, $C_1$–$C_4$alkylamino-$C_1$–$C_4$alkyl, di-$C_1$–$C_4$alkylamino-$C_1$–$C_4$alkyl, $C_1$–$C_4$alkoxy-$C_1$–$C_4$alkoxy-$C_1$–$C_4$alkyl, $C_1$–$C_4$alkylthio-$C_1$–$C_4$alkyl, $C_1$–$C_4$alkyl-C(O)—$C_1$–$C_8$alkyl,

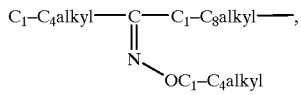

$C_1$–$C_4$alkyl-C(O—$C_1$–$C_4$alkyl)$_2$-$C_1$–$C_8$alkyl,

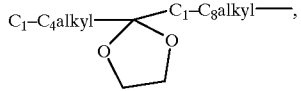

phenyl, benzyl, pyridyl, pyrimidinyl, pyrazinyl or pyridazinyl, it being possible for these abovementioned aromatic and heteroaromatic rings to be mono- to trisubstituted by $C_1$–$C_4$alkyl, $C_1$–$C_4$haloalkyl or halogen; or
$R_{20}$ is $R_{21}XC(O)$—$C_1$–$C_8$alkyl or

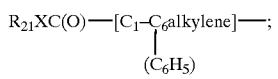

X is oxygen, sulfur, or $R_{22}N$;
$R_{21}$ is hydrogen, $C_1$–$C_8$alkyl, $C_3$–$C_8$alkenyl, $C_3$–$C_8$alkynyl, $C_1$–$C_8$haloalkyl, $C_3$–$C_6$cycloalkyl, $C_1$–$C_4$alkoxy-$C_1$–$C_4$alkyl, $C_1$–$C_4$alkylthio-$C_1$–$C_4$alkyl, phenyl, phenyl which is mono- to trisubstituted by $C_1$–$C_4$alkyl, $C_1$–$C_4$haloalkyl or halogen, or is benzyl or benzyl which is mono- to trisubstituted by $C_1$–$C_4$alkyl or halogen; and $R_{22}$ is hydrogen, $C_1$–$C_8$alkyl or $C_3$–$C_8$alkenyl, or $R_6$ is —$S(O)_m R_{30}$;

m is 0, 1 or 2;

$R_{30}$ is hydrogen, $C_1$–$C_8$alkyl, $C_3$–$C_8$alkenyl, $C_3$–$C_8$alkynyl, $C_1$–$C_8$haloalkyl, $C_3$–$C_8$haloalkenyl, $C_3$–$C_6$cycloalkyl, $C_1$–$C_4$alkoxy-$C_1$–$C_4$alkyl, $C_1$–$C_4$alkylthio-$C_1$–$C_4$alkyl, $C_1$–$C_4$alkylC(O)—$C_1$–$C_8$alkyl, phenyl, phenyl which is mono- to trisubstituted by $C_1$–$C_4$alkyl, $C_1$–$C_4$haloalkyl or halogen, benzyl, benzyl which is mono- to trisubstituted by $C_1$–$C_4$alkyl, $C_1$–$C_4$haloalkyl or halogen, or $R_{31}VC(O)$—$C_1$–$C_4$alkyl;

V is oxygen, sulfur or $R_{32}N$;

$R_{31}$ is hydrogen, $C_1$–$C_8$alkyl, $C_3$–$C_8$alkenyl, $C_3$–$C_8$alkynyl, $C_1$–$C_8$haloalkyl, $C_3$–$C_6$cycloalkyl, $C_1$–$C_4$alkoxy-$C_1$–$C_4$alkyl, $C_1$–$C_4$alkylthio-$C_1$–$C_4$alkyl, phenyl, phenyl which is mono- to trisubstituted by $C_1$–$C_4$alkyl, $C_1$–$C_4$haloalkyl or halogen, or is benzyl, or benzyl which is mono- to trisubstituted by $C_1$–$C_4$alkyl, $C_1$–$C_4$haloalkyl or halogen;

$R_{32}$ is hydrogen, $C_1$–$C_8$alkyl or $C_3$–$C_8$alkenyl; or

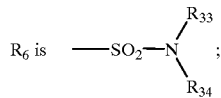

$R_{33}$ is hydrogen, $C_1$–$C_8$alkyl, $C_3$–$C_8$alkenyl or $C_3$–$C_8$alkynyl;

$R_{34}$ is hydrogen, $C_1$–$C_8$alkyl, $C_3$–$C_8$alkenyl, $C_3$–$C_8$alkynyl or $C_1$–$C_4$alkylcarbonyl; or $R_6$ is —$COR_{40}$;

$R_{40}$ is hydrogen, chlorine, $C_1$–$C_8$alkyl, $C_2$–$C_8$alkenyl, $C_2$–$C_8$alkynyl, $C_1$–$C_8$haloalkyl, $C_2$–$C_8$haloalkenyl, $C_3$–$C_6$cycloalkyl, $C_1$–$C_4$alkoxy-$C_1$–$C_4$alkyl, $C_1$–$C_4$alkylthio-$C_1$–$C_4$alkyl, phenyl, phenyl which is mono- to trisubstituted by $C_1$–$C_4$alkyl, $C_1$–$C_4$haloalkyl or halogen, or is benzyl or benzyl which is mono- to trisubstituted by $C_1$–$C_4$alkyl, $C_1$–$C_4$haloalkyl or halogen; or $R_6$ is —$COYR_{50}$;

Y is oxygen, sulfur, $R_{51}N$ or $R_{54}ON$;

$R_{50}$ is hydrogen, $C_1$–$C_8$alkyl, $C_3$–$C_8$alkenyl, $C_3$–$C_8$alkynyl, $C_1$–$C_8$haloalkyl,

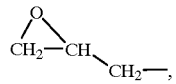

$C_3$–$C_8$haloalkenyl, cyano-$C_1$–$C_4$alkyl, $C_3$–$C_6$cycloalkyl,

$C_1$–$C_4$alkoxy-$C_1$–$C_4$alkyl, $C_1$–$C_4$alkylthio-$C_1$–$C_4$alkyl, phenyl,
phenyl which is mono- to trisubstituted by $C_1$–$C_4$alkyl, $C_1$–$C_4$haloalkyl or halogen, benzyl, benzyl which is mono- to trisubstituted by $C_1$–$C_4$alkyl, $C_1$–$C_4$haloalkyl or halogen, or is $C_1$–$C_8$alkylcarbonyl-$C_1$–$C_4$alkyl, $R_{52}ZC(O)$—$C_1$–$C_6$alkyl or $R_{52}ZC(O)$—$C_3$–$C_6$cycloalkyl;

Z is oxygen, sulfur, $R_{53}N$ or $R_{55}ON$;

$R_{52}$ is hydrogen, $C_1$–$C_8$alkyl, $C_3$–$C_8$alkenyl, $C_3$–$C_8$alkynyl, $C_1$–$C_8$haloalkyl,

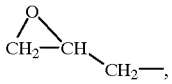

$C_3$–$C_8$haloalkenyl, $C_3$–$C_6$cycloalkyl,

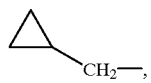

$C_1$–$C_4$alkoxy-$C_1$–$C_4$alkyl, $C_1$–$C_4$alkoxy-$C_1$–$C_4$alkoxy-$C_1$–$C_4$alkyl, $C_1$–$C_4$alkylthio-$C_1$–$C_4$alkyl, phenyl, phenyl which is mono- to trisubstituted by $C_1$–$C_4$alkyl, $C_1$–$C_4$haloalkyl or halogen, or is benzyl or benzyl which is mono- to trisubstituted by $C_1$–$C_4$alkyl, $C_1$–$C_4$haloalkyl or halogen;

$R_{51}$ and $R_{53}$ independently of one another are $C_1$–$C_8$alkyl, $C_3$–$C_8$alkenyl, $C_3$–$C_8$alkynyl, $C_1$–$C_8$haloalkyl, $C_1$–$C_4$alkylcarbonyl, $C_1$–$C_4$haloalkylcarbonyl, $C_1$–$C_4$alkylsulfonyl, $C_1$–$C_4$haloalkylsulfonyl, benzoyl, benzoyl which is mono- to trisubstituted by $C_1$–$C_4$alkyl, $C_1$–$C_4$haloalkyl or halogen, or are benzyl or benzyl which is mono- to trisubstituted by $C_1$–$C_4$alkyl, $C_1$–$C_4$haloalkyl or halogen;

$R_{54}$ and $R_{55}$ independently of one another are $C_1$–$C_4$alkyl; or $R_6$ is B—$C_1$–$C_8$alkyl, B—$C_1$–$C_8$haloalkyl, B—$C_2$–$C_8$alkenyl, B—$C_2$–$C_8$alkynyl, B—$C_2$–$C_8$haloalkenyl, B—$C_1$–$C_4$alkoxy-$C_1$–$C_4$alkyl or B—$C_1$–$C_4$alkylthio-$C_1$–$C_4$alkyl; and B is hydrogen, $R_{52}ZC(O)$—, cyano or $C_1$–$C_4$alkylcarbonyl;

$X_1$ and $X_2$ independently of one another are oxygen or sulfur;

$R_{60}$ is hydrogen or $C_1$–$C_4$alkyl;

$R_{61}$ is hydrogen, $C_1$–$C_6$alkyl, $C_3$–$C_6$cycloalkyl, $C_3$–$C_6$alkenyl, $C_3$–$C_6$alkynyl, benzyl, benzyl substituted by halogen, $C_1$–$C_6$haloalkyl, $C_3$–$C_6$haloalkenyl, $C_1$–$C_4$alkyl-C(O)—$C_1$–$C_4$alkyl, $C_1$–$C_4$alkoxy-$C_1$–$C_4$alkyl, $C_1$–$C_4$alkoxy-$C_1$–$C_4$alkoxy-$C_1$–$C_4$alkyl, HOC(O)—$C_1$–$C_6$alkyl, ClC(O)—$C_1$–$C_6$alkyl, $C_1$–$C_6$alkoxycarbonyl-$C_1$–$C_6$alkyl, $C_1$–$C_6$haloalkoxycarbonyl-$C_1$–$C_6$alkyl, $C_3$–$C_6$alkenyloxycarbonyl-$C_1$–$C_6$alkyl, $C_3$–$C_6$alkynyloxycarbonyl-$C_1$–$C_6$alkyl, $C_1$–$C_6$alkylthio-C(O)—$C_1$–$C_6$alkyl, $C_3$–$C_6$alkenylthio-C(O)—$C_1$–$C_6$alkyl, $C_3$–$C_6$alkynylthio-C(O)—$C_1$–$C_6$alkyl, $C_1$–$C_6$haloalkylthio-C(O)—$C_1$–$C_6$alkyl, $R_{62}R_{63}NC(O)—C_1–C_6alkyl$,

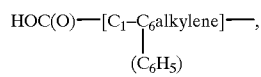

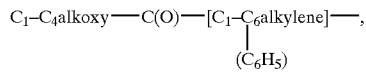

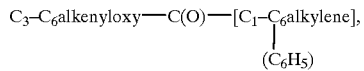

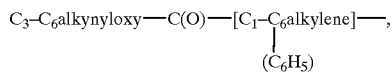

$C_1–C_4alkoxycarbonyl$, $C_3–C_6alkenyloxycarbonyl$, $C_3–C_6alkynyloxycarbonyl$, oxetanyloxycarbonyl, $HOC(O)—C_3–C_6cycloalkyl$, $C_1–C_4alkoxycarbonyl-C_3–C_6cycloalkyl$, $C_3–C_6alkenyloxycarbonyl-C_3–C_6cycloalkyl$, $C_3–C_6alkynyloxycarbonyl-C_3–C_6cycloalkyl$, $C_1–C_6alkylthio-C_1–C_6alkyl$, $C_3–C_6alkenylthio-C(O)—C_3–C_6cycloalkyl$ or $CIC(O)—C_3–C_6cycloalkyl$;

$R_{62}$ is hydrogen, $C_1–C_6alkyl$, $C_3–C_6alkenyl$, $C_3–C_6alkynyl$, $C_1–C_6haloalkyl$, benzyl, phenyl, or phenyl which is mono- to trisubstituted by halogen, $C_1–C_4alkyl$ or $C_1–C_4haloalkyl$;

$R_{63}$ has the meaning of $R_{62}$, or is $C_3–C_6cycloalkyl$, $C_3–C_6halocycloalkyl$, phenyl or phenyl which is mono- to trisubstituted by halogen, $C_1–C_4alkyl$ or $C_1–C_4haloalkyl$;

$n_1$ is 0, 1, 2, 3 or 4;

$R_{70}$ is hydrogen, halogen, trifluoromethyl, cyano, nitro, amino or $C_1–C_4haloalkoxy$;

$A_1—B_1$ is a group

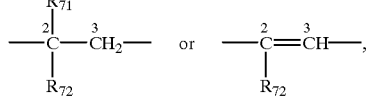

the carbon atom 2 being bonded to the oxygen atom;

$R_{71}$ is hydrogen or $C_1–C_6alkyl$;

$R_{72}$ is hydrogen, cyano, $C_1–C_6alkyl$, $C_1–C_6haloalkyl$, $cyano-C_1–C_4alkyl$, $hydroxy-C_1–C_6alkyl$, $C_1–C_6alkoxy-C_1–C_6alkyl$, $C_3–C_6alkenyloxy-C_1–C_4alkyl$, $C_3–C_6alkynyloxy-C_1–C_4alkyl$, $C_1–C_6alkylcarbonyloxy-C_1–C_6alkyl$, $C_1–C_6alkoxycarbonyl-C_1–C_6alkyl$, $HOC(O)—C_1–C_6alkyl$, $CIC(O)—C_1–C_6alkyl$, carboxyl, $CIC(O)—C_1–C_6alkoxycarbonyl$, $C_1–C_6haloalkoxycarbonyl$, $C_3–C_6alkenyloxycarbonyl$, $C_3–C_6alkynyloxycarbonyl$, $C_3–C_6cycloalkoxycarbonyl$, $C_1–C_6alkoxy-C_1–C_6alkoxycarbonyl$, benzyloxycarbonyl, benzyloxycarbonyl which is mono- to trisubstituted by halogen, or is $C_1–C_4alkoxycarbonyl$, $HOC(S)—$, $C_1–C_6alkylthio-C(O)—$, $C_1–C_6haloalkylthio-C(O)—$, $C_3–C_6alkenylthio-C(O)—$, $C_3–C_6alkynylthio-C(O)—$, $benzylthio-C(O)—$, benzyl, benzyl which is mono- to trisubstituted by halogen, or is $R_{73}R_{74}NC(O)—$, phenoxycarbonyl or $phenyl-C_1–C_6alkyl$, it being possible for the phenyl ring to be substituted by halogen, $C_1–C_4alkyl$ or $C_1–C_4haloalkyl$, or is $NH_2C(S)—$ or $OHC—$;

$R_{73}$ is hydrogen, $C_1–C_6alkyl$, $C_3–C_6alkenyl$, $C_3–C_6alkynyl$, benzyl, benzyl which is mono- to trisubstituted by halogen, $C_1–C_4alkyl$ or $C_1–C_4haloalkyl$, or is $C_1–C_6haloalkyl$; and $R_{74}$ has the meaning of $R_{73}$, or is phenyl or phenyl which is mono- to trisubstituted by halogen, $C_1–C_4alkyl$ or $C_1–C_4haloalkyl$, and the pyrazole N-oxides, agronomically acceptable salts and stereoisomers of these compounds of the formula I, with the exclusion of the compound of the formula

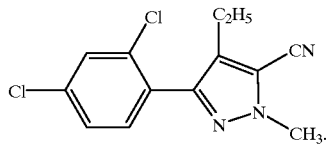

In the definitions mentioned above, halogen is to be understood as meaning iodine, and preferably fluorine, chlorine and bromine.

The alkyl, alkenyl and alkynyl groups in the definitions of the substitutents can be straight-chain or branched, and this also applies to the alkyl, alkenyl and alkynyl moiety of the alkylcarbonyl, hydroxyalkyl, cyanoalkyl, alkoxyalkyl, alkoxyalkoxyalkyl, alkylthio, alkylthio-C(O), alkenylthio-C(O), alkynylthio-C(O), alkylsulfonyl, alkylaminoalkyl, dialkylaminoalkyl, alkylcarbonylalkyl, $B—C_1–C_8alkyl$, $B—C_2–C_8alkenyl$, $B—C_2–C_8alkynyl$, $HOC(O)—C_1–C_6alkyl$, $CIC(O)—C_1–C_6alkyl$, $phenyl-C_1–C_6alkyl$, alkylcarbonyloxyalkyl, $R_{21}XC(O)—C_1–C_8alkyl$, $R_{31}VC(O)—C_1–C_4alkyl$, $R_{52}ZC(O)—C_1–C_6alkyl$ and $R_{62}R_{63}N—C(O)—C_1–C_6alkyl$ groups.

Alkyl groups are, for example, methyl, ethyl, n-propyl, iso-propyl, n-butyl, sec-butyl, iso-butyl, tert-butyl and the various isomeric pentyl, hexyl, heptyl and octyl radicals. Methyl, ethyl, n-propyl, iso-propyl and n-butyl are preferred. For example, $R_1$ is n-propyl, iso-propyl, n-butyl, sec-butyl, iso-butyl, tert-butyl, preferably methyl and ethyl, and especially preferably methyl.

Examples of alkenyls which may be mentioned are vinyl, allyl, methallyl, 1-methylvinyl, but-2-en-1-yl, pentenyl, 2-hexenyl, 3-heptenyl and 4-octenyl, preferably alkenyl radicals having a chain length of 3 to 5 carbon atoms.

Examples of alkynyls which may be mentioned are ethynyl, propargyl, 1-methylpropargyl, 3-butynyl, but-2-yn-1-yl, 2-methylbutyn-2-yl, but-3-yn-2-yl, 1-pentynyl, pent-4-yn-1-yl or 2-hexynyl, preferably alkynyl radicals having a chain length of 2 to 4 carbon atoms.

Suitable as haloalkyl are alkyl groups which are mono- or polysubstituted, in particular mono- to trisubstituted, by halogen, halogen specifically meaning iodine and in particular fluorine, chlorine and bromine, for example fluoromethyl, difluoromethyl, trifluoromethyl, chloromethyl, dichloromethyl, trichloromethyl, 2-fluoroethyl, 2,2-difluoroethyl, 2-chloroethyl, 2,2-dichloroethyl, 2,2,2-trifluoroethyl and 2,2,2-trichloroethyl.

Cyanoalkyl is, for example, cyanomethyl, cyanoethyl, cyanoeth-1-yl and cyanopropyl.

Hydroxyalkyl is, for example, hydroxymethyl, 2-hydroxyethyl and 3-hydroxypropyl.

Alkenyloxyalkyl is, for example, allyloxyalkyl, methallyloxyalkyl and but-2-en-1-yloxyalkyl.

Alkynyloxyalkyl is, for example, propargyloxyalkyl and 1-methylpropargyloxyalkyl.

Alkoxycarbonyl is, for example, methoxycarbonyl, ethoxycarbonyl, n-propoxycarbonyl, iso-propoxycarbonyl and n-butoxycarbonyl, preferably methoxycarbonyl and ethoxycarbonyl.

Alkenyloxycarbonyl is, for example, allyloxycarbonyl, methallyloxycarbonyl, but-2-en-1-yl-oxycarbonyl, pentenyloxycarbonyl and 2-hexenyloxycarbonyl.

Alkynyloxycarbonyl is, for example, propargyloxycarbonyl, 3-butynyloxycarbonyl, but-2-yn-1-yloxycarbonyl and 2-methylbutyn-2-yloxycarbonyl.

Suitable as haloalkenyl are alkenyl groups which are mono- or polysubstituted by halogen, halogen specifically meaning bromine, iodine and in particular fluorine and chlorine, for example 2- and 3-fluoropropenyl, 2- and 3-chloropropenyl, 2- and 3-bromopropenyl, 2,3,3-trifluoropropenyl, 2,3,3-trichloropropenyl, 4,4,4-trifluorobut-2-en-1-yl and 4,4,4-trichlorobut-2-en-1-yl. Preferred amongst the alkenyl radicals which are mono-, di- or trisubstituted by halogen are those which have a chain length of 3 or 4 carbon atoms. The alkenyl groups on saturated or unsaturated carbon atoms can be substituted by halogen.

Alkoxyalkoxycarbonyl is, for example, methoxymethoxycarbonyl, ethoxymethoxycarbonyl, ethoxyethoxycarbonyl, propoxymethoxycarbonyl, propoxyethoxycarbonyl, propoxypropoxycarbonyl and butoxyethoxycarbonyl.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy and 2,2,2-trichloroethoxy.

The cycloalkyl radicals which are suitable as substituents are, for example, cyclopropyl, cyclobutyl, cyclopentyl and cyclohexyl.

The cycloalkoxycarbonyl radicals which are suitable as substituents are, for example, cyclopropyloxycarbonyl, cyclobutyloxycarbonyl, cyclopentyloxycarbonyl and cyclohexyloxycarbonyl.

The halocycloalkyl radicals which are suitable as substituents are, for example, mono-, di- or up to perhalogenated cycloalkyl radicals, for example fluorocyclopropyl, 2,2-dichlorocyclopropyl, perfluorocyclopentyl or pentachlorocyclohexyl.

Alkoxyalkoxyalkyl is, for example, methoxymethoxymethyl, ethoxymethoxyethyl, ethoxyethoxymethyl, propoxymethoxymethyl, propoxyethoxyethyl, propoxypropoxymethyl, butoxyethoxyethyl and butoxybutoxyethyl.

Alkylthio is, for example, methylthio, ethylthio, propylthio and butylthio, and their branched isomers.

Alkylthioalkyl is, for example, methylthioethyl, ethylthioethyl, methylthiopropyl and ethylthiopropyl.

Alkylthiocarbonylalkyl is, for example, methylthiocarbonylalkyl, ethylthiocarbonylalkyl, n-propylthiocarbonylalkyl, iso-propylthiocarbonylalkyl and n-butylthiocarbonylalkyl.

Alkenylthiocarbonylalkyl is, for example, allylthiocarbonylalkyl, methallylthiocarbonylalkyl, but-2-en-1-yl-thiocarbonylalkyl, pentenylthiocarbonylalkyl and 2-hexenylthiocarbonylalkyl.

Alkynylthiocarbonylalkyl is, for example, propargylthiocarbonylalkyl, 1-methylpropargylthiocarbonylalkyl and but-2-yn-yl-thiocarbonylalkyl.

Haloalkylthio-C(O)— is, for example, fluoromethylthiocarbonyl, difluoromethylthiocarbonyl, trifluoromethylthiocarbonyl, 2,2,2-trifluoroethylthiocarbonyl, 1,1,2,2-tetrafluorethyfthiocarbonyl, 2-fluoroethylthiocarbonyl, 2-chloroethylthiocarbonyl and 2,2,2-trichloroethylthiocarbonyl.

Phenyl, benzyl or benzoyl as part of a substituent, for example phenoxy, phenylthio, benzyloxy, benzylthio, phenoxycarbonyl, benzyloxycarbonyl, phenoxycarbonylalkyl, benzyloxycarbonylalkyl, benzoylamino or benzylamino are in substituted or unsubstituted form. In this case, the substituents can be in the ortho, meta or para position. Examples of substituents are $C_1$–$C_4$alkyl, halogen or $C_1$–$C_4$haloalkyl.

Corresponding meanings can also be allocated to the substituents in composite definitions, for example alkoxy-C(O)—$CH_2$—, HOC(O)-alkoxy, ClC(O)-alkoxy, alkoxycarbonylalkoxy, HOC(O)-alkylthio, alkoxycarbonylalkylthio, haloalkylcarbonyl, haloalkylsulfonyl, $R_{52}$ZC(O)-cycloalkyl, B-haloalkyl, B-haloalkenyl, B-alkoxyalkyl, B-alkylthioalkyl, alkoxycarbonylalkyl, haloalkoxycarbonylalkyl, alkenyloxycarbonylalkyl, alkynyloxycarbonylcycloalkyl, alkenylthio-C(O)-cycloalkyl, ClC(O)-cycloalkyl, ClC(O)-alkoxycarbonyl, haloalkoxycarbonyl, alkynyloxycarbonylalkyl, haloalkylthio-C(O)-alkyl, HOC(O)-cycloalkyl, alkoxycarbonylcycloalkyl and alkenyloxycarbonylcycloalkyl.

In the definition of $R_{20}$, the group

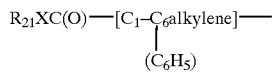

means that the $R_{21}$XC(O)—substituted $C_1$–$C_6$alkylene chain is additionally substituted on one of the 6 carbon atoms by phenyl.

In the definition of $R_{61}$, the groups

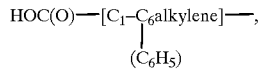

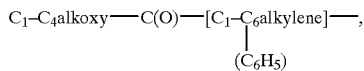

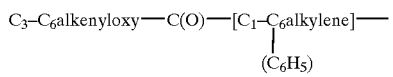

and

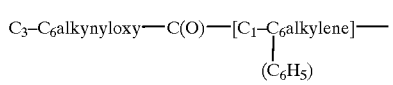

means that the HOC(O)—, $C_1$–$C_4$alkoxy-C(O)—, $C_3$–$C_6$alkenyloxy-C(O)— or $C_3$–$C_6$alkynyloxy-C(O)— substituted $C_1$–$C_6$alkylene chain is additionally substituted on one of the 6 carbon atoms by phenyl ($C_6H_5$).

In the definitions cyanoalkyl, alkylcarbonyl, alkoxycarbonyl, haloalkylcarbonyl, alkylcarbonyloxy, alkoxyalkoxycarbonyl, alkylthiocarbonyl and cycloalkoxycarbonyl, the cyano or carbonyl carbon atom is not included in the lower and upper limitations of the number of carbon atoms given in each case.

A benzyloxy which is mono- to trisubstituted by halogen, $C_1$–$C_4$alkyl or $C_1$–$C_4$haloalkyl, for example in the definition of $R_5$, means that the aromatic ring is substituted by halogen, $C_1$–$C_4$alkyl or $C_1$–$C_4$haloalkyl. The same applies to benzyl and benzyloxycarbonyl which are mono- to trisubstituted, for example in the definition of $R_{10}$, $R_{11}$ and $R_{72}$.

The compounds of the formula I are generally present in the form of mixtures composed of the isomers Ia and Ib

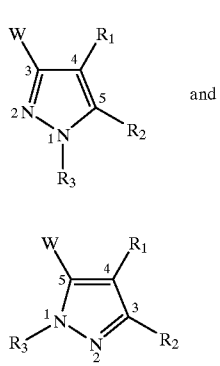

(Ia)

and (Ib)

which are substituted in the 3- and 5-position of the pyrazole ring by the group W. The isomeric ratio Ia/Ib may vary, depending on the synthesis process.

Also part of the invention are the salts which those compounds of the formula I which have an acidic hydrogen, in particular the derivatives which have carboxylic acid and sulfonamide groups (for example carboxyl-substituted alkyl, alkylene, alkoxy, alkylthio, cycloalkyl and phenyl groups and $NH_2SO_2$-substituted phenyl groups) can form with bases. These salts are, for example, alkali metal salts, for example sodium salts and potassium salts; alkaline earth metal salts, for example calcium salts and magnesium salts; ammonium salts, i.e. unsubstituted ammonium salts and mono- or polysubstituted ammonium salts, for example triethylammonium salts and methylammonium salts; or salts with other organic bases.

Substances which are important amongst the alkali metal hydroxides and alkaline earth metal hydroxides as salt formers are, for example, the hydroxides of lithium, sodium, potassium, magnesium or calcium, but in particular those of sodium and potassium.

Possible examples of amines which are suitable for ammonium salt formation are ammonia and also primary, secondary and tertiary $C_1$–$C_8$alkylamines, $C_1$–$C_4$hydroxyalkylamines and $C_2$–$C_4$alkoxyalkylamines, for example methylamine, ethylamine, n-propylamine, isopropylamine, the four isomeric butylamines, n-amylamine, iso-amylamine, hexylamine, heptylamine, octylamine, nonylamine, decylamine, pentadecylamine, hexadecylamine, heptadecylamine, octadecylamine, methylethylamine, methyl-isopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-isopropylamine, di-n-butylamine, di-n-amylamine, di-isoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl-2-amine, di-butenyl-2-amine, n-hexenyl-2-amine, propylenediamine, trimethylamine, triethylamine, tri-n-propylamine, tri-isopropylamine, tri-n-butylamine, tri-isobutylamine, tri-sec-butylamine, tri-n-amylamine, methoxyethylamine and ethoxyethylamine; heterocyclic amines, for example pyridine, quinoline, isoquinoline, morpholine, thiomorpholine, piperidine, pyrrolidine, indoline, quinuclidine and azepine; primary arylamines, for example anilines, methoxyanilines, ethoxyanilines, o,m,p-toluidines, phenylenediamines, benzidines, naphthylamines and o,m,p-chloroanilines; but in particular triethylamine, isopropylamine and di-isopropylamine.

The salts of the compounds of the formula I which have basic groups, in particular basic pyridyl, pyrimidinyl and pyrazolyl rings or of the derivatives with amino groups, for example, alkylamino and dialkylamino groups in the definition of $R_{20}$, or aniline derivatives where $R_5$, $R_6$ or $R_{70}$= amino are, for example, salts with inorganic and organic acids, for example hydrohalic acids such as hydrofluoric acid, hydrochloric acid, hydrobromic acid or hydriodic acid, and also sulfuric acid, phosphoric acid, nitric acid and organic acids such as acetic acid, trifluoroacetic acid, trichloroacetic acid, propionic acid, glycolic acid, thiocyanic acid, citric acid, benzoic acid, oxalic acid, formic acid, benzenesulfonic acid, p-toluenesulfonic acid and methanesulfonic acid.

The fact that at least one asymmetric carbon atom may be possible in the compounds of the formula I, for example in the dyhydrobenzofuranyl moeity of the group $W_3$ on carbon atom 2 or in the substituent $R_6$=$OR_{20}$, in which $R_{20}$ is a branched alkyl, alkenyl, haloalkyl or alkoxyalkyl group, or $R_6$=$S(O)_mR_{30}$, in which, for example, m=1 and/or $R_{30}$ is a branched alkyl, alkenyl, haloalkyl or alkoxyalkyl group, has the result that the compounds can occur not only in optically active individual isomers, but also in the form of racemic mixtures. In the present invention, the active ingredients of the formula I are to be understood as meaning not only the pure optical antipodes, but also the racemates or diastereomers.

If an aliphatic C=C— or C=N—O double bond (syn/anti) exists, geometric isomerism may occur. The present invention also embraces these isomers.

Preferred compounds of the formula I are those in which $R_1$ is methyl; and $R_3$ is methyl or ethyl.

Other preferred compounds of the formula I are those in which $R_4$ is fluorine.

Equally, preferred compounds of the formula I are those in which $R_4$ is chlorine.

Other preferred compounds of the formula I are those in which $R_4$ is hydrogen.

Important compounds of the formula I are those in which W is a group

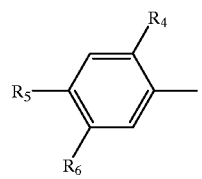

($W_1$), and $R_4$, $R_5$ and $R_6$ are as defined under formula I.

Especially preferred amongst these are the compounds in which $R_5$ is chlorine, bromine, methyl, cyano or trifluoromethyl.

Equally, important compounds of the formula I in which W is a group

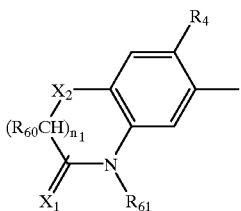

(W₂); and $R_4$, $R_{60}$, $R_{61}$, $X_1$, $X_2$ and $n_1$ are as defined under formula I.

Especially important amongst these are, in particular, those in which $R_4$ is hydrogen, fluorine or chlorine; and $X_1$ is oxygen.

Other important compounds of the formula I are those in which W is a group

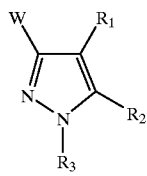

(W₃); $R_4$ is hydrogen, fluorine or chlorine and $B_1$ is methylene.

Important compounds are those of the formula $I_a$

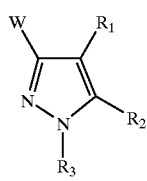

(I_a)

in which W and $R_1$ to $R_3$ are as defined under formula I.

Especially important compounds are those of the formula $I_a$.

(I_a)

in which $R_1$ is methyl; $R_2$ is cyano; and $R_3$ is methyl or ethyl.

Very especially important compounds are those of the formula $I_a$

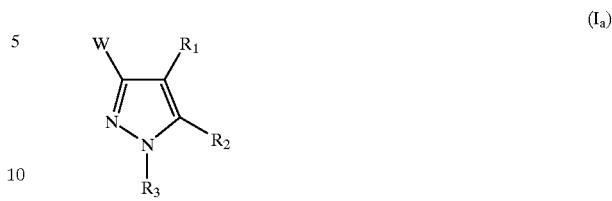

(I_a)

in which $R_1$ is methyl; $R_2$ is cyano; $R_3$ is methyl or ethyl; W is a group

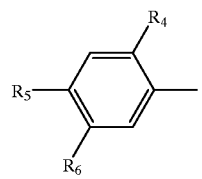

(W₁); and $R_4$ is fluorine or chlorine.

Equally, very especially important compounds are those of the formula $I_a$

(I_a)

in which $R_1$ is methyl; $R_2$ is cyano; $R_3$ is methyl or ethyl; W is a group

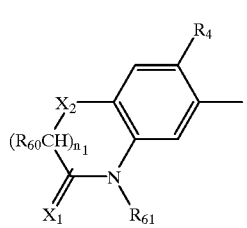

(W₂)

(W₂); and $R_4$ is fluorine or chlorine.

Other very especially important compounds are those of the formula $I_a$

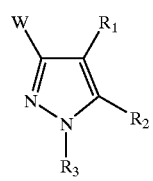

(I_a)

in which $R_1$ is methyl; $R_2$ is cyano; $R_3$ is methyl or ethyl; W is a group

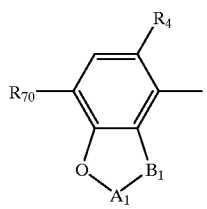

($W_3$); and $R_4$ is fluorine or chlorine.

The process according to the invention for the preparation of compounds of the formula I is carried out in analogy to known processes, for example as described in WO 96/01254, WO 97/00246 and EP-A-0 796 856 and comprises, to prepare those compounds of the formula I

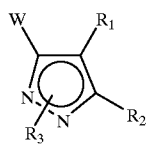
(I)

in which W, $R_1$ and $R_3$ are as defined under formula I and $R_2$ is cyano, a) dehydrating a compound of the formula IIa or IIb

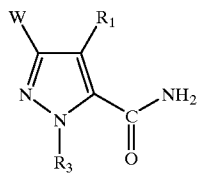
(IIa)

or (IIb)

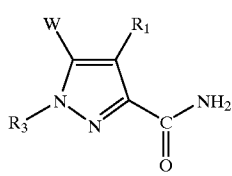

in which W, $R_1$ and $R_3$ are as defined above; or b) first diazotizing a compound of the formula IIIa or IIIb (IIIa)

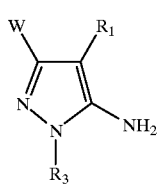

or (IIIb)

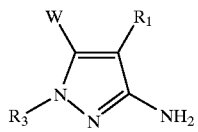

in which W, $R_1$ and $R_3$ are as defined above and subsequently reacting the diazonium salt formed with a salt of the formula X $$M^+CN^-$$ (X)

in which $M^+$ is an alkali metal, alkaline earth metal or transition metal ion; or c) reacting a compound of the formula IVa or IVb (IVa)

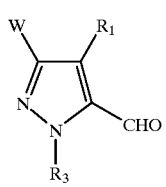 or (IVb)

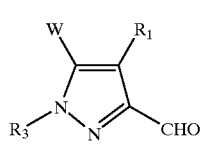

in which W, $R_1$ and $R_3$ are as defined above with hydroxylamine or a salt thereof, for example hydroxylamine·hydrochloride or hydrobromide or acetate, and dehydrating the oxime formed as an intermediate; or d) reacting a compound of the formula Va or Vb (Va)

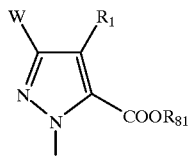

or (Vb)

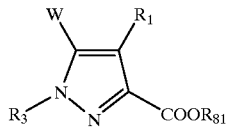

in which W, $R_1$ and $R_3$ are as defined under formula I and $R_{81}$, is $C_1$–$C_4$alkyl, $C_3$- or $C_4$alkenyl or benzyl with dimethylaluminium amide in the presence of an inert organic solvent.

The process according to the invention for the preparation of compounds of the formula I

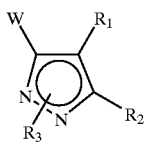
(I)

in which W, $R_1$ and $R_3$ are as defined under formula I and $R_2$ is $NH_2C(S)$— is carried out in analogy to known processes and comprises a) reacting a compound of this formula Ia or Ib

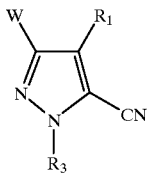
(Ia₁)

or

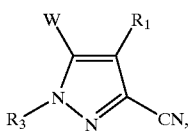
(Ib₁)

with hydrogen sulfide in an organic solvent with base catalysis or with a hydrogen sulfide source with acid catalysis; or b) reacting a compound of the formula IIa or IIb

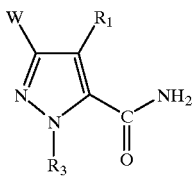
(IIa)

or

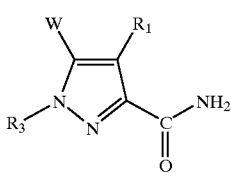
(IIb)

in which W, $R_1$ and $R_3$ as defined above with a suitable sulfur reagent in a solvent.

The process according to the invention for the preparation of compounds of the formula Va and Vb

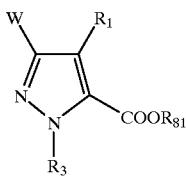
(Va)

or

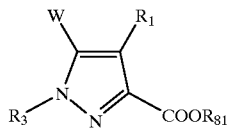
(Vb)

in which $R_1$ and W are as defined under formula I, $R_3$ is $C_1$–$C_4$alkyl, $C_3$- or $C_4$alkenyl or $C_3$- or $C_4$alkynyl; $R_{81}$ is $C_1$–$C_4$alkyl, $C_3$- or $C_4$alkenyl or benzyl comprises either a) converting a compound of the formula XIa

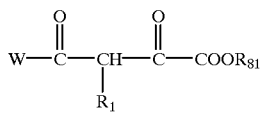
(XIa)

in which W, $R_1$ and $R_{81}$ are as defined above with hydrazine to give the compound of the formula Vc

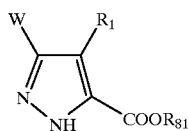
(Vc)

and subsequently alkylating this compound in the presence of a compound of the formula XIIa

$R_3$—$L_1$    (XIIa)

or of the formula XIIb $R_3OSO_2OR_3$    (XIIb)

the radical $R_3$ in the compounds of the formulae XIIa and XIIb being as defined above and $L_1$ being a leaving group; or b) cyclizing a compound of the formula XIa

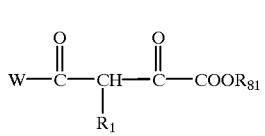
(XIa)

in which W, $R_1$ and $R_{81}$ are as defined above with the compound of the formula XIII

$NH_2NH$—$R_3$    (XIII)

in which $R_3$ is as defined above.

The process according to the invention for the preparation of compounds of the formula VIa and VIb

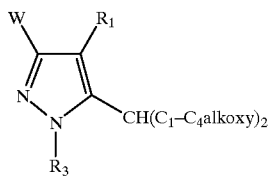
(VIa)

or

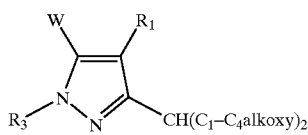
(VIb)

in which $R_1$ and W are as defined under formula I and $R_3$ is $C_1$–$C_4$alkyl, $C_3$- or $C_4$alkenyl or $C_3$- or $C_4$alkynyl comprises cyclizing a compound of the formula XIb

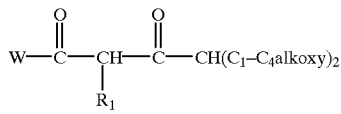
(XIb)

in which W and $R_1$ are as defined above a) with hydrazine to give the compound of the formula VIc

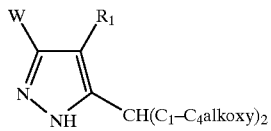
(VIc)

and subsequently alkylating this compound in the presence of a compound of the formula XIIa $R_3$—$L_1$ (XIIa)

or of the formula XIIb $R_3OSO_2OR_3$ (XIIb)

the radical $R_3$ in the compounds of the formulae XIIa and XIIb being as defined above and $L_1$ being a leaving group; or b) with a compound of the formula XIII $NH_2NH$—$R_3$ (XIII)

in which $R_3$ is as defined above.

The compounds of the formula I in which W is a group

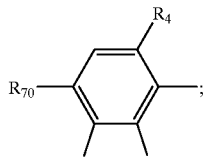
($W_3$)

$A_1$—$B_1$ is a group

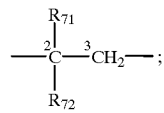

$R_4$, $R_{70}$ and $R_{71}$ are as defined under formula I; and $R_{72}$ is $C_1$–$C_6$ alkyl can be obtained by reacting a compound of the formula VII

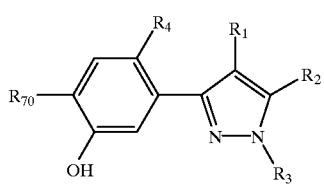
(VII)

in which $R_1$ to $R_4$ and $R_{70}$ are as defined under formula I with a compound of the formula XIV

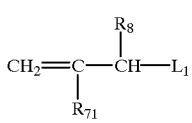
(XIV)

in which $R_{71}$ is as defined above; $R_8$ is hydrogen or $C_1$–$C_5$alkyl; and $L_1$ is a leaving group, in the presence or absence of an inert organic solvent and of a base, to give the compound of the formula VIIIa

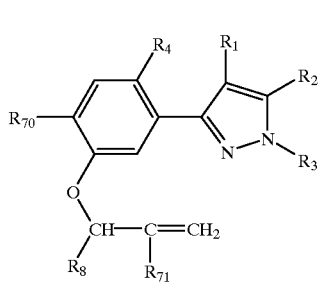
(VIIIa)

in which $R_1$ to $R_4$, $R_8$, $R_{70}$ and $R_{71}$ are as defined above, subjecting this compound to a thermal or acid-catalyzed rearrangement reaction to give the compound of the formula IXa

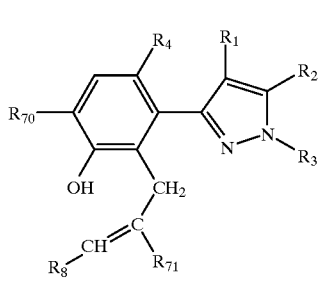

and subsequently cyclizing this compound.

The compound of the formula I in which W is a group

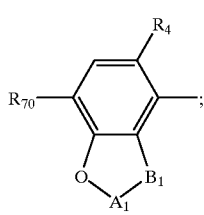

$A_1$—$B_1$ is a group

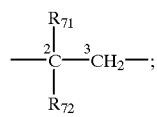

$R_4$, $R_{70}$ and $R_{71}$ are as defined under formula I; and $R_{72}$ is hydroxy-$C_1$–$C_6$alkyl can be obtained by epoxidizing a compound of the formula IXa

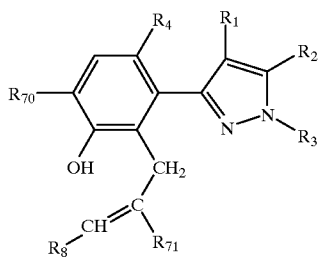

in which $R_1$ to $R_4$, $R_{70}$ and $R_{71}$ are as defined under formula I and $R_8$ is hydrogen or $C_1$–$C_5$alkyl and, if desired, subsequently cyclizing this compound in the presence of a catalyst.

The compounds of the formula I in which W is a group

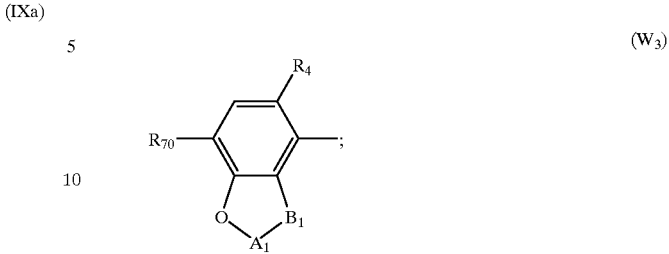

$A_1$—$B_1$ is a group

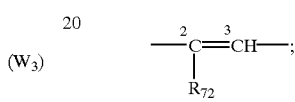

$R_4$ and $R_{70}$ are as defined under formula I; and $R_{72}$ is $C_1$–$C_6$alkyl can be obtained by subjecting a compound of the formula VIIIb

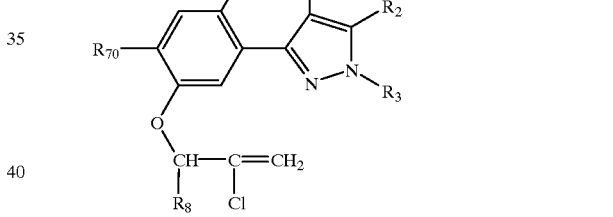

in which $R_1$ to $R_4$ and $R_{70}$ are as defined under formula I and $R_8$ is hydrogen or $C_1$–$C_5$alkyl to a thermal rearrangement reaction to give the compound of formula IXb

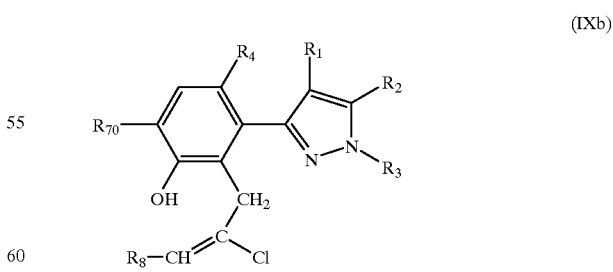

and subsequently cyclizing this compound.

The preparation of the compounds of the formula I is illustrated in greater detail in the reaction diagrams 1 to 7 which follow.

Reaction diagram 1

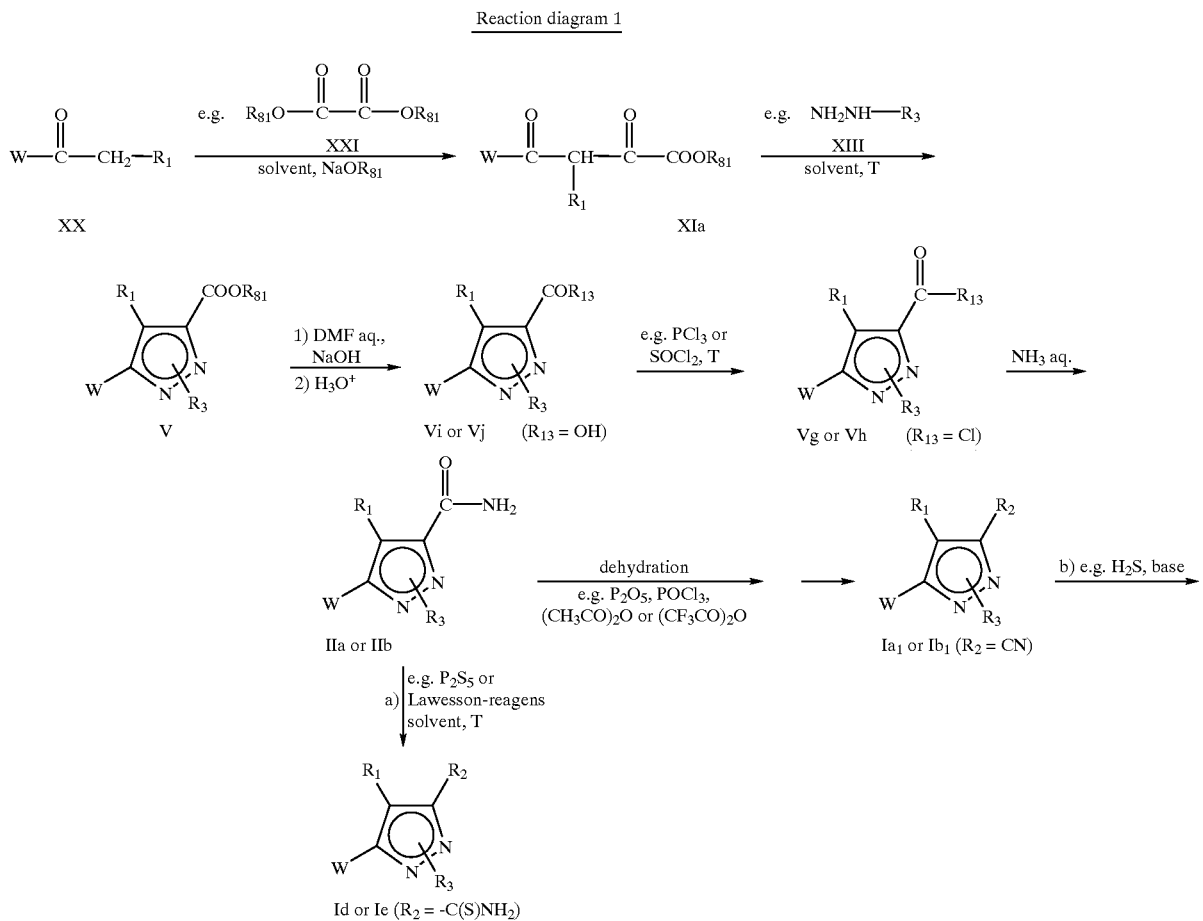

The radicals W, $R_1$ and $R_3$ in reaction diagram 1 are as defined under formula I, $R_1$ being in particular methyl or ethyl and $R_{81}$ being $C_1$–$C_4$alkyl, $C_3$- or $C_4$alkenyl or benzyl.

The ketone derivatives of the formula XX are reacted in accordance with reaction diagram 1 with a dialkyl oxalate of the formula XXI, preferably dimethyl oxalate, in the presence of a base, in particular the corresponding sodium alkoxide, preferably sodium methoxide, in a solvent, for example the corresponding alcohol, preferably methanol, together with a secondary solvent, for example an ether or hydrocarbon, at temperatures from 0° C. to the boiling point of the solvent in question. This condensation reaction and all subsequent reaction steps up to the nitrilo- and thioamidopyrazole derivatives of the formula I ($Ia_1$, $Ib_1$, Id and Ie) in accordance with reaction diagram 1 can be carried out in analogy to the procedure described in, for example, WO 96/01254 (page 20 et seq.).

According to this procedure, the diketo esters of the formula XIa are cyclized with a compound of the formula XIII, for example N-alkylhydrazine, at elevated temperature (reflux), preferably in glacial acetic acid, toluene or an alcohol as the solvent, to give the compounds of the formula V. If desired, an acid, for example sulfuric acid or p-toluenesulfonic acid may be employed as catalyst.

The subsequent conversion of the ester derivatives of the formula V into the corresponding amides of the formula II (IIa or IIb) in accordance with reaction diagram 1 can be effected for example either directly by heating the ester derivatives in aqueous ammonia or, alternatively, via hydrolysis of the ester derivatives of the formula V to give the corresponding carboxylic acid derivatives of the formula Vi or Vj ($R_{13}$=OH) and subsequent heating of the resulting carboxylic acid derivatives in aqueous ammonia or via conversion of the carboxylic acid derivatives of the formula Vi or Vj ($R_3$=OH) into the corresponding carboxylic acid halides of the formula Vg or Vh ($R_{13}$=halogen, in particular chlorine) and subsequently heating the resulting carboxylic acid halides in aqueous ammonia.

The desired nitrolipyrazole derivatives of the formula I (Ia, or $Ib_1$; $R_2$=CN) can be obtained by dehydrating of the amides of the formula II (IIa or IIb) formed as above, for example in analogy to WO 96/01254, pages 23 and 41 et seq. and 'Advanced Organic Chemistry', Editor J. March, Mc Graw-Hill Book Company, N.Y., 1985, page 932 et seq.

The desired cyanopyrazole derivatives of the formula I (Id or Ie) ($R_2$=—C(S)$NH_2$) can be obtained a) from the amides of the formula II (IIa or IIb) by means of sulfur reagents, for example Lawesson reagent, phosphorus pentasulfide or iron sulfide in various polar and unpolar solvents, for example toluene, xylenes, tetrahydrofuran, chloroform, dioxane or N,N-dimethylformamide, at temperatures from 20° C. to 150° C.; or b) from the nitriles of the formula I ($Ia_1$ or $Ib_1$; $R_2$=CN) by means of a hydrogen sulfide source, for example hydrogen sulfide itself, with base catalysis.

The choice of the suitable preparation method and the corresponding reaction conditions depends on the properties (reactivities) of the substituents in the intermediates in question.

The preparation processes of the pyrazole rings are illustrated in greater detail in reaction diagrams 2, 3 and 4 which follow.
Reaction diagram 2
method a):
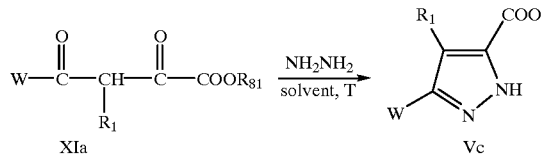
method b):
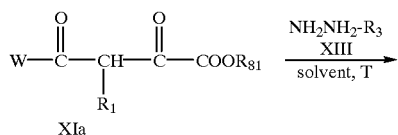
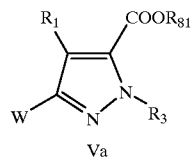
+
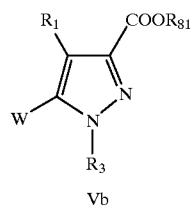
Reaction diagram 3
method a):
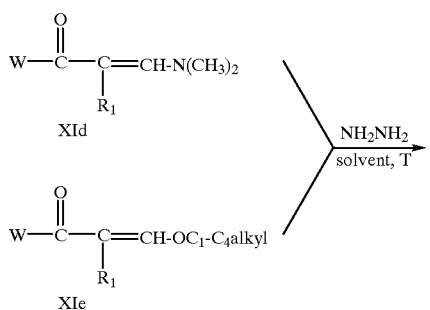
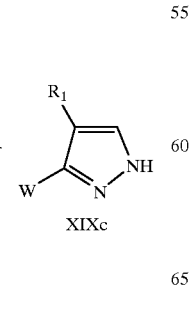
method b):
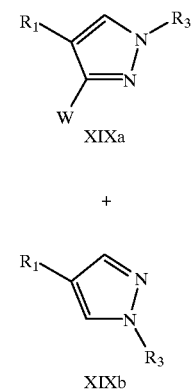
Reaction diagram 4
method a):
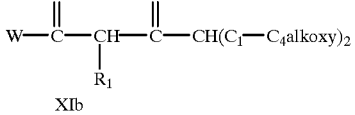
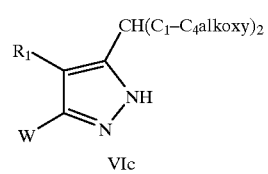
method b):
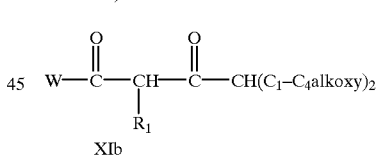
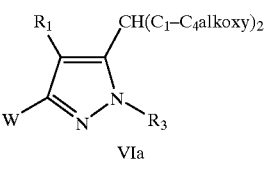
+
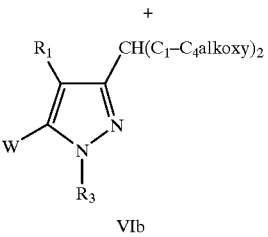
The pyrazole rings of the formulae Vc (reaction diagram 2, method a)) and XIXc (reaction diagram 3, method a)) are prepared by reacting the compounds of the formulae XIa, XId and XIe with hydrazine or hydrazine hydrate at elevated temperature.

To prepare the compound of the formula Vc, it is preferred to use glacial acetic acid or an alcohol as the solvent under mild reflux conditions, and for the preparation of the compound of the formula XIXc it is preferred to use toluene at elevated temperature. If desired, an acid, for example sulfuric acid or p-toluenesulfonic acid, may be employed as catalyst.

The pyrazole ring of the formula VIc, which is unsubstituted on the nitrogen atom (reaction diagram 4, method a), is preferably prepared from the compounds of the formula IXb in alcoholic solution with hydrazine hydrate at elevated temperature.

To prepare the pyrazole rings which are substituted on the nitrogen atom (reaction diagrams 2, 3 and 4, method b)) the procedure is as defined in analogy to method a), the reagent employed being the compound of the formula XIII, for example N-alkylhydrazine, preferably N-methylhydrazine.

The processes in accordance with method b) lead to isomer mixtures Va and Vb, XIXa and XIXb or VIa and VIb, the ratio of the two isomers depending, on the one hand, on the reaction conditions and, on the other hand, on the relevant intermediates of the formulae XIa, XId, XIe or XIb.

The mixtures of the isomeric pyrazole esters of the formulae Va and Vb can be readily separated into the pure isomers by means of silica gel chromatography and/or recrystallization. In general, the same also applies to the isomer mixtures of the formulae XIXa and XIXb, and VIa and VIb.

In certain cases, it is advantageous to prepare the N-alkyl-substituted pyrazole derivatives, in particular the N-methyl-substituted pyrazole derivatives, via N-alkylation of the corresponding unsubstituted pyrazoles of the formulae Vc, XIXc or VIc. This is illustrated in reaction diagram 5.

Reaction diagram 5

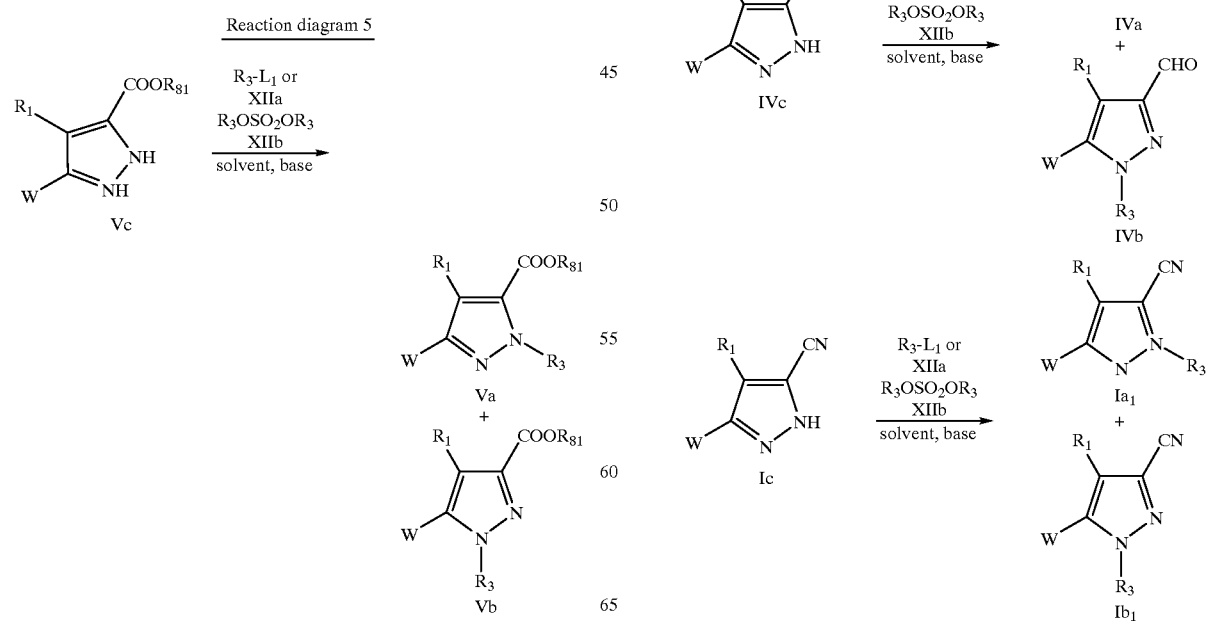

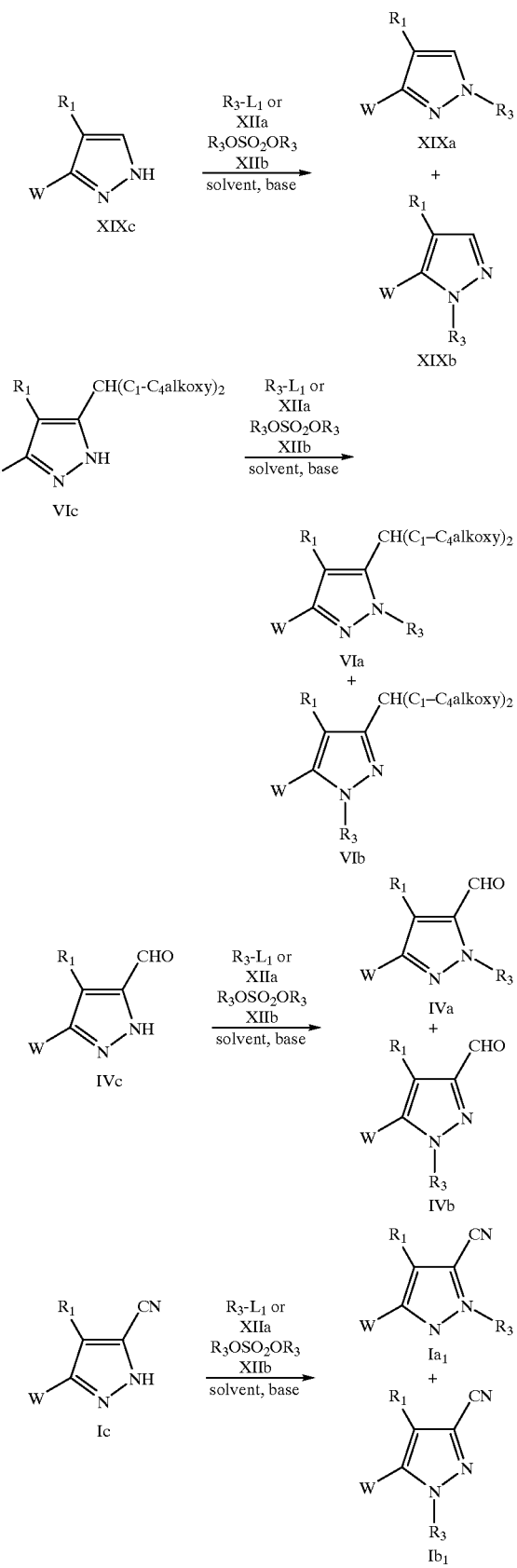

In reaction diagrams 2 to 5, the radical W is an aromatic system $W_1$ to $W_3$ as given under formula I; $R_{81}$ is $C_1$–$C_4$alkyl, $C_3$- or $C_4$alkenyl or benzyl; $R_1$ is $C_1$–$C_4$alkyl; $R_3$ is $C_1$–$C_4$alkyl, $C_3$- or $C_4$alkenyl or $C_3$- or $C_4$alkynyl; and $L_1$ is a leaving group, for example chlorine, bromine, iodine, $CH_3SO_2O$— or

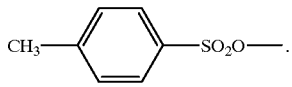

The pyrazole rings in the compounds of the formulae Vc, XIXc, VIc, IVc and Ic in reaction diagram 5 are N-alkylated at room temperature or moderately elevated temperatures in the presence of a solvent, for example acetone, methyl ethyl ketone, N,N-dimethylformamide, N-methylpyrrolidone or dimethyl sulfoxide, of a base, for example potassium carbonate, sodium carbonate, sodium hydroxide or potassium hydroxide, and of an alkylating agent of the formula XIIa or XIIb, preferably methyl iodide or dimethyl sulfate.

N-Alkylation of the pyrazole rings leads to isomer mixtures of the formulae Va and Vb, XIXa and XIXb, VIa and VIb, IVa and IVb, and $Ia_1$ and $Ib_1$ all of which can generally be separated into the pure isomers by customary processes.

The preparation of the pyrazole derivatives of the formula $Ia_1$—which are cyano-substituted in the 5-position—starting from the various intermediates of the formulae IIa, IIIa, IVa and Va, is illustrated in reaction diagram 6. The choice of the suitable preparation method and the relevant reaction conditions depends on the properties (reactivities) of the substituents in the intermediates in question.

Reaction diagram 6 method a):

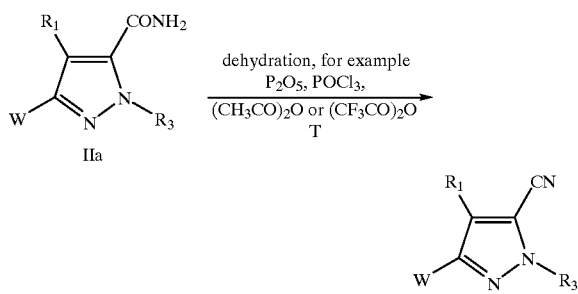

method b):

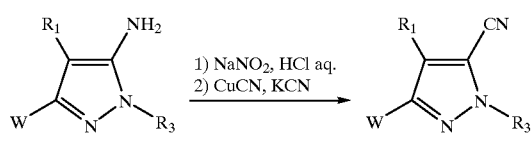

method c):

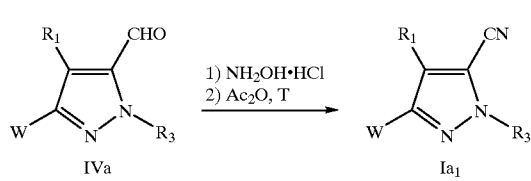

-continued method d):

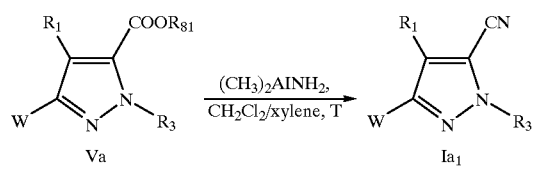

In reaction diagram 6, the radicals W and $R_1$ are as defined under formula I, and $R_3$ ist $C_1$–$C_4$alkyl, $C_3$- or $C_4$alkenyl or $C_3$- or $C_4$alkynyl.

The reaction in accordance with method a) in reaction diagram 6 is effected in analogy to 'Advanced Organic Chemistry', Editor J. March, McGraw-Hill Book Company, N.Y., 1985, page 932 et seq. and converts primary amides of the formula IIa into the cyanopyrazoles of the formula $Ia_1$ with dehydration, for example using phosphorus pentoxide ($P_2O_5$), phosphorus oxychloride ($POCl_3$), acetic anhydride or trifluoroacetic anhydride, or carbon tetrachloride/triphenylphosphine ($CCl_4/P(C_6H_5)_3$), in the presence or absence of an inert solvent at elevated temperature.

The reaction in accordance with method b) in reaction diagram 6 is effected in analogy to 'Vogel's Textbook of Practical Organic Chemistry', 1989, page 938; according to this method, aminopyrazoles of the formula IIIa are first diazotized with sodium nitrite at low temperatures, for example $-10°$ C. to $15°$ C., in aqueous hydrochloric acid and the diazonium salts formed are converted into the cyano derivatives of the formula $Ia_1$ with an aqueous solution of the salt of the formula X $$M^+CN^-  \hspace{3cm} (X)$$

in which $M^+$ is an alkali metal ion, alkaline earth metal ion or transition metal ion, for example copper(1) cyanide or potassium cyanide (Sandmeyer reaction).

The reaction in accordance with method c) in reaction diagram 6 is effected in analogy to 'Vogel's Textbook of Practical Organic Chemistry', Longman 1989, page 1084, and allows pyrazolealdehydes of the formula IVa to react with hydroxylamine·hydrochloride in protic solvents to give oximes which are dehydrated in acetic anhydride at elevated temperature to give the cyanopyrazoles of the formula $Ia_1$.

In the reaction in accordance with method d) in reaction diagram 6, ester pyrazoles of the formula Va are used which can be converted directly into the nitriles of the formula Ia, in a mixture of inert solvents, preferably hexane, heptane, dichloromethane or xylene, and with heating to reflux temperature, with the aid of dimethylaluminium amide $((CH_3)_2AlNH_2)$, which is freshly prepared from commercially available trimethylaluminium in accordance with known processes.

The reagents of the formulae X, XIIa, XIIb and XIII which are used in reaction diagrams 2 to 5 are known.

The pyrazolecarboxylic acids of the formula Vi

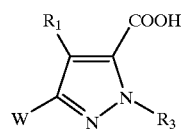

(Vi)

can be obtained in analogy to known processes
a) from the corresponding ester derivatives of the formula Va

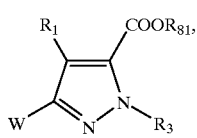

(Va)

the radicals W, $R_1$ and $R_3$ in the compounds of the formulae Va and Vi being as defined under formula I and $R_{81}$ being $C_1$–$C_4$alkyl, $C_3$- or $C_4$alkenyl or benzyl, by means of hydrolysis, preferably with aqueous alcohols, aqueous tetrahydrofuran or aqueous N,N-dimethylformamide (DMF) in the presence of sodium hydroxide or potassium hydroxide at average temperatures, for example 0° C. to reflux temperature of the reaction mixture, followed by work-up under acidic conditions, or b) by oxidation of an aldehyde of the formula IVa

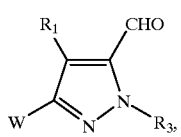

(IVa)

for example with potassium permanganate.

The pyrazolecarboxylic acid chlorides of the formula Vg

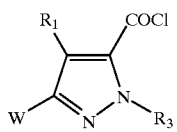

(Vg)

can be prepared in analogy to known processes, for example 'Organikum' [Organic chemistry], Ed. J. A. Barth, Leipzig, 1993, page 439 et seq. from the corresponding pyrazolecarboxylic acids of the formula Vi

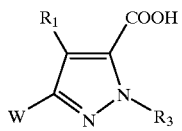

(Vi)

with inorganic acid chlorides, for example phosphorus trichloride or thionyl chloride, at elevated temperatures in the presence or absence of an inert solvent, the radicals W, $R_1$ and $R_3$ in the compounds of the formulae Vg and Vi being as defined above.

The pyrazolecarboxamides of the formula IIa

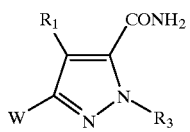

(IIa)

can be prepared in analogy to known processes
a) from the corresponding carboxylic acid chlorides of the formula Vg

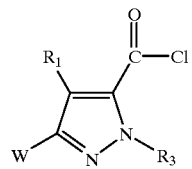

(Vg)

and aqueous ammonia solution at average temperatures, or b) from certain ester derivatives of the formula Va

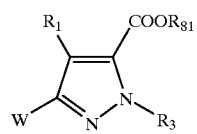

(Va)

in the presence of aqueous ammonia solution, the radicals W, $R_1$ and $R_3$ in formulae IIa, Vg and Va being as defined under formula I and $R_{81}$ being $C_1$–$C_4$alkyl, C3- or $C_4$alkenyl or benzyl, $R_{81}$ being in particular methyl.

In certain cases, for example when the nucleophilic character of the pyrazole ring is more pronounced than that of the phenyl ring, the aminopyrazoles of the formula IIIa

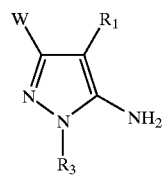

(IIIa)

can be obtained by known processes, for example as described in Austr. J. Chem. 32,1727 (1979); J. Chem. Soc., Perkin Trans. 2,382 (1974); or J. Heterocycl. Chem. 20,277 (1983), from the compounds of the formula XIXa

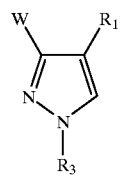

(XIXa)

by nitrating these compounds and subsequently reducing the nitro group; or in analogy to known processes, for example as described in J. Heterocycl. Chem. 19, 1173 (1982); Khim. Geterotsikl. Soedin 1990, 1092; Ber. Deutsch. Chem. Ges. 26, 2053 (1893); or Chem. Ber. 99, 1769 (1966), from compounds of the formula XXa

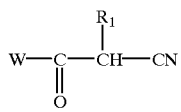
(XXa)

in which W and R$_1$ are as defined under formula I and compounds of the formula XIII $$H_2NNH-R_3 \quad (XIII)$$

or a salt thereof, for example the corresponding hydrochloride or hydrobromide or acetate, preferably in a solvent, for example an alcohol or alcohol/water mixture or in acetic acid, at reaction temperatures of 20° C. to 100° C.

The pyrazolealdehydes of the formula IVa

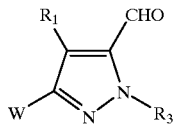
(IVa)

can be prepared by known processes, for example as described in Arch. Pharm. 264, 337 (1926) and Liebigs Annalen 437, 297 (1924), a) from the corresponding acid chlorides of the formula Vg

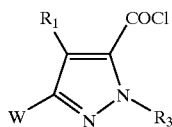
(Vg)

or b) from the corresponding acetals of the formula VIa

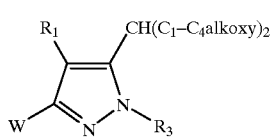
(VIa)

by acid hydrolysis, for example with hydrochloric acid, sulfuric acid or p-toluene-sulfonic acid, the radicals W, R$_1$ and R$_3$ in the compounds of the formulae IVa, Vg and VIa, being as defined under formula I.

The preparation of the pyrazole thioamides of the formula Id starting from the corresponding pyrazolenitriles of the formula Ia$_1$ or pyrazole amides of the formula IIa is effected in analogy to known processes, for example as described in 'Methodicum Chimicum', Volume 6, Georg Thieme Verlag, Stuttgart, 1974, page 768 et seq. and 'Methoden der Organischen Chemie' [Methods in organic chemistry] (Houben-Weyl), Volume E5, Georg Thieme Verlag, Stuttgart, 1985, page 1242 et seq., and is illustrated in reaction diagram 7.

Reaction diagram 7 method a):

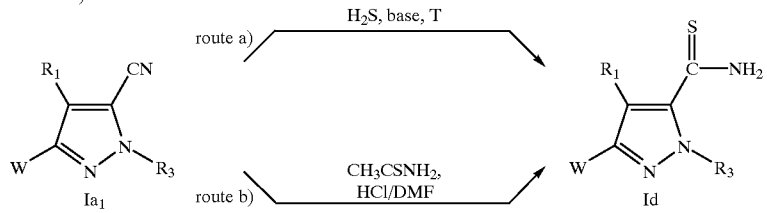

method b):

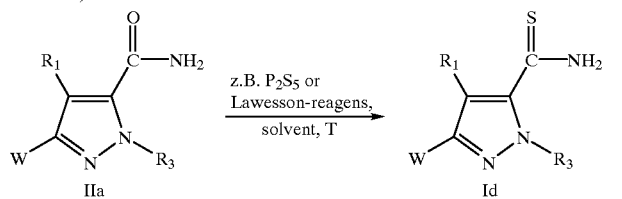

In reaction diagram 7 the radicals W, $R_1$ and $R_3$ in the compounds of the formulae $Ia_1$, IIa and Id are as defined under formula I, taking into consideration the reactivity or stability characteristics of the substituents under the reaction conditions chosen.

The reaction in accordance with method a), route a), in reaction diagram 7 uses pyrazolenitriles of the formula $Ia_1$ which can be converted into the pyrazole thioamides of the formula Id with hydrogen sulfide and base catalysis, for example with metal hydroxides, basic ion exchangers, alkoxides, ammonia or organic bases, for example pyridine and triethylamine, in an organic solvent, for example pyridine or an alcohol. If desired, the use of a stronger base, for example tetramethylguanidine, in solvents, for example sulfolane, as catalyst may be indicated. Depending on the reactivity of the reactants, the reaction temperatures can vary greatly; the reaction may also be carried out in a pressurized reactor if desired.

The reaction in accordance with method a), route b), in reaction diagram 7 also uses pyrazolenitriles of the formula $Ia_1$, which can be converted into the corresponding pyrazole thioamide of the formula Id with a hydrogen sulfide source, for example thioacetamide, in dry N,N-dimethylformamide with acid catalysis, for example with dry hydrogen chloride, at temperatures of from 20° C. to 150° C.

The reaction in accordance with method b) in reaction diagram 7 starts from primary amides of the formula IIa which, in the presence of the sulfur reagents mentioned under method a) or other sulfur reaagents, for example Lawesson reagent, phosphorus pentasulfide or iron sulfide, in a variety of polar and unpolar solvents, for example toluene, xylenes, tetrahydrofuran, chloroform, dioxane or N,N-dimethylformamide, and at temperatures of from 20° C. to 150° C. give the pyrazole thioamides of the formula Id.

All other compounds from amongst the scope of the formula I can be prepared in analogy to the procedure described above, or following methods as they are described, for example, in "Methoden der Organischen Chemie" [Methods in organic chemistry] (Houben-Weyl), Volume E 8b, Georg Thieme Verlag Stuttgart, 1994, page 399 et seq., in "Pyrazoles, Pyrazolines, Pyrazolidines, Indazoles and Condensed Rings", Editor R. H. Wiley, Interscience Publishers, New York, 1967, page 1 et seq., or in "Comprehensive Heterocyclic Chemistry", Editors A. R. Katritzky and C. W. Rees, Pergamon Press, Oxford, 1987, or from the described compounds of the formula I by derivatization following known standard methods as they are described, for example, in "Advanced Organic Chemistry", Third Edition, Editor J. March, John Wiley & Sons, New York, 1985; in "Comprehensive Organic Transformations", Editor R. C. Larock, VCH Publishers, Inc., New York, 1989; or in "Comprehensive Organic Functional Group Transformations", Editors A. R. Katritzky, O. Meth-Cohn, C. W. Rees, Pergamon Press, Oxford, 1995.

The starting compounds of the formula XX in reaction diagram 1 can be prepared in analogy to known processes, for example in accordance with methods a), b), c) and d) given in reaction diagram 8 below.

Reaction diagram 8 method a):

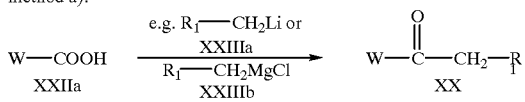

-continued method b):

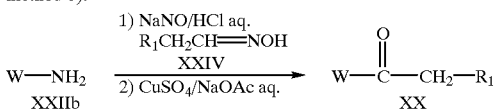

method c):

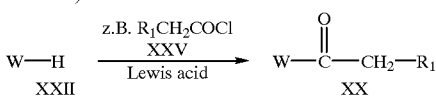

method d):

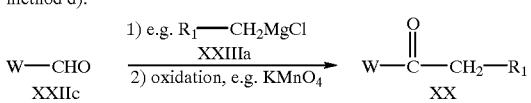

In reaction diagram 8, the radical W is a group $W_1$, $W_2$ or $W_3$, as defined under formula I, but it must be taken into consideration that not every definition of substituents is compatible with all the processes given. The choice of the suitable preparation method depends on the properties (reactivities) of the substituents in the intermediates in question.

The reaction in accordance with method a) in reaction diagram 8 is effected for example starting from the carboxylic acid of the formula XXIIa with alkyllithium of the formula XXIIIa or a Grignard compound of the formula XXIIIb (alkylmagnesium chloride or alkylmagnesium bromide) in an inert solvent, preferably diethyl ether, at temperatures of from −100° C. to 50° C., in analogy to Organic Reactions 18, 1 (1970), Organic Synthesis 49, 81 (1969) and 'Comprehensive Organic Transformations', Editor R. C. Larock, VCH 1989, page 685.

The reaction in accordance with method b) in reaction diagram 8 is effected in analogy to J. Chem. Soc. 1954, 1297. The amines of the formula XXIIb are first diazotized to give the corresponding diazonium salts and these are reacted with the oxime of the formula XXIV. Subsequent hydrolysis, for example with aqueous sodium acetate and copper sulfate, gives the corresponding methyl ketone of the formula XX.

The reaction in accordance with method c) in reaction diagram 8 is effected in analogy to 'Vogel's Textbook of Practical Organic Chemistry', Longman 1989, page 1006 et seq. Here, the aromatic compound of the formula XXII is reacted in the presence of an alkanecarboxylic acid derivative of the formula XXV for example propionyl chloride, and an acid, for example Lewis acids such as aluminium chloride, with or without solvent at temperatures of from 0° C. to 150° C.

The reaction in accordance with method d) in reaction diagram 8 is effected in analogy to 'Advanced Organic Chemistry', Editor J. March, McGraw-Hill Book Company, New York, 1985, pages 816 et seq. and 1057 et seq., starting from an aldehyde of the formula XXIIc, by means of a Grignard reagent of the formula XXIIIb for example ethylmagnesium chloride or ethyl magnesium bromide, or by means of ethyllithium in an inert solvent, preferably diethyl ether, at temperatures of from −80° C. to 25° C. and subsequent oxidation of the alcohol to give the ketone. Suitable oxidants are, for example, potassium permanganate, pyridinium dichromate and sodium dichromate.

The starting compounds of the formulae XXII, XXIIa, XXIIb and XXIIc are known and can be prepared by processes which have been disclosed.

The starting compounds of the formula XXa can be prepared in analogy to standard processes, for example a) via Reformatsky reaction of a bromonitrile of the formula XV

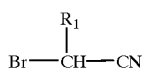 (XV)

in which $R_1$ is as defined under formula I with a nitrile of the formula XXIId W—CN (XXIId)

in which W is as defined under formula I and subsequent hydrolysis in analogy to the procedure described in, for example, Organomet. Chem. 71, 325 (1974); or b) via condensation of a nitrile of the formula XVI $R_1$—$CH_2$—CN (XVI)

in which $R_1$ is as defined under formula I with an ester of the formula XXIIe

W—$COOR_7$ (XXIIe)

in which W is as defined above and $R_7$ is methyl or ethyl in the presence of a base, for example an alkoxide, for example sodium methoxide or sodium ethoxide, in a solvent, for example methanol or ethanol, in analogy to the procedure described in, for example, J. Am. Chem. Soc. 54, 2960 (1932); ibid. 79, 723 (1957); or in Tetrahedron Lett. 1979, 1585; or c) via substitution of the compound of the formula XXb

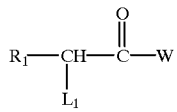 (XXb)

in which W and $R_1$ are as defined above and $L_1$ is a leaving group, for example chlorine or bromine, in analogy to the procedure described in, for example, J. Heterocycl. Chem. 21, 1849 (1984); or d) via alkylation of a ketonitrile of the formula XXc

 (XXc)

with an alkylating agent of the formula XIIc $R_1$—$L_1$ (XIIc),

W and $R_1$ in the compounds of the formulae XXc and XIIc being as defined above and $L_1$ being a leaving group, for example, chlorine, bromine or $C_6H_5SO_2O$—, in the presence of a base and of a solvent in analogy to the procedure described in, for example, J. Am. Chem. Soc. 61, 1940 (1939).

The intermediates of the formulae XIa, XIb, XId and XIe in reaction diagrams 2 to 4 can be prepared in analogy to known processes from the above-described methyl ketones of the formula XX, for example in accordance with methods a), b), c) and d) given in reaction diagram 9 below.

Reaction diagram 9

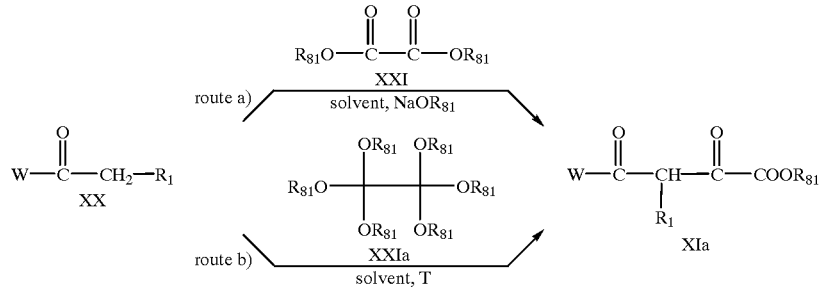

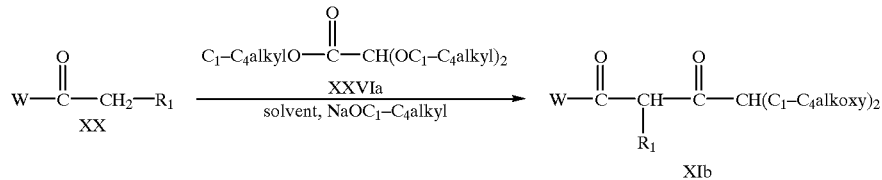

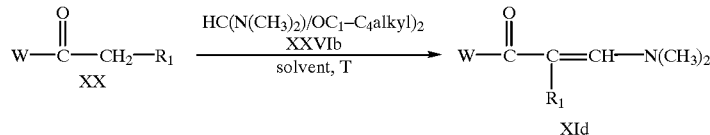

method d):

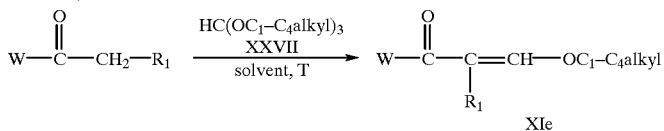

The radicals W and $R_1$ in reaction diagram 9 are as defined under formula I, and $R_{81}$ is $C_1$–$C_4$alkyl, $C_3$- or $C_4$alkenyl or benzyl, in particular methyl or ethyl.

The reaction in accordance with method a) in reaction diagram 9 gives the diketo esters of the formula XIa, either by reacting route a) the ketone of the formula XX with a dialkyl oxalate of the formula XXI, preferably dimethyl malonate, in the presence of a base, in particular the corresponding sodium alkoxide, in a solvent, for example the corresponding alcohol $R_{81}OH$, together with a secondary solvent, for example an ether or hydrocarbon, at temperatures of from 0° C. to the boiling point of the solvent in question, in analogy to Chem. Communic. 1995, 1549; Liebigs Ann. 641, 63 (1961); and J. Chem. Soc. 1943, 491, or route b) the ketone of the formula XX with a hexaalkoxyethane of the formula XXIa, preferably hexamethoxy- or hexaethoxyethane, with or without solvent, at temperatures of from 20° C. to the boiling point of the reaction medium in question. If the reaction is carried out in a solvent, then toluene is preferred. The reaction can be catalyzed by acids, for example hydrochloric acid, sulfuric acid, methanesulfonic acid, p-toluenesulfonic acid or trifluoroacetic acid.

The reactions in accordance with methods c) and d) in reaction diagram 9 proceed in analogy to the procedure described under a) and give the intermediates of the formulae XId and XIe. If the ketone of the formula XX is reacted, on the one hand, with acetals of N,N-dimethylformamide of the formula, XXVIb, preferably N,N-dimethylformamide dimethyl acetal or N,N-dimethylformamide diethyl acetal, the intermediates of the formula XId are formed, or, on the other hand, with orthoformates of the formula XXVII, preferably methyl orthoformate or ethyl orthoformate, the intermediates of the formula XIe are formed.

The reaction of the ketone of the formula XX in accordance with method b) in reaction diagram 9 with acetal esters of the formula XXVIa, preferably methyl dimethoxyacetate or ethyl diethoxy acetate, in the presence of a base, preferably sodium methoxide or sodium ethoxide, and of a solvent, in particular methanol or ethanol, at temperatures of from 0° C. to the boiling point of the reaction mixture gives the diketo acetals of the formula XIb. In certain cases, a further solvent, for example ether, can also be added.

To prepare the phenylpyrazoles of the formula I which are substituted in the 5-position of the phenyl ring (group $W_1$, substituent $R_6$), a large number of known standard processes is available, the choice of the suitable preparation processes depending on the properties (reactivities) of the substituents in the intermediates in question. Some illustrative examples are given in reaction diagrams 10 to 13.

The preparation of the phenylpyrazole derivatives of the formula I ($W=W_1$) which are O-substituted in the 5-position of the phenyl ring, and in which $R_6=OR_{20}$, starting from the methoxy- or benzyloxy-substituted derivatives of the formula $I_{37}$ or $I_{38}$ is illustrated in reaction diagram 10.

Reaction diagram 10

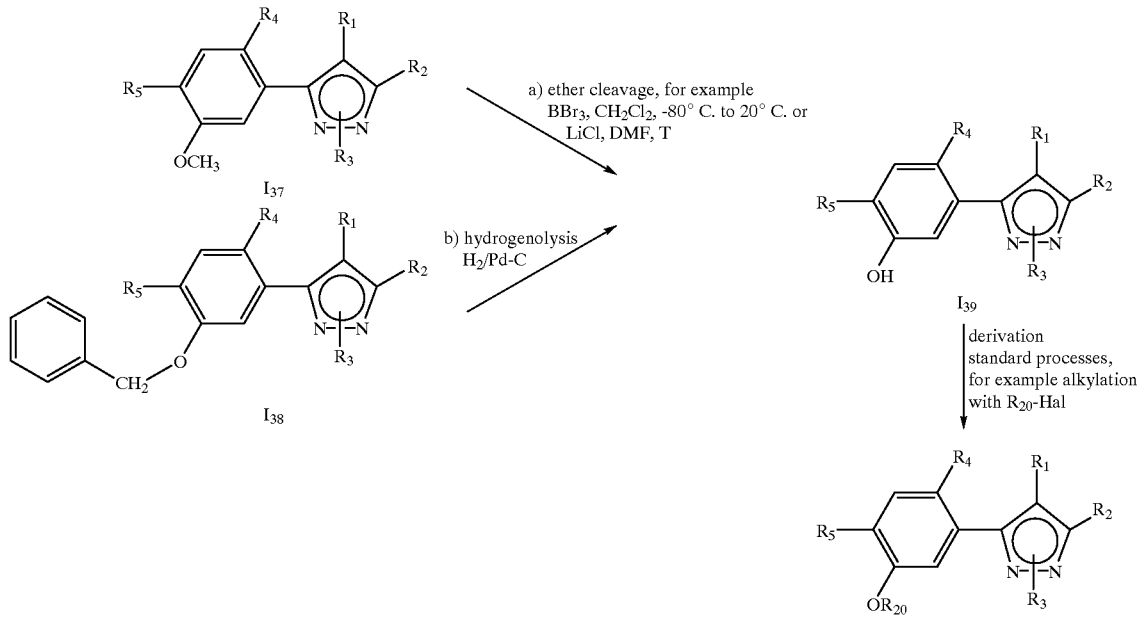

The phenylpyrazole derivatives of the formula $I_{39}$ in reaction diagram 10 can be obtained for example a) from the compounds of the formula $I_{37}$ via ether cleavage by means of lithium chloride in N,N-dimethylformamide (DMF) at elevated temperature, for example as described in Synthesis 1989, 287, or by means of boron tribromide in dichloromethane at temperatures of from −80° C. to 20° C., for example as described in Org. Synth., Collect. Vol. V, 412, 1973; or b) from the compound of the formula $I_{38}$ via hydrogenolysis by means of hydrogen in the presence of a catalyst, for example palladium on charcoal, for example as described in J. Am. Chem. Soc. 93, 746 (1971). Derivatization of the phenylpyrazole of the formula $I_{39}$ in reaction diagram 10 to give the compounds of the formula I can be carried out by standard processes, for example via alkylation with $R_{20}$-hal, in which $R_{20}$ is as defined under formula I and hal is halogen, in particular chlorine, bromine or iodine.

The preparation of the phenylpyrazole derivatives of the formula I ($W=W_1$) which are S-substituted in the 5-position of the phenyl ring, and in which $R_6=S(O)_mR_{30}$, starting from the derivatives of the formula $I_{40}$ which are unsubstituted in the 5-position is illustrated in reaction diagram 11.

Reaction diagram 11

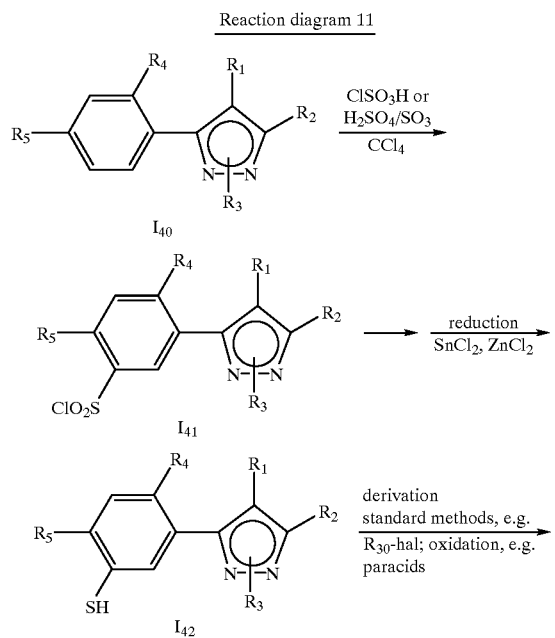

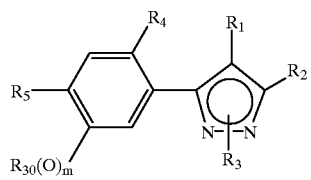

$I (W = W_1; R_6 = S(O)_m R_{30})$

The preparation of the thiophenylpyrazoles of the formula $I_{42}$ in reaction diagram 11 can be effected in analogy to known processes, for example as described in J. Org. Chem. 54, 6096 (1989), EP-A-0 259 265 or in "Sulfonation and Related Reactions", Editor Gilbert, Interscience Publishers, New York, 1965. Thereafter, the phenylpyrazole of the formula $I_{40}$ can be chlorosulfonylated with chlorosulfonic acid or sulfur trioxide in sulfuric acid to give the compound of the formula $I_{41}$ and this is subsequently reduced with tin chloride or zinc chloride to give the thiophenol derivative of the formula $I_{42}$. Derivatization of the thiophenylpyrazoles of the formula $I_{42}$ to give the compounds of the formula I in reaction diagram 11 can be effected by standard processes, for example via alkylation with $R_{30}$-hal, in which $R_{30}$ is as defined under formula I and hal is halogen, in particular chlorine, bromine or iodine (m=0). The subsequent oxidation to give the sulfone or sulfone derivatives of the formula I (m=1 or 2, respectively) can equally be carried out by standard processes, for example with peracids, for example m-chloroperbenzoic acid.

The preparation of the phenylpyrazole derivatives of the formula I ($W=W_1$) which are carboxyl-substituted in the 5-position of the phenyl ring, and in which $R_6$=halogen, cyano, nitro, amino, $R_{10}NH$ or $R_{10}R_{11}N$, starting from the derivatives of the formulae $I_{40}$ and $I_{47}$ which are unsubstituted or triflate-substituted in the 5-position, respectively, is illustrated in reaction diagram 12.

Reaction diagram 12

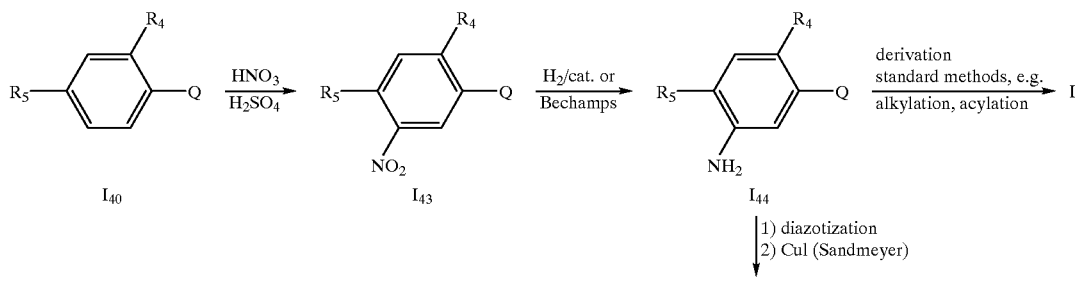

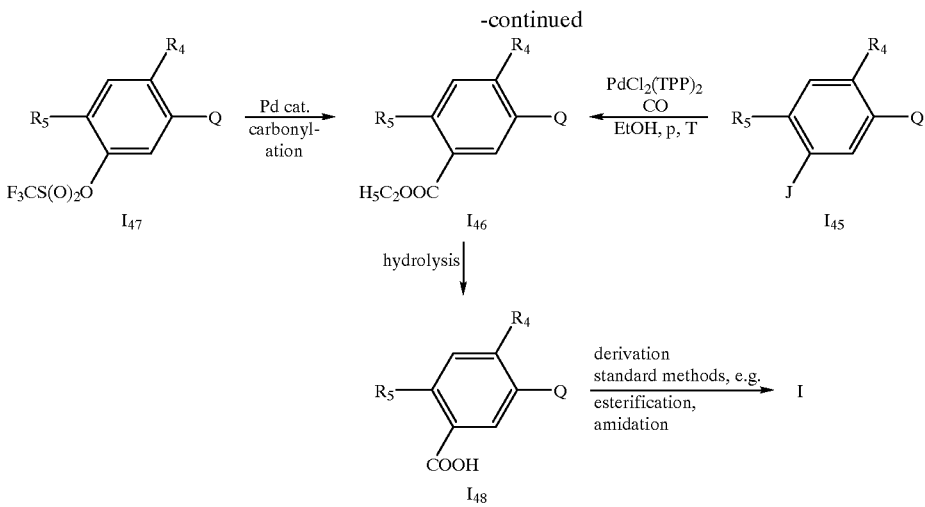

In reaction diagram 12, Q is the radical

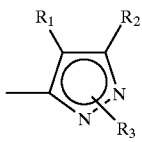

in which $R_1$ to $R_3$ are as defined under formula I.

In accordance with reaction diagram 12, the phenylpyrazole of the formula $I_{40}$ can be converted into the aniline derivative of the formula $I_{44}$ by standard processes, for example nitration in a mixture of nitric and sulfuric acid and subsequent reduction of the resulting nitro compound of the formula $I_{43}$ with hydrogen in the presence of a catalyst, or by the method of Bechamps. Then, the aniline derivative of the formula $I_{44}$ can either be derivatized directly by standard processes, for example acylation or ethylation, to give the corresponding compounds of the formula I or converted into the halogen compound of the formula $I_{45}$ by means of diazotization and Sandmeyer reaction. The benzoate of the formula $I_{46}$ in reaction diagram 12 can be obtained for example in analogy to J. Org. Chem. 39, 3318 (1974) or ibid. 40, 532 (1975) from the compound of the formula $I_{45}$ by means of carbon monoxide and a catalyst, for example palladium chloride triphenylphosphine $(PdCl_2(TPP)_2)$ in the presence of a solvent, for example ethanol, at elevated temperature, with or without pressure. A further possibility of synthesizing the intermediate of the formula $I_{46}$ is in analogy to Tetrahedron Letters 25, 2271 (1984) and ibid. 27, 3931 (1986). In accordance with this, the compound of the formula $I_{47}$ is carbonylated in the presence of a catalyst, for example palladium. Subsequent hydrolysis of the benzoate ester of the formula $I_{46}$ gives the benzoic derivative of the formula $I_{48}$, which can be converted into the corresponding compounds of the formula I by standard processes, for example esterification or amidation.

The preparation of the phenylpyrazole derivatives of the formula I (W=$W_1$) which are substituted in the 5-position of the phenyl ring and in which $R_6$ $R_{52}ZC(O)$—$C_1$-$C_8$alkyl, $R_{52}ZC(O)$—$C_1$-$C_8$haloalkyl, $R_{52}ZC(O)$—$C_2$-$C_8$alkenyl, $R_{52}ZC(O)$—$C_2$-$C_8$alkynyl, $R_{52}ZC(O)$—$C_2$-$C_8$haloalkenyl, $R_{52}ZC(O)$—$C_1$-$C_4$alkoxy-$C_1$-$C_4$alkyl or $R_{52}ZC(O)$—$C_1$-$C_4$alkylthio-$C_1$-$C_4$alkyl, starting from the derivatives of the formula $I_{45}$ which are substituted in the 5-position of the phenyl ring by halogen, in particular chlorine, bromine or iodine, via a Heck reaction (route a)) or starting from the derivatives of the formula $I_{44}$ which are amino-substituted in the 5-position of the phenyl ring via diazotization and subsequent Meerwein reaction (route b)) is illustrated in reaction diagram 13.

Reaction diagram 13

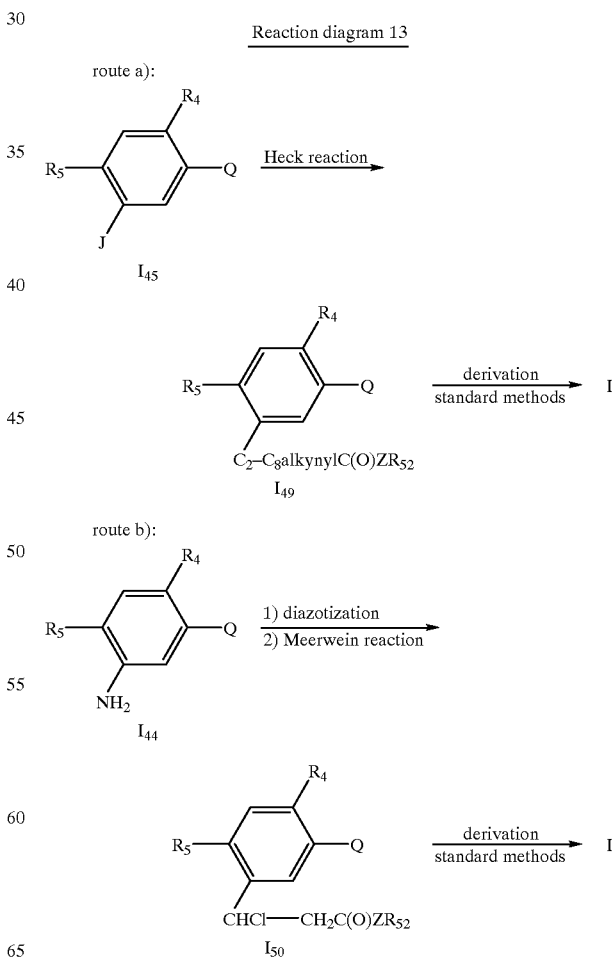

In reaction diagram 13, Q is the radical

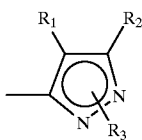

in which $R_1$ to $R_3$ are as defined under formula I.

In accordance with reaction diagram 13, route a), the alkynyl ester derivatives of the formula $I_{49}$ can be prepared for example via a Heck reaction in analogy to R. F. Heck in W. G. Dauben (Edit.), Organic Reactions 27, 345 (1982). The corresponding $R_{52}ZC(O)$alkenyl or $R_{52}ZC(O)$alkyl derivatives can be obtained via standard processes, for example by means of partial or complete hydrogenation, and the corresponding $R_{52}ZC(O)$haloalkenyl or $R_{52}ZC(O)$haloalkyl derivatives of the formula I via halogenation.

In accordance with reaction diagram 13, route b), the $R_{52}ZC(O)$haloalkyl derivatives of the formula $I_{50}$ can be prepared from the aniline derivatives of the formula $I_{44}$ in analogy to Organic Reactions 11, 189–260 (1960) via diazotization and Meerwein reaction. The corresponding $R_{52}ZC(O)$alkyl or $R_{52}ZC(O)$alkenyl derivatives of the formula I are obtained therefrom by known standard processes, for example hydrogenolysis or elimination of halogen.

The preparation of the benzofuran and dihydrobenzofuran rings of the compounds of the formula I in which W is a group

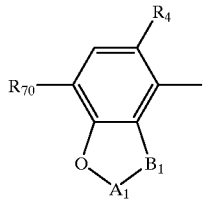

($W_3$) and $R_4$, $R_{70}$ and $A_1$–$B_1$ are as defined under formula I is illustrated in greater detail in reaction diagrams 14, 15 and 16 which follow.

Reaction diagram 14

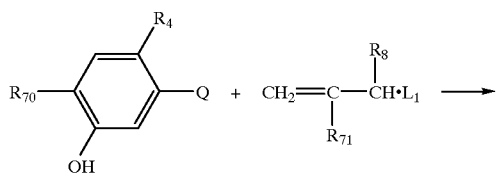

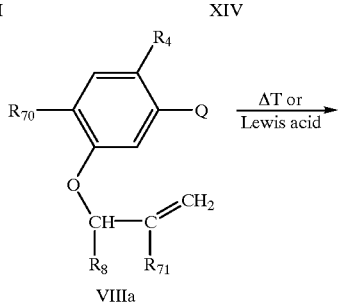

-continued

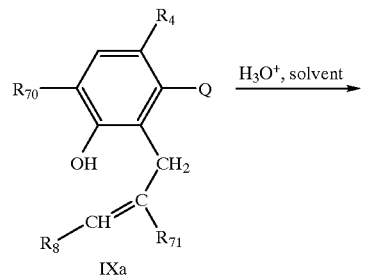

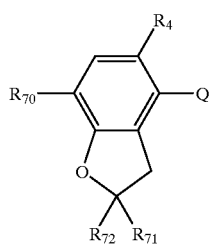

I ($R_{72}$ = -CH$_2$R$_8$)

Reaction diagram 15

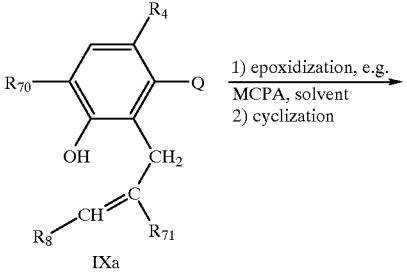

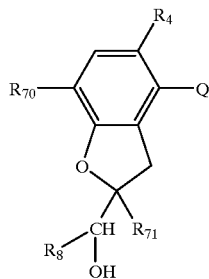

I ($R_{72}$ = -CH(OH)R$_8$)

Reaction diagram 16

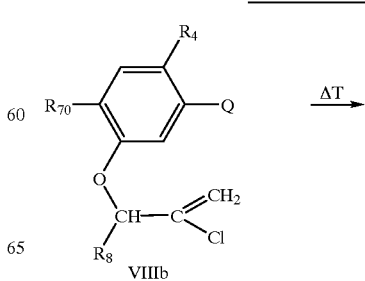

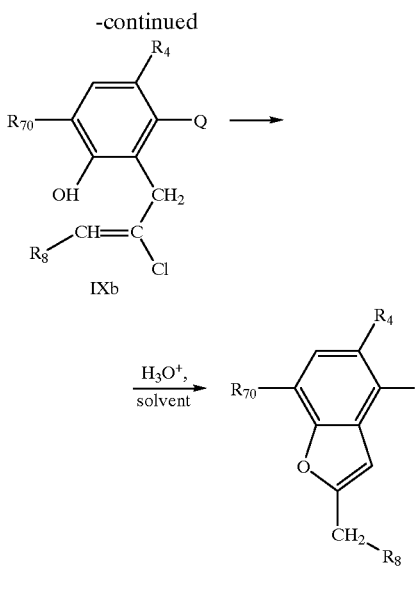

I ($R_{72}$ = —$CH_2R_8$)

In reaction diagrams 14,15 and 16, Q is the radical

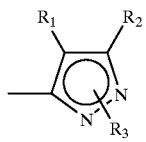

in which $R_1$ to $R_3$ are as defined under formula I.

The allyl ethers of the formula VIIIa can be obtained in accordance with reaction diagram 14, for example in analogy to EP-A-0 617 033 (page 3, lines 45 and 46) or U.S. Pat. No. 4,881,967 (column 11, lines 17–39) by means of reacting the compounds of the formula VII with an allyl derivative of the formula XIV, in which $L_1$ is a leaving group, e.g. halogen, in particular chlorine or bromine, with or without an inert organic solvent, for example acetone, acetonitrile or N,N-dimethylformamide, in the presence of a base, for example potassium carbonate.

The allylated phenol derivatives of the formula IXa are obtained by subjecting the corresponding allyl ethers of the formula VIIIa to a thermal rearrangement reaction. This rearrangement reaction (Claisen rearrangement) is effected for example in analogy to EP-A-0 617 033 (page 3, lines 17–44) or U.S. Pat. No. 4,881,967 (column 10, line 30 to end of column 10), with or without a solvent, for example toluene, xylenes, mesitylene or tetralin and tertiary amines, for example N,N-diethylaniline or mixtures thereof, at temperatures of from 20° to 300° C., preferably at from 100° C. to 250° C., for 0.5 to 48 hours. If desired, the rearrangement reaction may be carried out in a sealed pressurized container.

Alternatively, this rearrangement reaction may also be carried out in the presence of a Lewis acid catalyst, for example boron trichloride, in an inert solvent, for example dichloromethane, at temperatures of from 0° C. to 25° C., for example in analogy to U.S. Pat No. 4,881,967 (column 10, line 66 to end of column 10, and column 11, lines 1–7).

The subsequent cyclization reaction of the compounds of the formula IXa can be carried out by one or more methods, for example as described in U.S. Pat. No. 4,881,967 (column 8, lines 56 to end of column 8, and column 9, lines 1–3), but in particular with acid catalysis in an inert organic solvent, for example xylenes, in the presence of acids, for example p-toluene-sulfonic acid.

The preparation of the compounds of the formula I in which $R_{72}$ is hydroxy-$C_1$-$C_6$alkyl ($R_{72}$=—CH(OH)—$R_8$) is effected in accordance with reaction diagram 15 by epoxidizing the compound of the formula IXa, for example with m-chloroperbenzoic acid (MCPA), in the presence of an organic solvent and subsequently cyclizing the product in analogy to, for example, EP-A-0 617 033 (page 3, last section, and page 4, lines 1–50).

The allyl ethers of the formula VIIIb in reaction diagram 16 can be obtained for example in analogy to EP-A-0 561 319 from the corresponding phenols of the formula VII and the allyl derivatives of the formula XIV (reaction diagram 14; $R_{71}$=chlorine). The phenols of the formula IXb can be obtained by heating the allyl ethers of the formula VIIIb, in analogy to the procedure described in reaction diagram 14. This thermal rearrangement reaction is effected at temperatures of from 150° C. to 250° C. over 2 to 100 hours with or without an inert organic solvent.

Subsequent cyclization of the phenols of the formula IXb is expediently effected in the presence of an acid, e.g. mineral acids, for example hydrochloric acid, sulfuric acid or polyphosphoric acid, organic acids, for example p-toluenesulfonic acid or trifluoromethanesulfonic acid and carboxylic acids, for example formic acid, acetic acid or trifluoroacetic acid. The amount of acid used relative to phenols of the formula Vb is 1.1:1 up to 100:1.

The cyclization reaction is effected with or without a solvent, e.g. aromatic hydrocarbons, for example benzene or toluene, halogenated hydrocarbons, for example chloroform or carbon tetrachloride, mineral acids, for example hydrochloric acid or sulfuric acid, organic acids, for example acetic acid, and water. These solvents can also be employed in the form of a mixture.

This cyclization is successfully carried out at temperatures of from 0° C. to 100° C., preferably at from 5° C. to 80° C., over 0.5 to 24 hours.

All further functionalization reactions of the substituent $R_{72}$ (or —$CH_2R_8$ or —CH(OH)—$R_8$) in the 2-position of the benzofuranyl or dihydrobenzofuranyl increment to give the compounds of the formula I can be effected starting from the compounds of the formulae I in reaction diagrams 14, 15 and 16 in analogy to the procedure described in, for example, EP-A-0 617 033 (page 3, last section, up to page 8), EP-A-0 561 319 (page 3, last section, up to page 10) or U.S. Pat. No. 4,881,967 (columns 13 and 14).

The starting phenols of the formula VII (reaction diagram 14) can be obtained for example as shown in reaction diagram 17 from the corresponding methoxy- or benzyloxy-substituted derivatives of the formula $VII_1$ or $VII_2$, respectively, in which $R_4$ and $R_{70}$ are as defined under formula I and Q is the radical

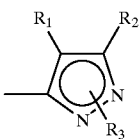

in which $R_1$ to $R_3$ are as defined under formula I.

Reaction diagram 17

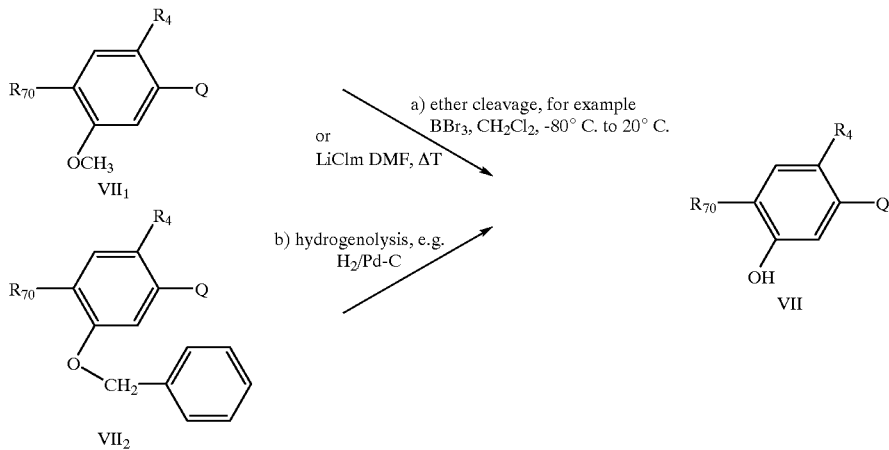

In accordance with this diagram, route a), the compounds of the formula VII$_1$ are subjected to ether cleavage by means of lithium chloride in N,N-dimethylformamide (DMF) at elevated temperature, for example as described in Synthesis 1989, 287, or by means of boron tribromide in dichloromethane at temperatures of from −80° C. to 20° C., as described, for example, in Org. Synth., Collect. Vol. V, 412, 1973, or, in accordance with route b), the compounds of the formula VII$_2$ are subjected to hydrogenolysis by means of hydrogen in the presence of a catalyst, for example palladium on charcoal, as described, for example, in J. Am. Chem. Soc. 93, 746 (1971).

The compounds of the formula VII$_1$ and VII$_2$ in reaction diagram 17 can be prepared by standard methods, for example as described in U.S. Pat. No. 4,452,981 and EP-A-0 061 741, from the known phenols of the formula VII$_3$

(VII$_3$)

in which R$_4$ and R$_{70}$ are as defined under formula I by means of nitrating the benzene ring and methylating or benzylating, respectively, the phenol function and subsequently reducing the nitro group to give the corresponding aniline derivative of the formula VII$_4$

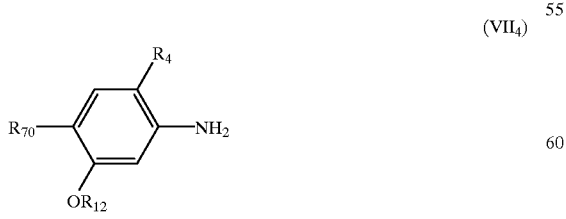

(VII$_4$)

in which R$_4$ and R$_{70}$ have the abovementioned meanings and R$_{12}$ is methyl or benzyl and subsequently constructing the pyrazole ring as described above.

The starting compounds of the formula XIV in reaction diagram 14 are known or can be prepared by disclosed processes.

A large number of known standard processes is available for the preparation of all other compounds of the formula I (W=W$_3$; R$_{72}$) which are substituted in the 2-position of the benzofuranyl or dihydrobenzofuranyl ring, for example alkylation, halogenation, acylation, amidation, oximation, oxidation and reduction, the choice of the suitable preparation process depending on the properties (reactivities) of the substituents in the intermediates in question.

The intermediates of the formula V$_0$

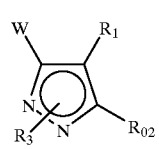

(V$_0$)

in which R$_1$, R$_3$ and W are as defined under formula I and R$_{02}$ is HOC(O)—, OHC—, C$_1$-C$_4$alkoxycarbonyl, C$_3$— or C$_4$alkenyloxycarbonyl, benzyloxycarbonyl, (C$_1$-C$_4$alkoxy)$_2$CH—, (C$_1$-C$_4$alkyl)-O—N=CH—, (C$_1$-C$_4$alkylsolfonyl)-O—N=CH—, (C$_1$-C$_4$haloalkylsulfonyl)-O—N=CH—, (C$_1$-C$_4$alkoxycarbonyl)-O—N=CH—, (C$_1$-C$_4$haloalkoxycarbonyl)-O—N=CH—, amino, ClC(O)— or H$_2$NC(O)— are novel. They represent important intermediates for the synthesis of the compounds of the formula I. The invention thus also relates to these compounds, with the exception of the compounds of the formulae

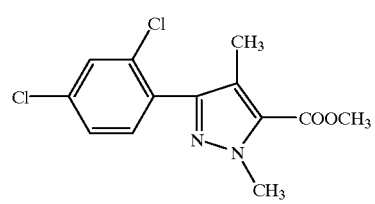

and

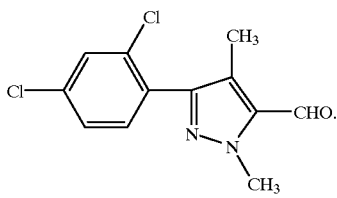

The end products of the formula I can be isolated in the customary manner by concentrating or evaporating the solvent and purified by recrystallization or trituration of the solid residue in solvents in which they are not readily soluble, such as ethers, aromatic hydrocarbons or chlorinated hydrocarbons, by distillation or by means of column chromatography and a suitable eluent.

Those skilled in the art will furthermore know in which sequence certain reactions, for example in reaction diagrams 1, 12 and 14, are to be carried out expediently to avoid secondary reactions which may occur.

Unless a target-orientated synthesis is carried out for isolating pure isomers, the product may be obtained in the form of a mixture of two or more isomers. The isomers can be separated by methods known per se.

Suitable application methods for the use according to the invention of the compounds of the formula I or compositions comprising them are all those which are conventionally used in agriculture, for example pre-emergence application, post-emergence application and seed dressing, and also various methods and techniques, for example the controlled release of active ingredient. To this end, the dissolved active ingredient is applied to mineral carriers for granules or polymerized granules (urea/formaldehyde) and dried. If desired, a coating can additionally be applied (coated granules) which allows controlled release of the active ingredient over a specific period.

The compounds of the formula I can be employed in unaltered form, i.e. as obtained in synthesis, but they are preferably processed in the customary manner together with the auxiliaries conventionally used in the art of formulation, for example to give emulsifiable concentrates, directly sprayable or dilutable solutions, dilute emulsions, wettable powders, soluble powders, dusts, granules or microcapsules. The application methods, such as spraying, atomizing, dusting, wetting, spreading or pouring and also the type of the compositions are chosen to suit the intended aims and the prevailing circumstances.

The formulations, i.e. the compositions, preparations or products comprising the active ingredient of the formula I or at least one active ingredient of the formula I and, as a rule, one or more solid or liquid formulation auxiliaries, are prepared in the known manner, for example by intimately mixing and/or grinding the active ingredients with the formulation auxiliaries, for example solvents or solid carriers. Furthermore, surface-active compounds (surfactants) may additionally be used when preparing the formulations.

Suitable solvents can be: aromatic hydrocarbons, preferably the fractions $C_8$ to $C_{12}$, for example xylene mixtures or substituted naphthalenes, phthalic esters such as dibutyl phthalate or dioctyl phthalate, aliphatic hydrocarbons such as cyclohexane or paraffins, alcohols and glycols, and their ethers and esters such as ethanol, ethylene glycol, ethylene glycol monomethyl ether or ethylene glycol monoethyl ether, ketones such as cyclohexanone, strongly polar solvents such as N-methyl-2-pyrrolidone, dimethyl sulfoxide or N,N-dimethylformamide, and epoxidized or unepoxidized vegetable oils, such as epoxidized coconut oil or soya oil, or water.

Solid carriers which are used for example for dusts and dispersible powders are, as a rule, ground natural minerals such as calcite, talc, kaolin, montmorillonite or attapulgite. To improve the physical properties of the formulation, it is also possible to add highly disperse silica or highly disperse absorptive polymers. Possible particulate, adsorptive carriers for granules are porous types, for example pumice, brick grit, sepiolite or bentonite, and suitable non-sorptive carrier materials are, for example, calcite or sand. In addition, a large number of pregranular materials of inorganic or organic nature, such as, in particular dolomite or comminuted plant residues, may be used.

Suitable surface-active compounds are, depending on the type of the active ingredient of the formula I to be formulated, non-ionic, cationic and/or anionic surfactants and surfactant mixtures which have good emulsifying, dispersing and wetting properties.

Suitable anionic surfactants can be not only so-called water-soluble soaps, but also water-soluble synthetic surface-active compounds.

Soaps which may be mentioned are the alkali metal salts, alkaline earth metal salts or substituted or unsubstituted ammonium salts of higher fatty acids ($C_{10}$–$C_{22}$), for example the sodium or potassium salts of oleic or stearic acid or of natural fatty acid mixtures which can be obtained, for example, from coconut or tallow oil. Mention must also be made of the fatty acid methyltaurinates.

However, so-called synthetic surfactants are used more frequently, in particular fatty alcohol sulfonates, fatty alcohol sulfates, sulfonated benzimidazole derivatives or alkylarylsulfonates.

As a rule, the fatty alcohol sulfonates or fatty alcohol sulfates are present in the form of alkali metal salts, alkaline earth metal salts or substituted or unsubstituted ammonium salts and have an alkyl radical of 8 to 22 C atoms, alkyl also including the alkyl moiety of acyl radicals, for example the sodium or calcium salt of lignosulfonic acid, of the dodecylsulfuric ester or of a fatty alcohol sulfate mixture prepared from natural fatty acids. This section also includes the salts of the sulfuric esters and sulfonic acids of fatty alcohol/ ethylene oxide adducts. The sulfonated benzimidazole derivatives preferably contain 2 sulfo groups and one fatty acid radical of 8–22 C atoms. Examples of alkylarylsulfonates are the sodium, calcium or triethanolamine salts of dodecylbenzenesulfonic acid of dibutylnaphthalene-sulfonic acid or of a naphthalenesulfonic acid/formaldehyde condensate.

Other possible substances are suitable phosphates, for example salts of the phosphoric ester of a p-nonylphenol, (4–14)ethyleneoxide adduct, or phospholipids.

Suitable non-ionic surfactants are mainly polyglycol ether derivatives of aliphatic or cycloaliphatic alcohols, saturated or unsaturated fatty acids and alkylphenols which can contain 3 to 30 glycol ether groups and 8 to 20 carbon atoms in the (aliphatic) hydrocarbon radical and 6 to 18 carbon atoms in the alkyl radical of the alkylphenols.

Other suitable non-ionic surfactants are the water-soluble polyethylene oxide adducts with polypropylene glycol, ethylenediaminopolypropylene glycol and alkylpolypropylene glycol which have 1 to 10 carbon atoms in the alkyl chain and contain 20 to 250 ethylene glycol ether groups and 10 to 100 propylene glycol ether groups. The abovementioned compounds normally contain 1 to 5 ethylene glycol units per polypropylene glycol unit.

Examples which may be mentioned of non-ionic surfactants are nonylphenylpolyethoxyethanols, castor oil polyglycol ethers, polypropylene/polyethylene oxide adducts, tributylphenoxypolyethoxyethanol, polyethylene glycol and octylphenoxypolyethoxyethanol.

Also suitable are fatty acid esters of polyoxyethylene sorbitan, such as polyoxyethylene sorbitan trioleate.

The cationic surfactants are, in particular, quaternary ammonium salts which contain, as N-substituents, at least one alkyl radical of 8 to 22 C atoms and as further substituents lower halogenated or unhalogenated alkyl, benzyl or lower hydroxyalkyl radicals. The salts are preferably in the form of halides, methylsulfates or ethylsulfates, for example stearyltrimethylammonium chloride or benzyldi(2-chloroethyl)ethylammonium bromide.

The surfactants conventionally used in the art of formulation, which may also be used in the compositions according to the invention, are described, inter alia, in "Mc Cutcheon's Detergents and Emulsifiers Annual" MC Publishing Corp., Ridgewood N.J., 1981, Stache, H., "Tensid-Taschenbuch" [Surfactant Guide], Carl Hanser Verlag, Munich/Vienna, 1981, and M. and J. Ash, "Encyclopedia of Surfactants", Vol I–III, Chemical Publishing Co., New York, 1980–81.

The herbicidal formulations comprise, as a rule, 0.1 to 99% by weight, in particular 0.1 to 95% by weight, of herbicide, 1 to 99.9% by weight, in particular 5 to 99.8% by weight, of a solid or liquid formulation auxiliary and 0 to 25% by weight, in particular 0.1 to 25% by weight, of a surfactant.

While concentrated compositions are more preferred as commercially available goods, the end user uses, as a rule, dilute compositions.

The compositions can also comprise other additives such as stabilizers, for example epoxidized or unepoxidized vegetable oils (epoxidized coconut oil, rapeseed oil or soya oil), antifoams for example silicone oil, preservatives, viscosity regulators, binders, tackifiers and fertilizers or other active ingredients.

Preferred formulations are composed in particular as follows:
(%=per cent by weight)

| Emulsifiable concentrates: | |
| --- | --- |
| Active ingredient: | 1 to 90%, preferably 5 to 50% |
| Surfactant: | 5 to 30%, preferably 10 to 20% |
| Solvent: | 15 to 94%, preferably 70 to 85% |
| Dusts: | |
| Active ingredient: | 0.1 to 50%, preferably 0.1 to 1% |
| Solid carrier: | 99.9 to 90%, preferably 99.9 to 99% |
| Suspension concentrates: | |
| Active ingredient: | 5 to 75%, preferably 10 to 50% |
| Water: | 94 to 24%, preferably 88 to 30% |
| Surfactant: | 1 to 40%, preferably 2 to 30% |
| Wettable powders: | |
| Active ingredient: | 0.5 to 90%, preferably 1 to 80% |
| Surfactant: | 0.5 to 20%, preferably 1 to 15% |
| Solid carrier: | 5 to 95%, preferably 15 to 90% |
| Granules: | |
| Active ingredient: | 0.1 to 30%, preferably 0.1 to 15% |
| Solid carrier: | 99.5 to 70%, preferably 97 to 85% |

As a rule, the active ingredients of the formula I can be applied successfully to the plant or its environment at rates of application of 0.001 to 4 kg/ha, in particular 0.005 to 2 kg/ha, either as a mixture composed of the isomers Ia and Ib or as pure isomers Ia or Ib. The dosage required for the desired action can be determined by experiments. It depends on the type of action, the developmental stage of the crop plant and of the weed and on the application (location, timing, method) and it can vary within wide ranges due to these parameters.

The compounds of the formula I and, as a rule, especially the isomers of the formula Ia are distinguished by herbicidal and growth-inhibiting properties which make them suitable for use in crops of useful plants, in particular in cereals, cotton, soya, sugar beet, sugar cane, plantations, oilseed rape, maize and rice, and for non-selective weed control ('total vegetation mangement', TVM).

Crops are also to be understood as including those which have been made tolerant to herbicides or classes of herbicides by conventional plant-breeding or genetic engineering methods. The weeds to be controlled can be not only monocotyledoneous, but also dicotyledoneous weeds, for example Stellaria, Nasturtium, Agrostis, Digitaria, Avena, Setaria, Sinapis, Lolium, Solanum, Phaseolus, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, Ipomoea, Chrysanthemum, Galium, Viola and Veronica.

The examples which follow illustrate the invention in greater detail without imposing any limitation.

Preparation Examples

EXAMPLE H1

3-(4-chloro-2-fluoro-5-methoxyphenyl)-4-methyl-5-methoxycarbonyl-[1H]-pyrazole (Comp. No. $V_1.358$)

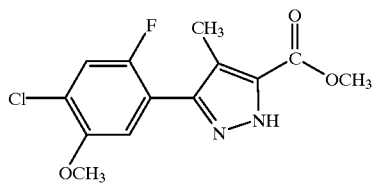

13.0 g of 1-(4-chloro-2-fluoro-5-methoxyphenyl)-1-propanone and 7.4 g of dimethyl oxalate are introduced into 50 ml of absolute tetrahydrofuran. 12 ml of a 5.4-molar solution of sodium methoxide in methanol are added dropwise with stirring at 22° C. in the course of 10 minutes, and stirring is subsequently continued for 1 hour. Thin-layer analysis (silica gel 60 $F_{254}$, n-hexane/ethyl acetate/glacial acetic acid=20/20/1 (v/v/v), UV) of a worked-up sample shows that all of the starting material has reacted.

The reaction mixture is poured into a mixture of ice and 2-molar hydrochloric acid and extracted with diethyl ether. The ether phase is washed with water and saline, dried over sodium sulfate, filtered and concentrated in vacuo. This gives 18.0 9 of a yellow solid which is introduced into 80 ml of glacial acetic acid. Thereupon, 3.2 ml of hydrazine hydrate are added slowly, using a syringe (exothermic). The mixture is subsequently refluxed gently overnight with stirring. The reaction mixture is evaporated to dryness in vacuo, and the residue is diluted with carbon tetrachloride and reconcentrated. The residue obtained is applied to 40 g of silica gel from ethyl acetate. After the silica gel had been applied to a flash chromatography column, it is eluted with a mixture of n-hexane/ethyl acetate/glacial acetic acid=100/50/1 (v/v/v). This gives 3.2 g of the desired compound as a yellow solid. Mass spectrum: [M⁺]298, 266, 210.

EXAMPLE H2

3-(4-chloro-2-fluoro-5-methoxyphenyl)-4-methyl-5-methoxycarbonyl-1-methyl-[1H]-pyrazole

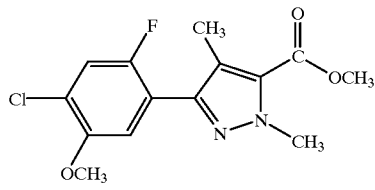

(Comp. No. V$_1$.071)

4.0 g of 3-(4-chloro-2-fluoro-5-methoxyphenyl)-4-methyl-5-methoxycarbonyl-[1H]-pyrazole (Example H1) are dissolved in 15 ml of dry N-methylpyrrolidone. After 5.6 g of potassium carbonate have been added, the mixture is stirred, a solution of 2.1 g of methyl iodide in 2 ml of N-methylpyrrolidone is slowly added dropwise at 22° C., and stirring is continued for 4 hours at the same temperature. Thin layer analysis (silica gel 60 F$_{254}$, toluene/glacial acetic acid 10/1 (v/v), UV) of a worked-up sample shows that starting material is no longer present. The reaction mixture is diluted with water and extracted with diethyl ether. The combined organic phases are washed with water, dried over sodium sulfate and filtered, and the filtrate together with 8 g of silica gel is evaporated to dryness in vacuo. After the silica gel has been applied to a flash chromatography column, it is eluted with a mixture of n-hexane/ethyl acetate=2/1 (v/v). This gives 2.6 g of the desired compound of m.p. 135–137° C.

1.35 g of the regioisomeric 5-(4-chloro-2-fluoro-5-methoxyphenyl)-4-methyl-3-methoxycarbonyl-1-methyl-[1H]-pyrazole of m.p. 99–1 03° C. are eluted in the next fraction as byproduct.

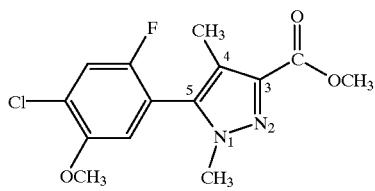

EXAMPLE H3

3-(4-chloro-2-fluoro-5-methoxyphenyl)-4-methyl-5-carboxyl-1-methyl-[1H]-pyrazole

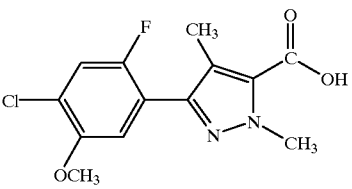

(Comp. No. V$_2$.071)

2.3 g of 3-(4-chloro-2-fluoro-5-methoxyphenyl)-4-methyl-5-methoxycarbonyl-1-methyl-[1H]-pyrazole (Example H2) are introduced at 22° C. into 20 ml of dioxane, and 4 ml of a 3-molar aqueous sodium hydroxide solution is then added dropwise. The reaction solution is then stirred overnight and subsequently acidified with dilute hydrochloric acid and extracted with ethyl acetate. The combined organic phases are washed with water and saline, dried over sodium sulfate and filtered, and the filtrate is evaporated to dryness in vacuo. This gives 2.2 g of the desired compound as white solid.

¹H NMR: (DMSO-D$_6$): acid proton in offset; 7.55 ppm (1H, d); 7.11 ppm (1H, d); 4.10 ppm (3H, s); 3.86 ppm (3H, s).

EXAMPLE H4

3-(4-chloro-2-fluoro-5-methoxyphenyl)-4-methyl-5-carbamoyl-1-methyl-[1H]-pyrazole

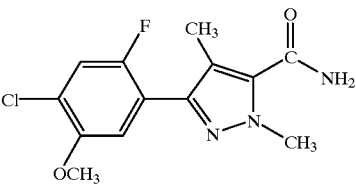

(Comp. No. II$_1$.071)

2,2 g of 3-(4-chloro-2-fluoro-5-methoxyphenyl)-4-methyl-5-carboxyl-1-methyl-[1H]-pyrazole (Example H3) are introduced into 10 ml of 1,3-dichloroethane. First, a few drops of dimethylformamide and then 1.3 ml of thionyl chloride are added. The suspension is refluxed gently overnight, with stirring. The yellow solution is subsequently evaporated in vacuo, treated with 20 ml of carbon tetrachloride and reconcentrated. This gives 2.48 g of a yellow solid which is dissolved in 3 ml of tetrahydrofuran. This solution is added dropwise at 22° C. to 20 ml of a 30% aqueous ammonia solution, and stirring is continued for 2 hours. The resulting suspension is extracted with ethyl acetate, and the combined organic phases are washed with water and saline, dried over sodium sulfate, filtered and evaporated to dryness in vacuo. This gives 2.0 g of the desired compound as a pale brown solid of m.p. 224–226° C.

EXAMPLE H5

3-(4-chloro-2-fluoro-5-methoxyphenyl)-4-methyl-5-cyano-1-methyl-[1H]-pyrazole

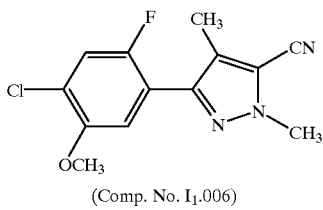

(Comp. No. I₁.006)

2.0 g of 3-(4-chloro-2-fluoro-5-methoxyphenyl)-4-methyl-5-carbamoyl-1-methyl-[1H]-pyrazole (Example H4) are introduced into 10 ml of dioxane. After 1.3 ml of pyridine have been added, the mixture is cooled in an ice-bath, and 1.4 ml of trifluoroacetic anhydride are added dropwise using a syringe, with stirring. Stirring is continued for 1hour with cooling. Thin-layer analysis (silica gel 60 F₂₅₄, n-hexane/ethyl acetate 1/1 (v/v), UV) of a worked-up sample shows that all of the starting material has been reacted. The reaction mixture is diluted with ethyl acetate and extracted in succession with dilute hydrochloric acid, dilute sodium bicarbonate solution and saline. The organic phase is dried over sodium sulfate and filtered, and the filtrate is evaporated to dryness in vacuo. This gives 1.8 g of the desired product as a colourless solid of m.p. 155–156° C.

The regioisomeric 5-(4-chloro-2-fluoro-5-methoxyphenyl)-4-methyl-3-methoxycarbonyl-1-methyl-[1H]-pyrazole (Example H2) can also be converted into the corresponding cyano derivative in an analogous manner:

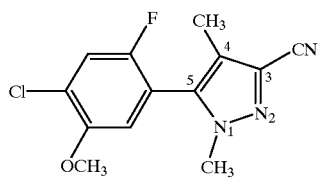

EXAMPLE H6

3-(4-chloro-2-fluoro-5-hydroxyphenyl)-4-methyl-5-cyano-1-methyl-[1H]-pyrazole

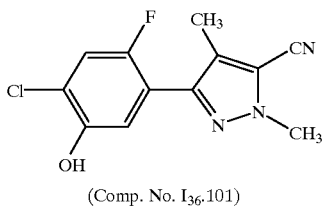

(Comp. No. I₃₆.101)

3.04 g of lithium chloride.hydrate (LiCl.H₂O) are added at 22° C. to 2.8 g of 3-(4-chloro-2-fluoro-5-methoxyphenyl)-4-methyl-5-cyano-1-methyl-[1H]-pyrazole (Example H5) in 90 ml of N,N-dimethylformamide. The reaction mixture is heated to reflux temperature and held for 4 days at this temperature, during which process some of the DMF (approx. 5 ml) is distilled off. The resulting reaction mixture is subsequently poured into dilute aqueous hydrochloric acid and extracted with dichloromethane. The organic phase which has been separated off is washed with water and saline, dried over anhydrous sodium sulfate and evaporated in vacuo. The residue obtained is purified over a silica gel column (eluent: ethyl acetate/hexane 1/1). This gives the desired product in a yield of 1.61 g (60.9% of theory).

1.92 g (68.3% of theory) of the desired 3-(2,4-dichloro-5-hydroxyphenyl)-4-methyl-5-cyano-1-methyl-[1H]-pyrazole (Comp. No. I₃₆.103) are obtained in an analogous manner from 2.96 g of 3-(2,4-dichloro-5-methoxyphenyl)-4-methyl-5-cyano-1-methyl-[1H]-pyrazole.

EXAMPLE H7

3-(4-chloro-2-fluoro-5-propargyloxyphenyl)-4-methyl-5-cyano-1-methyl-[1H]pyrazole

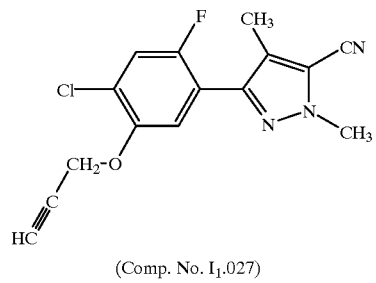

(Comp. No. I₁.027)

1.33 g of 3-(4-chloro-2-fluoro-5-hydroxyphenyl)-4-methyl-5-cyano-1-methyl-[1H]-pyrazole (Example H6) are dissolved in 25 ml of acetone, and 1.38 g of potassium carbonate are added. The reaction mixture is stirred for 10 minutes at 22° C., and 0.89 g (0.56 ml) of propargyl bromide is then added dropwise with stirring, and stirring is continued for 5 hours at this temperature. The solvent is subsequently distilled off in vacuo and the residue is taken up in diethyl ether. After the etheric solution has been washed with water and saline and the solvent evaporated off, the desired product is obtained in a yield of 1.36 g (89.9% of theory).

1.38 g (86.4% of theory) of the desired 3-(2,4-dichloro-5-propargyloxyphenyl)-4-methyl-5-cyano-1-methyl-[1H]-pyrazole (Comp. No. I₃.027) are obtained in a similar manner from 1.41 g of 3-(2,4-dichloro-5-hydroxyphenyl)-4-methyl-5-cyano-1-methyl-[1H]-pyrazole.

EXAMPLE H8

3-(4-chloro-2-fluoro-5-iodophenyl)-4-methyl-5-cyano-1-methyl-[1H]-pyrazole

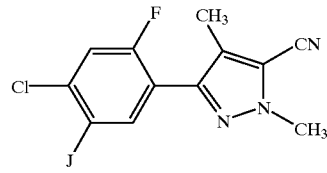

(Comp. No. I₃₆.109)

5.86 g of isoamyl nitrite are added dropwise at a temperature of below 15° C. to a solution of 2.64 g of 3-(5-amino-4-chloro-2-fluoro-phenyl)-4-methyl-5-cyano-1-methyl-[1H]-pyrazole in 54 g (16 ml) of diiodomethane. The reaction mixture is stirred for 14 hours at 22° C., and excess diiodomethane is evaporated in vacuo. All the diiodomethane is subsequently distilled off at 70–75° C./14 torr, and the crude product is purified over a silica gel column (eluent: ethyl acetate/hexane 1/5). The desired product is obtained in a yield of 1.88 g (50.2% of theory).

2.04 g (52.1% of theory) of the desired 3-(2,4-dichloro-5-iodophenyl)-4-methyl-5-cyano-1-methyl-[1H]-pyrazole (Comp. No. I$_{36}$.111) are obtained in an analogous manner from 2.81 g of 3-(5-amino-2,4-dichlorophenyl)-4-methyl-5-cyano-1-methyl-[1H]-pyrazole.

EXAMPLE H9

3-(4-chloro-2-fluoro-5-(2-chloro-2-carbethoxy)prop-1-yl-phenyl)-4-methyl-5-cyano-1-methyl-[1H]-pyrazole

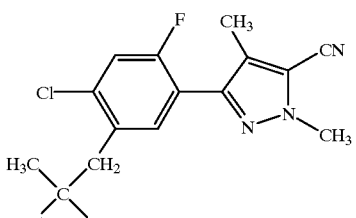

(Comp. No. I$_1$.118)

2.2 g of copper(II) chloride.hydrate, which had previously been dried in a microwave oven, is added to 50 ml of acetonitrile. To this stirred suspension there are first added 24.5 g (26.7 ml) of ethyl methacrylate. The mixture is then cooled to −5° C., 1.66 g of tert-butyl nitrite are added dropwise, and 2.84 g of 3-(5-amino-4-chloro-2-fluorophenyl)-4-methyl-5-cyano-1-methyl-[1H]-pyrazole, dissolved in 70 ml of acetonitrile, are then added in the course of ½ to 1 hour at −5° C. to 0° C. This reaction mixture is stirred for 1 hour at 0° C. and subsequently for a further hour at 22° C., the solvent is evaporated, and the residue is dissolved in diethyl ether. This etheric solution is washed with water and then with saturated aqueous sodium bicarbonate solution and concentrated, and the residue is purified by silica gel chromatography (eluent: ethyl acetate/hexane 1/9). This gives 2.16 g (50.5% of theory) of the desired compound.

EXAMPLE H10

3-(4-chloro-2-fluoro-5-[(N,N-bisethanesulfonyl)amino]phenyl)-4-methyl-5-cyano-1-methyl-[1H]-pyrazole

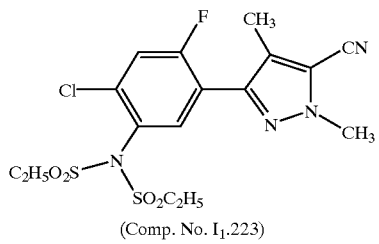

(Comp. No. I$_1$.223)

2.12 g of 3-(5-amino-4-chloro-2-fluorophenyl)-4-methyl-5-cyano-1-methyl-[1 H]-pyrazole are dissolved in 25 ml of dichloromethane, and 2.19 g (3.01 ml) of triethylamine are then added. This mixture is cooled to −15° C., and 2.37 g (1.74 ml) of ethanesulfonyl chloride are added dropwise. The mixture is subsequently slowly heated to 22° C., washed with dilute aqueous hydrochloric acid, dried over sodium sulfate and concentrated. The crude product obtained is purified by silica gel chromatography (eluent: ethyl acetate/hexane 1/2), yielding 3.05 g (85% of theory) of the desired product.

EXAMPLE H11

3-(4-chloro-2-fluoro-5-ethanesulfonamidophenyl)-4-methyl-5-cyano-1-methyl-[1H]-pyrazole

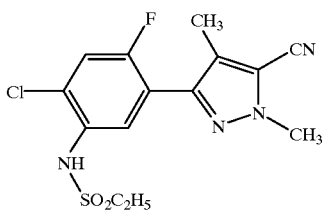

(Comp. No. I$_1$.220)

6.5 ml of 2N sodium hydroxide solution are added dropwise to a solution of 2.93 g of 3-(4-chloro-2-fluoro-5-[(N,N-bisethanesulfonyl)amino]phenyl)-4-methyl-5-cyano-1-methyl-[1H]-pyrazole (Example H10) in 15 ml of dioxane and the mixture is stirred for 1 hour at 22° C. The mixture is subsequently poured into ice/water mixture and extracted with ethyl acetate. The combined organic phases are washed with water and dried over sodium sulfate. After the mixture has been filtered and concentrated, 2.31 g (90.6% of theory) of the desired product are obtained.

EXAMPLE H12

3-(4-chloro-2-fluoro-5-[(N-allyl-N-ethanesulfonyl)amino]phenyl)-4-methyl-5-cyano-1-methyl-[1H]-pyrazole (Comp. No. I$_1$.077)

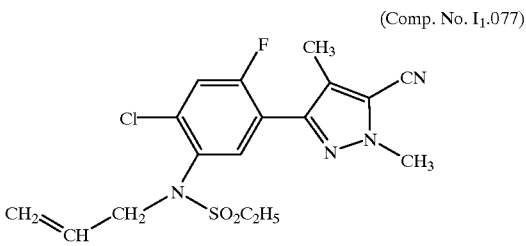

0.63 g of potassium carbonate is added to a solution of 1.08 g of 3-(4-chloro-2-fluoro-5-ethanesulfonamidophenyl)-4-methyl-5-cyano-1-methyl-[1H]-pyrazole (Example H11) in 30 ml of tetrahydrofuran (THF). 0.55 g of allyl bromide is added dropwise to this suspension, with stirring, and the mixture is stirred first overnight at 22° C. and subsequently for another 8 hours at 40°–50° C. The solvent is evaporated and the resulting residue is purified over silica gel (eluent: ethyl acetate/hexane 1/2). This gives 1.19 g (99.5% of theory) of the desired product.

EXAMPLE H13

3-(4-chloro-2-fluoro-5-carbethoxyphenyl)-4-methyl-5-cyano-1-methyl-[1H]-pyrazole (Comp. No. $I_1.134$)

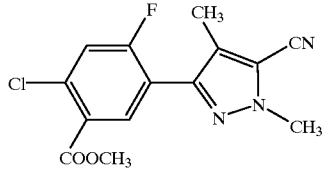

5.2 g of 3-(4-chloro-2-fluoro-5-iodophenyl)-4-methyl-5-cyano-1-methyl-[1H]-pyrazole (Example H8), 60 ml of methanol, 2.8 g of triethylamine and 0.4 g of bis (triphenylphosphine)palladium(II) dichloride ($PdCl_2(PPh_3)_2$) are placed into a 100 ml pressurized container and stirred for 16 hours at a temperature of 100° C. and a carbon monoxide pressure of 10 megapascal (Mpa). The solvent is subsequently evaporated and the crude product which remains is purified over a silica gel column (eluent: ethyl acetate/hexane 1/5). This gives 3.1 g (69.3% of theory) of the desired product.

EXAMPLE H14

3-(4-chloro-2-fluoro-5-carboxyphenyl)-4-methyl-5-cyano-1-methyl-[1H]-pyrazole (Comp. No. $I_1.130$)

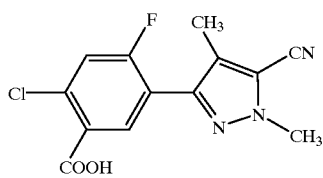

3.1 g of 3-(4-chloro-2-fluoro-5-carbethoxyphenyl)-4-methyl-5-cyano-1-methyl-[1H]-pyrazole (Example H13) are dissolved in 22 ml of dioxane, and 10 ml of 2N aqueous sodium hydroxide solution are added dropwise at 22° C. The mixture is stirred until the reaction is complete, the solvent is evaporated, the resulting residue is dissolved in water and the solution is brought to pH 1 using hydrochloric acid. The precipitate formed is filtered off and dried. This gives the desired product in a yield of 2.63 g (89.8% of theory).

EXAMPLE H15

3-(4-chloro-2-fluorophenyl)-4-methyl-5-cyano-1-methyl-[1H]-pyrazole (isomer A) and 3-(4-chloro-2-fluorophenyl)-4-cyano-1,5-dimethyl-[1H]-pyrazole (isomer B)

(Comp. No. $I_1.001$)

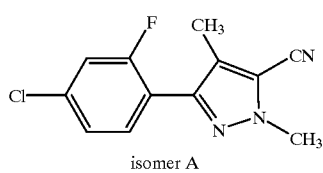

isomer A and

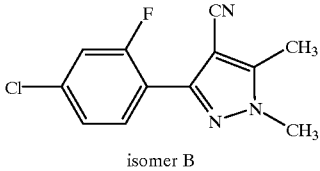

isomer B 16.3 g of 4-chloro-2-fluorophenylmethylhydrazonoyl bromide.hydrobromide are added to 275 ml of toluene and the mixture is stirred. 8.92 g of 2-bromo-2-butenonitrile are added to this stirred suspension, followed by the dropwise addition of 8.5 ml of triethylamine (exothermic). Stirring of the suspension is continued for 2 hours at 60° C. The mixture is cooled and then filtered, the solids are washed with toluene and the toluene phase is extracted with 1N aqueous hydrochloric acid, then washed with water and saline and dried over sodium sulfate. The solvent is evaporated and the resulting crude product is purified over a silica gel column (eluent: ethyl acetate/hexane 1/4). The products obtained are the desired isomer A in a yield of 7.68 g (65.4% of theory) and isomer B in a yield of 0.91 g (7.7% of theory).

EXAMPLE H16

3-(4-chloro-2-fluoro-5-(carboxylic acid-1-ethoxycarbonyl-1-methylethylester)phenyl)-4-methyl-5-cyano-1-methyl-[1H]-pyrazole (Comp. No. $I_1.159$)

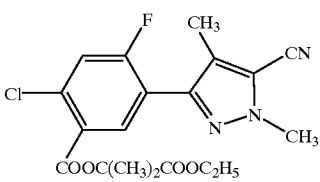

2 drops of N,N-dimethylformamide (DMF) and then, dropwise, 1.01 g of oxalyl chloride are added to a stirred solution of 1.17 g of 3-(4-chloro-2-fluoro-5-carboxyphenyl)-4-methyl-5-cyano-1-methyl-[1H]-pyrazole (Example H14) in 30 ml of dry dichloromethane. This mixture is stirred for 1hour at 22° C. and subsequently refluxed for 10 minutes. The solvent and excess oxalyl chloride are evaporated and the resulting residue is dissolved in 30 ml of dry dichloromethane. A solution of 0.605 g of ethyl 2-hydroxyisobutyrate in 8 ml of pyridine is added dropwise to this solution, and this mixture is stirred overnight at 22° C. The solvent is subsequently evaporated, the resulting residue is dissolved in ethyl acetate, and this solution is washed first with water and then with saline and dried over sodium sulfate. The solvent is evaporated and the crude product is purified over a silica gel column (eluent: ethyl acetate/hexane 1/8). The desired product is obtained in a yield of 1.06 g (65.4% of theory).

The compounds listed in the tables which follow can also be prepared in an analogous manner.

In Tables 1 to 6 and 8 to 10 which follow, certain structures $I_n$, $II_1$, $II_2$, $III_1$, $III_2$, $III_n$ or $V_n$, for example $I_1$ to $I_8$ in Table 1 or $I_{33}$ to $I_{35}$ in Table 5, which have the same variations of substitutents, for example $R_5$ and $R_6$ in Table 1 or $R_2$, $R_3$, $R_4$, $R_5$ and $R_{72}$ in Table 5, are combined for the sake of simplicity.

Thus, in the abovementioned tables, all structures $I_n$, or $II_1$, $II_2$, $III_1$, $III_2$, $III_n$ or $V_n$ which are mentioned in the captions of the tables where n=1 to 8 in the case of Table 1, are to be combined with the meanings mentioned in the tables. In Table 1, for example, $I_n.001$ discloses each of the 8 specific compounds $I_1.001$, $I_2.001$, $I_3.001$, $I_4.001$, $I_5.001$, $I_6.001$, $I_7.001$ and $I_8.001$ in which $R_5$ and $R_6$ are in each case chlorine or hydrogen.

TABLE 1

Compounds of the formulae $I_1$ to $I_8$

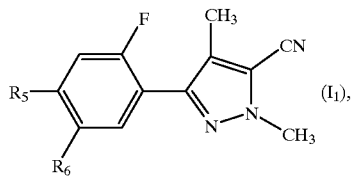

(I₁),

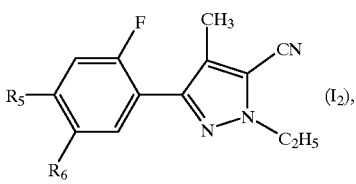

(I₂),

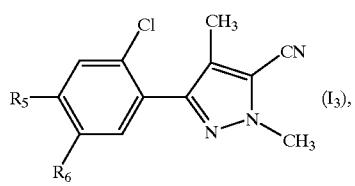

(I₃),

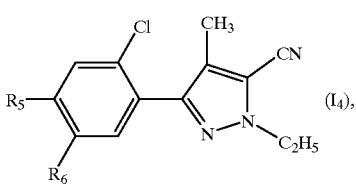

(I₄),

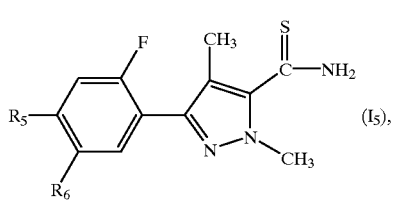

(I₅),

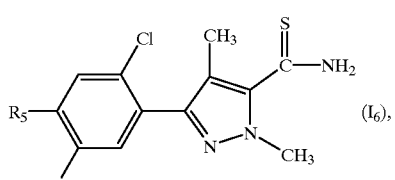

(I₆),

TABLE 1-continued

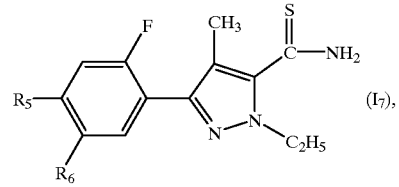

(I₇),

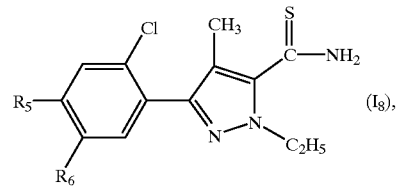

(I₈),

| Comp. No. $I_n$ n = 1–8 | $R_5$ | $R_6$ |
|---|---|---|
| 001 | Cl | H |
| 002 | Br | H |
| 003 | CN | H |
| 004 | I | H |
| 005 | CH₃ | H |
| 006 | Cl | OCH₃ |
| 007 | Br | OCH₃ |
| 008 | CN | OCH₃ |
| 009 | I | OCH₃ |
| 010 | CH₃ | OCH₃ |
| 011 | Cl | OCH₂CH₃ |
| 012 | Cl | OCH₂CH₂CH₃ |
| 013 | Cl | OCH(CH₃)₂ |
| 014 | Br | OCH(CH₃)₂ |
| 015 | Cl | OCH₂CHCH₂ |
| 016 | Br | OCH₂CHCH₂ |
| 017 | CH₃ | OCH₂CHCH₂ |
| 018 | CN | OCH₂CHCH₂ |
| 019 | Cl | OCH₂C(CH₃)CH₂ |
| 020 | Br | OCH₂C(CH₃)CH₂ |
| 021 | CH₃ | OCH₂C(CH₃)CH₂ |
| 022 | CN | OCH₂C(CH₃)CH₂ |
| 023 | Cl | OCH₂CClCH₂ |
| 024 | Br | OCH₂CClCH₂ |
| 025 | Cl | OCH(CH₃)CHCH₂ |
| 026 | CN | OCH(CH₃)CHCH₂ |
| 027 | Cl | OCH₂CCH |
| 028 | Br | OCH₂CCH |
| 029 | CN | OCH₂CCH |
| 030 | CH₃ | OCH₂CCH |
| 031 | Cl | OCH(CH₃)CCH |
| 032 | Br | OCH(CH₃)CCH |
| 033 | Cl | OCH₂C₆H₅ |
| 034 | Cl | OCH₂CH₂OCH₂CH₃ |
| 035 | Br | OCH₂CH₂OCH₂CH₃ |
| 036 | CN | OCH₂CH₂OCH₂CH₃ |
| 037 | CH₃ | OCH₂CH₂OCH₂CH₃ |
| 038 | Cl | OCH₂CH₂OCH₂CH₂OCH₃ |
| 039 | Br | OCH₂CH₂OCH₂CH₂OCH₃ |
| 040 | CN | OCH₂CH₂OCH₂CH₂OCH₃ |
| 041 | CH₃ | OCH₂CH₂OCH₂CH₂OCH₃ |
| 042 | Cl | OCH(CH₃)CH₂OCH₃ |
| 043 | Cl | OCH₂COOH |
| 044 | Cl | OCH₂COOCH₂CH₃ |
| 045 | Cl | OCH(CH₃)COOH |
| 046 | Br | OCH(CH₃)COOH |
| 047 | Cl | OCH(CH₃)COOCH₃ |
| 048 | Cl | OCH(CH₃)COOCH₂CH₃ |
| 049 | Cl | OCH(CH₃)COOCH₂C₆H₅ |
| 050 | Br | OCH(CH₃)COOCH(CH₃)₂ |
| 051 | CN | OCH(CH₃)COOCH₂CH₃ |
| 052 | Cl | OCH(C₆H₅)COOH |
| 053 | Cl | OCH(C₆H₅)COOCH₃ |
| 054 | Br | OCH(C₆H₅)COOCH₂CH₃ |

TABLE 1-continued

| | | |
|---|---|---|
| 055 | Cl | OC(CH₃)₂COOH |
| 056 | Cl | OC(CH₃)₂COOCH₂CH₃ |
| 057 | Br | OCH₂CH₂COOH |
| 058 | Br | OCH₂CH₂COOCH₃ |
| 059 | Cl | SCH₃ |
| 060 | Cl | SCH₂CHCH₂ |
| 061 | Cl | SCH₂COOH |
| 062 | Cl | SCH₂COOCH(CH₃)₂ |
| 063 | Cl | SCH(CH₃)COOH₂CH₃ |
| 064 | Br | SCH(C₆H₅)COOH |
| 065 | Cl | NHSO₂CH₃ |
| 066 | Br | NHSO₂CH₃ |
| 067 | CN | NHSO₂CH₃ |
| 068 | Cl | N(CH₃)SO₂CH₃ |
| 069 | Br | N(CH₃)SO₂CH₃ |
| 070 | Cl | N(CH₂CHCH₂)SO₂CH₃ |
| 071 | CN | N(CH₂CHCH₂)SO₂CH₃ |
| 072 | Cl | N(CH₂CCH)SO₂CH₃ |
| 073 | CN | N(CH₂CCH)SO₂CH₃ |
| 074 | Cl | N(CH₂C₆H₅)SO₂CH₃ |
| 075 | Cl | NHSO₂CH₂CH₃ |
| 076 | CN | NHSO₂CH₂CH₃ |
| 077 | Cl | N(CH₂CHCH₂)SO₂CH₂CH₃ |
| 078 | Br | N(CH₂CHCH₂)SO₂CH₂CH₃ |
| 079 | CN | N(CH₂CHCH₂)SO₂CH₂CH₃ |
| 080 | Cl | N(CH₂CCH)SO₂CH₂CH₃ |
| 081 | Cl | NHSO₂CH(CH₃)₂ |
| 082 | CN | NHSO₂CH(CH₃)₂ |
| 083 | Cl | N(CH₂CCH)SO₂CH(CH₃)₂ |
| 084 | Br | N(CH₂CHCH₂)SO₂CH(CH₃)₂ |
| 085 | Cl | NHSO₂CF₃ |
| 086 | CN | NHSO₂CF₃ |
| 087 | Cl | N(CH₂CH₃)SO₂CF₃ |
| 088 | Cl | N(CH₂CHCH₂)SO₂CF₃ |
| 089 | Br | N(CH₂CHCH₂)SO₂CF₃ |
| 090 | Cl | N(CH₂CCH)SO₂CF₃ |
| 091 | Br | N(CH₂CCH)SO₂CF₃ |
| 092 | CN | N(CH₂CCH)SO₂CF₃ |
| 093 | CH₃ | N(CH₂CCH)SO₂CF₃ |
| 094 | Cl | CH₂CHClCOOH |
| 095 | Br | CH₂CHClCOOH |
| 096 | CN | CH₂CHClCOOH |
| 097 | CH₃ | CH₂CHClCOOH |
| 098 | Cl | CH₂CHClCOOCH₃ |
| 099 | Br | CH₂CHClCOOCH₃ |
| 100 | Cl | CH₂CHClCOOCH₂CH₃ |
| 101 | Br | CH₂CHClCOOCH₂CH₃ |
| 102 | CN | CH₂CHClCOOCH₂CH₃ |
| 103 | CH₃ | CH₂CHClCOOCH₂CH₃ |
| 104 | Cl | CH₂CHClCOOCH₂C₆H₅ |
| 105 | Cl | CHClCHClCOOCH₂CH₃ |
| 106 | Cl | CH₂CHBrCOOH |
| 107 | Cl | CH₂CHBrCOOCH₃ |
| 108 | Cl | CH₂CHClCOOCH₂CH₃ |
| 109 | Cl | CH₂CH(CH₃)COOCH₃ |
| 110 | Cl | CH₂CH(CH₃)COOH |
| 111 | Cl | CH(CH₃)CH₂COOCH₂CH₃ |
| 112 | Br | CH(CH₃)CH₂COOCH₂CH₃ |
| 113 | Cl | CH₂CH₂COOH |
| 114 | Cl | CH₂CH₂COOCH₃ |
| 115 | Br | CH₂CH₂COOCH₃ |
| 116 | CH₃ | CH₂CH₂COOCH₃ |
| 117 | Cl | CH₂C(CH₃)ClCOOH |
| 118 | Cl | CH₂C(CH₃)ClCOOCH₂CH₃ |
| 119 | Cl | CH₂CH(N₃)COOCH₃ |
| 120 | Br | CH₂CH(N₃)COOCH₂CH₃ |
| 121 | Cl | CH₂CHClCOOCH₂CHCH₂ |
| 122 | Cl | CH₂CHClCOOCH₂C₆H₅ |
| 123 | Cl | CH₂CHCH₂ |
| 124 | Br | CH₂CHCH₂ |
| 125 | CN | CH₂CHCH₂ |
| 126 | CH₃ | CH₂CHCH₂ |
| 127 | Cl | CHCH₂ |
| 128 | Br | CHCH₂ |
| 129 | CH₃ | CHCH₂ |
| 130 | Cl | COOH |
| 131 | Br | COOH |
| 132 | CN | COOH |
| 133 | CH₃ | COOH |
| 134 | Cl | COOCH₃ |
| 135 | Br | COOCH₃ |
| 136 | Cl | COOCH₂CH₃ |
| 137 | Br | COOCH₂CH₃ |
| 138 | CN | COOCH₂CH₃ |
| 139 | CH₃ | COOCH₂CH₃ |
| 140 | Cl | COOCH(CH₃)₂ |
| 141 | Br | COOCH(CH₃)₂ |
| 142 | CN | COOCH(CH₃)₂ |
| 143 | CH₃ | COOCH(CH₃)₂ |
| 144 | Cl | COOCH₂CHCH₂ |
| 145 | Cl | CONHCH₂CHCH₂ |
| 146 | Cl | CONHCH₂CCH |
| 147 | Cl | CON(CH₂CH₃)₂ |
| 148 | Br | CONHCH₂C₆H₅ |
| 149 | Br | CON(CH₂C₆H₅)2 |
| 150 | Cl | COOCH₂C₆H₅ |
| 151 | Cl | COOC(CH₃)₂COOH |
| 152 | Br | COOC(CH₃)₂COOH |
| 153 | CN | COOC(CH₃)₂COOH |
| 154 | CH₃ | COOC(CH₃)₂COOH |
| 155 | Cl | COOC(CH₃)₂COOCH₃ |
| 156 | Br | COOC(CH₃)₂COOCH₃ |
| 157 | CN | COOC(CH₃)₂COOCH₃ |
| 158 | CH₃ | COOC(CH₃)₂COOCH₃ |
| 159 | Cl | COOC(CH₃)₂COOCH₂CH₃ |
| 160 | Br | COOC(CH₃)₂COOCH₂CH₃ |
| 161 | Cl | COOC(CH₃)₂COOCH₂CHCH₂ |
| 162 | Br | COOC(CH₃)₂COOCH₂CHCH₂ |
| 163 | CN | COOC(CH₃)₂COOCH₂CHCH₂ |
| 164 | CH₃ | COOC(CH₃)₂COOCH₂CHCH₂ |
| 165 | Cl | COOC(CH₃)₂COOCH₂C₆H₅ |
| 166 | Br | COOC(CH₃)₂COOCH₂C₆H₅ |
| 167 | Cl | COOC(CH₃)₂COOCH₂OCH₂CH₃ |
| 168 | Br | COOC(CH₃)₂COOCH₂CH₂OCH₂CH₃ |
| 169 | CN | COOC(CH₃)₂COOCH₂CH₂OCH₂CH₃ |
| 170 | CH₃ | COOC(CH₃)₂COOCH₂CH₂OCH₂CH₃ |
| 171 | Cl | COOCH(C₆H₅)COOH |
| 172 | Br | COOCH(C₆H₅)COOH |
| 173 | CH₃ | COOCH(C₆H₅)COOH |
| 174 | Cl | COOCH(C₆H₅)COOCH₃ |
| 175 | Br | COOCH(C₆H₅)COOCH₃ |
| 176 | Cl | COOCH(C₆H₅)COOCH₂CH₃ |
| 177 | Br | COOCH(C₆H₅)COOCH₂CH₃ |
| 178 | CN | COOCH(C₆H₅)COOCH₂CH₃ |
| 179 | Cl | COOCH(C₆H₅)COOCH₂CHCH₂ |
| 180 | Cl | COOCH(C₆H₅)COOCH₂C₆H₅ |
| 181 | Cl | COOCH₂CH(CH₃)COOH |
| 182 | Br | COOCH₂CH(CH₃)COOH |
| 183 | CH₃ | COOCH₂CH(CH₃)COOH |
| 184 | CN | COOCH₂CH(CH₃)COOH |
| 185 | Cl | COOCH₂CH(CH₃)COOCH₂CH₃ |
| 186 | Br | COOCH₂CH(CH₃)COOCH₂CH₃ |
| 187 | CN | COOCH₂CH(CH₃)COOCH₂CH₃ |
| 188 | CH₃ | COOCH₂CH(CH₃)COOCH₂CH₃ |
| 189 | Cl | (S)—COOCH(CH₃)CH₂COOCH₂CH₃ |
| 190 | Br | (S)—COOCH(CH₃)CH₂COOCH₂CH₃ |
| 191 | Cl | COOC(CH₃)₂COCH₃ |
| 192 | Br | COOC(CH₃)₂COCH₃ |
| 193 | CN | COOC(CH₃)₂COCH₃ |
| 194 | Cl | COOC(CH₃)₂CONHCH₂CCH |
| 195 | Br | COOC(CH₃)₂CONHCH₂CCH |
| 196 | Cl | COOC(CH₃)₂CON(CH₂CH₃)₂ |
| 197 | CH₃ | COOC(CH₃)₂CON(CH₂CH₃)₂ |
| 198 | Cl | COOC(CH₃)₂CON(CH₂C₆H₅)2 |
| 199 | Cl | COOCH(CH₃)CONHCH₂CHCH₂ |
| 200 | Br | COOCH(CH₃)CONHCH₂CHCH₂ |
| 201 | Cl | COOCH(CH₃)CONHCH₂CCH |
| 202 | Br | COOCH(CH₃)CONHCH₂CCH |
| 203 | CN | COOCH(CH₃)CONHCH₂CCH |
| 204 | CH₃ | COOCH(CH₃)CONHCH₂CCH |
| 205 | Cl | COOCH(CH₃)CON(CH₃)₂ |
| 206 | Cl | COOCH(C₆H₅)CONHCH₂CCH |
| 207 | Cl | COOCH(C₆H₅)CON(CH₂CH₃)₂ |
| 208 | Br | COOCH(C₆H₅)CON(CH₂CH₃)₂ |
| 209 | Cl | COSCH(CH₃)COOH |
| 210 | Br | COSCH(CH₃)COOH |
| 211 | Cl | COSCH(CH₃)COOCH₃ |
| 212 | Cl | COSCH(CH₃)COOCH₂CHCH₂ |

TABLE 1-continued

| | | |
|---|---|---|
| 213 | Br | COSCH(CH$_3$)COOCH$_2$CHCH$_2$ |
| 214 | Cl | COSCH(CH$_3$)CONHCH$_2$CCH |
| 215 | Cl | CONHC(CH$_3$)$_2$COOH |
| 216 | Cl | CON(CH$_3$)C(CH$_3$)$_2$COOCH$_2$CH$_3$ |
| 217 | Cl | CON(SO$_2$CH$_3$)CH(CH$_3$)COOH |
| 218 | Cl | CON(SO$_2$CH$_3$)CH(CH$_3$)COOCH$_2$CH$_3$ |
| 219 | Cl | COOC(CH$_3$)$_2$COOC$_2$H$_5$ |
| 220 | Cl | NHSO$_2$C$_2$H$_5$ |
| 221 | Cl | N(CH$_2$CCH)SO$_2$C$_2$H$_5$ |
| 222 | Cl | N(SO$_2$CH$_3$)$_2$ |
| 223 | Cl | N(SO$_2$C$_2$H$_5$)2 |
| 224 | Br | N(SO$_2$CH$_3$)$_2$ |

TABLE 2

Compounds of the formulae I$_9$ to I$_{21}$

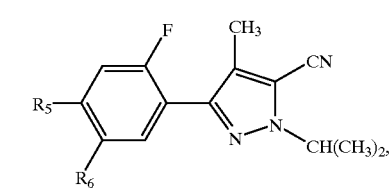

(I$_9$)

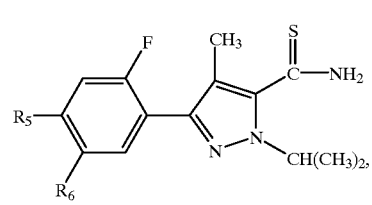

(I$_{10}$)

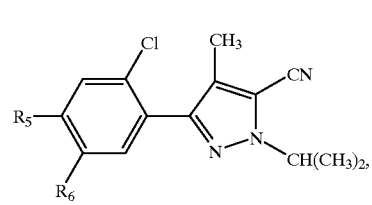

(I$_{11}$)

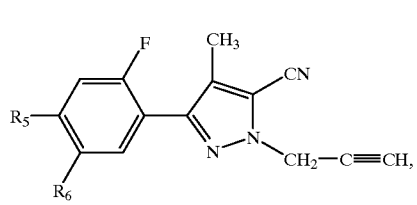

(I$_{12}$)

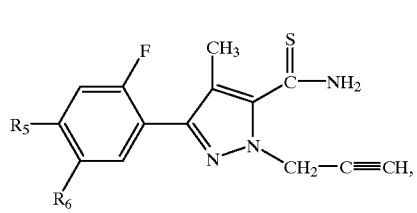

(I$_{13}$)

(I$_{14}$)

TABLE 2-continued

Compounds of the formulae I$_9$ to I$_{21}$

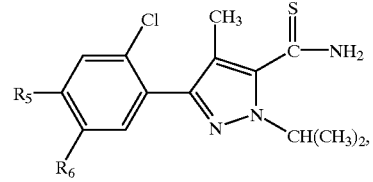

(I$_{15}$)

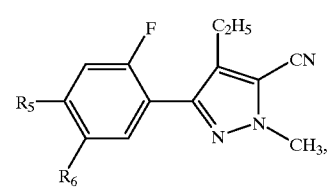

(I$_{16}$)

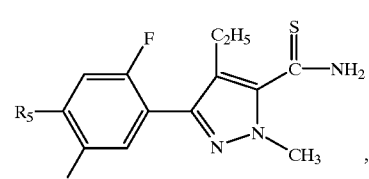

(I$_{17}$)

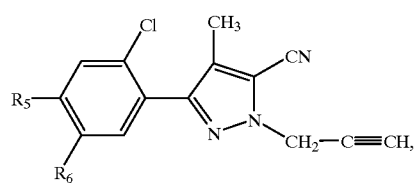

(I$_{18}$)

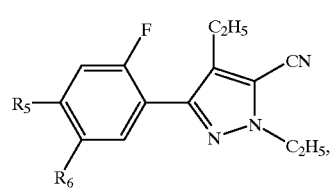

(I$_{19}$)

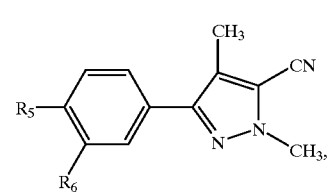

(I$_{20}$)

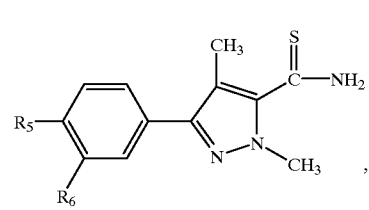

(I$_{21}$)

TABLE 2-continued

Compounds of the formulae $I_9$ to $I_{21}$

Structure: 3-(R_5, R_6-substituted phenyl)-4-methyl-5-cyano-1-ethyl-pyrazole

| Comp. No. $I_n$ n = 9–21 | $R_5$ | $R_6$ |
|---|---|---|
| 001 | Cl | H |
| 002 | Br | H |
| 003 | CN | H |
| 004 | $CH_3$ | H |
| 005 | Cl | $OCH_3$ |
| 006 | Br | $OCH_3$ |
| 007 | CN | $OCH_3$ |
| 008 | $CH_3$ | $OCH_3$ |
| 009 | Cl | $OCH_2CCH$ |
| 010 | Br | $OCH_2CCH$ |
| 011 | CN | $OCH_2CCH$ |
| 012 | $CH_3$ | $OCH_2CCH$ |
| 013 | Cl | $OCH(CH_3)_2$ |
| 014 | Cl | $OCH(CH_3)CCH$ |
| 015 | Cl | $OCH_2CHCH_2$ |
| 016 | Br | $OCH_2CHCH_2$ |
| 017 | Cl | $OCH_2C(CH_3)CH_2$ |
| 018 | Cl | $OCH_2CClCH_2$ |
| 019 | Cl | $OCH(CH_3)CHCH_2$ |
| 020 | Cl | $OCH(CH_3)COOH$ |
| 021 | Br | $OCH(CH_3)COOH$ |
| 022 | Cl | $OCH(CH_3)COOCH_3$ |
| 023 | Br | $OCH(CH_3)COOCH_2CH_3$ |
| 024 | $CH_3$ | $OCH(CH_3)COOCH_2CHCH_2$ |
| 025 | CN | $OCH(CH_3)COOCH_2C_6H_5$ |
| 026 | Cl | $OCH(C_6H_5)COOH$ |
| 027 | Br | $OCH(C_6H_5)COOH$ |
| 028 | Cl | $OCH(C_6H_5)COOCH_3$ |
| 029 | Br | $OCH(C_6H_5)COOCH(CH_3)_2$ |
| 030 | $CH_3$ | $OCH(C_6H_5)COOCH_2C_6H_5$ |
| 031 | CN | $OCH(C_6H_5)COOCH_2CHCH_2$ |
| 032 | Cl | $SCH_3$ |
| 033 | Cl | $SCH(CH_3)_2$ |
| 034 | $CH_3$ | $SCH(CH_3)_2$ |
| 035 | Br | $NH(CH_2CHCH_2)$ |
| 036 | $CH_3$ | $N(CH_3)_2$ |
| 037 | Cl | $N(SO_2CH_3)CH_3$ |
| 038 | Cl | $N(SO_2CH_3)CH_2CHCH_2$ |
| 039 | Br | $N(SO_2CH_2CH_3)CH_2CCH$ |
| 040 | $CH_3$ | $N(SO_2CF_3)CH_2CH_3$ |
| 041 | Cl | $N(SO_2CF_3)CH(CH_3)CHCH_2$ |
| 042 | Cl | $CHCH_2$ |
| 043 | Cl | $CH_2CHCH_2$ |
| 044 | Br | $CH_2CHCH_2$ |
| 045 | Cl | $CH_2CHClCOOH$ |
| 046 | Br | $CH_2CHClCOOH$ |
| 047 | Cl | $CH_2CHClCOOCH_3$ |
| 048 | Cl | $CH_2CHClCOCH_2CH_3$ |
| 049 | Br | $CH_2CHClCOCH_2CH_3$ |
| 050 | CN | $CH_2CHClCOCH_2CH_3$ |
| 051 | $CH_3$ | $CH_2CHClCOCH_2CH_3$ |
| 052 | Cl | $CH_2CHClCOOCH_2CHCH_2$ |
| 053 | Br | $CH_2CHClCOOCH_2C_6H_5$ |
| 054 | Cl | $CH_2CH(CH_3)COOH$ |
| 055 | Br | $CH_2CH(CH_3)COOCH_3$ |
| 056 | Cl | $CH_2CH_2COOCH_3$ |
| 057 | Cl | COOH |
| 058 | Br | COOH |
| 059 | $CH_3$ | $COOCH_3$ |
| 060 | Cl | $COOCH_2CH_3$ |
| 061 | Br | $COOCH_2CH_3$ |
| 062 | $CH_3$ | $COOCH_2CHCH_2$ |
| 063 | Cl | $COOCH(CH_3)_2$ |
| 064 | CN | $COOCH_2C_6H_5$ |
| 065 | Cl | $COOCH(CH_3)COOH$ |
| 066 | Br | $COOCH(CH_3)COOCH_3$ |
| 067 | Cl | $COOCH(CH_3)COOCH_2CHCH_2$ |
| 068 | Cl | $COOCH(C_6H_5)COOH$ |
| 069 | Br | $COOCH(C_6H_5)COOCH_3$ |
| 070 | $CH_3$ | $COOCH(C_6H_5)COOCH(CH_3)_2$ |
| 071 | Cl | $COOC(CH_3)_2COOH$ |
| 072 | $CH_3$ | $COOC(CH_3)_2COOH$ |
| 073 | Br | $COOC(CH_3)_2COOCH_3$ |
| 074 | Cl | $COOC(CH_3)_2COOCH_2CH_3$ |
| 075 | Br | $COOC(CH_3)_2COOCH_2CH_3$ |
| 076 | $CH_3$ | $COOC(CH_3)_2COOCH_2CH_3$ |
| 077 | CN | $COOC(CH_3)_2COOCH_2CCH$ |
| 078 | Cl | $COOC(CH_3)_2CONH(CH_2CCH)$ |
| 079 | Br | $COOC(CH_3)_2CON(CH_2CHCH_2)_2$ |
| 080 | Cl | $COOC(CH_3)_2CONH_2$ |
| 081 | Cl | $COOCH(CH_3)CH_2COOCH_3$ |
| 082 | Cl | $COSCH(CH_3)COOH$ |
| 083 | Cl | $COSCH(CH_3)COOCH_2CH_3$ |

TABLE 3

Compounds of the formulae $I_{22}$ to $I_{28}$ ($I_{22}$) – fluoro-substituted benzo-fused ring with $X_2$, N-$R_{61}$, lactam, linked to 4-methyl-5-cyano-1-methyl-pyrazole, ($I_{23}$) – fluoro-substituted benzo-fused ring with $X_2$, N-$R_{61}$, lactam, linked to 4-methyl-1-methyl-pyrazole-5-thiocarboxamide, ($I_{24}$) – chloro-substituted benzo-fused ring with $X_2$, N-$R_{61}$, lactam, linked to 4-methyl-5-cyano-1-methyl-pyrazole, ($I_{25}$) – chloro-substituted benzo-fused ring with $X_2$, N-$R_{61}$, lactam, linked to 4-methyl-1-methyl-pyrazole-5-thiocarboxamide,

TABLE 3-continued

Compounds of the formulae $I_{22}$ to $I_{28}$ ($I_{26}$) structure: fluoro-substituted benzene fused to a ring containing $X_2$, CH$_2$, C=O, N-$R_{61}$, connected to pyrazole bearing CH$_3$, CN, N-C$_2$H$_5$.

($I_{27}$) structure: chloro-substituted analog of $I_{26}$.

($I_{28}$) structure: fluoro-substituted analog with thioamide (C(=S)NH$_2$) in place of CN.

| Comp No. $I_n$ n = 22–28 | $X_2$ | $R_{61}$ |
|---|---|---|
| 001 | O | H |
| 002 | S | H |
| 003 | O | CH$_3$ |
| 004 | O | CH$_2$CHCH$_2$ |
| 005 | S | CH$_2$CHCH$_2$ |
| 006 | O | CH(CH$_3$)CHCH$_2$ |
| 007 | S | CH(CH$_3$)CHCH$_2$ |
| 008 | O | CH(CH$_3$)$_2$ |
| 009 | O | CH$_2$CCH |
| 010 | O | CH(CH$_3$)CCH |
| 011 | S | CH$_2$CCH |
| 012 | O | CH$_2$C$_6$H$_5$ |
| 013 | O | CH$_2$COOH |
| 014 | S | CH$_2$COOH |
| 015 | O | CH$_2$COOCH$_3$ |
| 016 | O | CH$_2$COOCH$_2$CH$_3$ |
| 017 | S | CH$_2$COOCH$_2$CH$_3$ |
| 018 | O | CH(CH$_3$)COOH |
| 019 | O | CH(CH$_3$)COOCH$_3$ |
| 020 | O | CH(CH$_3$)COOCH$_2$CH$_3$ |
| 021 | O | CH(CH$_3$)COOCH$_2$CHCH$_2$ |
| 022 | O | CH(CH$_3$)COOCH$_2$C$_6$H$_5$ |
| 023 | O | CH(C$_6$H$_5$)COOH |
| 024 | O | CH(C$_6$H$_5$)COOCH$_2$CH$_3$ |
| 025 | O | CH$_2$CH$_2$OCH$_2$CH$_3$ |
| 026 | S | CH$_2$CH$_2$OCH$_2$CH$_3$ |
| 027 | O | CH$_2$OCH$_3$ |

TABLE 4

Compounds of the formulae $I_{29}$ to $I_{32}$ ($I_{29}$) benzothiazolone with $R_4$ substituent, connected to pyrazole bearing CH$_3$, CN, N-CH$_3$; N-$R_{61}$ on benzothiazolone.

($I_{30}$) analog of $I_{29}$ with C(=S)NH$_2$ in place of CN.

($I_{31}$) analog of $I_{29}$ with N-C$_2$H$_5$ on pyrazole.

($I_{32}$) analog with C(=S)NH$_2$ and N-C$_2$H$_5$.

| Comp. No. $I_n$ n = 29–32 | $R_4$ | $R_{61}$ |
|---|---|---|
| 001 | F | H |
| 002 | F | CH$_3$ |
| 003 | F | CH$_2$CH$_3$ |
| 004 | F | CH(CH$_3$)$_2$ |
| 005 | F | CH$_2$CHCH$_2$ |
| 006 | F | CH(CH$_3$)CHCH$_2$ |
| 007 | F | CH$_2$CCH |
| 008 | F | CH(CH$_3$)CCH |
| 009 | F | CH$_2$C$_6$H$_5$ |
| 010 | F | CH$_2$COOH |
| 011 | F | CH$_2$COOCH$_3$ |
| 012 | F | CH$_2$CH(CH$_3$)$_2$ |
| 013 | F | CH(CH$_3$)COOH |
| 014 | F | CH(CH$_3$)COOCH$_3$ |
| 015 | F | CH(CH$_3$)COOCH$_2$CH$_3$ |
| 016 | F | CH(CH$_3$)COOCH$_2$C$_6$H$_5$ |
| 017 | F | CH(C$_6$H$_5$)COOH |
| 018 | F | CH(C$_6$H$_5$)COOCH$_2$CHCH$_2$ |
| 019 | Cl | H |
| 020 | Cl | CH$_2$CH$_3$ |
| 021 | Cl | CH(CH$_3$)$_2$ |
| 022 | Cl | CH$_2$CHCH$_2$ |
| 023 | Cl | CH$_2$CCH |

TABLE 4-continued

Compounds of the formulae $I_{29}$ to $I_{32}$

| | | |
|---|---|---|
| 024 | Cl | CH$_2$COOH |
| 025 | Cl | CH$_2$COOCH$_3$ |
| 026 | Cl | CH$_2$COOCH$_2$CHCH$_2$ |
| 027 | Cl | CH(CH$_3$)COOH |
| 028 | Cl | CH(CH$_3$)COOCH$_2$CH$_3$ |
| 029 | CH$_3$ | H |
| 030 | CH$_3$ | CH$_2$CCH |
| 031 | CH$_3$ | CH$_2$COOH |
| 032 | CH$_3$ | CH$_2$COOCH$_2$CH$_3$ |
| 033 | CH$_3$ | CH(CH$_3$)COOH |
| 034 | H | H |
| 035 | H | CH(CH$_3$)$_2$ |
| 036 | H | CH$_2$CCH |
| 037 | H | CH$_2$COOH |

TABLE 5

Compounds of the formulae $I_{33}$ to $I_{35}$

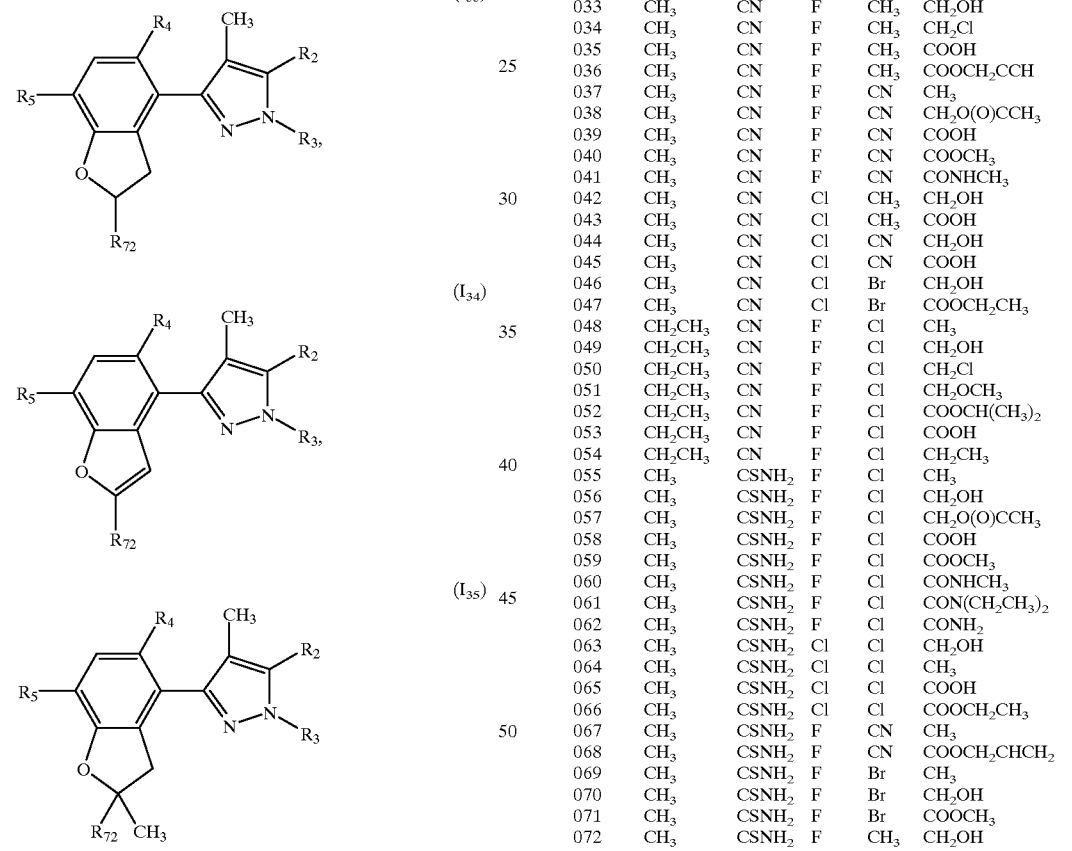

| Comp. No. $I_n$ n = 33–35 | R$_3$ | R$_2$ | R$_4$ | R$_5$ | R$_{72}$ |
|---|---|---|---|---|---|
| 001 | CH$_3$ | CN | F | Cl | H |
| 002 | CH$_3$ | CN | F | Cl | CH$_3$ |
| 003 | CH$_3$ | CN | F | Cl | CH$_2$CH$_3$ |
| 004 | CH$_3$ | CN | F | Cl | CH$_2$Cl |
| 005 | CH$_3$ | CN | F | Cl | CH$_2$OH |
| 006 | CH$_3$ | CN | F | Cl | CH$_2$OCH$_3$ |
| 007 | CH$_3$ | CN | F | Cl | CH$_2$O(O)CCH$_3$ |
| 008 | CH$_3$ | CN | F | Cl | CH$_2$O(O)CCH$_2$Cl |
| 009 | CH$_3$ | CN | F | Cl | COOH |
| 010 | CH$_3$ | CN | F | Cl | COOCH$_3$ |
| 011 | CH$_3$ | CN | F | Cl | COOCH$_2$CH$_3$ |
| 012 | CH$_3$ | CN | F | Cl | COOCH$_2$CHCH$_2$ |
| 013 | CH$_3$ | CN | F | Cl | COOCH$_2$C$_6$H$_5$ |
| 014 | CH$_3$ | CN | F | Cl | COOCH$_2$CCH |
| 015 | CH$_3$ | CN | F | Cl | CONH$_2$ |
| 016 | CH$_3$ | CN | F | Cl | CON(CH$_2$CH$_3$)$_2$ |
| 017 | CH$_3$ | CN | F | Cl | CONHCH$_2$CCH |
| 018 | CH$_3$ | CN | F | Br | CH$_3$ |
| 019 | CH$_3$ | CN | F | Br | CH$_2$OH |
| 020 | CH$_3$ | CN | F | Br | CH$_2$Br |
| 021 | CH$_3$ | CN | F | Br | COOH |
| 022 | CH$_3$ | CN | F | Br | COOCH$_3$ |
| 023 | CH$_3$ | CN | F | Br | COOCH(CH$_3$)$_2$ |
| 024 | CH$_3$ | CN | F | Br | COOCH$_2$CHCH$_2$ |
| 025 | CH$_3$ | CN | F | Br | CONHCH$_2$CHCH$_2$ |
| 026 | CH$_3$ | CN | Cl | Cl | CH$_3$ |
| 027 | CH$_3$ | CN | Cl | Cl | CH$_2$OH |
| 028 | CH$_3$ | CN | Cl | Cl | CH$_2$O(O)CCH$_3$ |
| 029 | CH$_3$ | CN | Cl | Cl | COOH |
| 030 | CH$_3$ | CN | Cl | Cl | COOCH$_2$CH$_3$ |
| 031 | CH$_3$ | CN | Cl | Cl | COOCH$_2$C$_6$H$_5$ |
| 032 | CH$_3$ | CN | Cl | Cl | CON(CH$_2$CHCH$_2$)$_2$ |
| 033 | CH$_3$ | CN | F | CH$_3$ | CH$_2$OH |
| 034 | CH$_3$ | CN | F | CH$_3$ | CH$_2$Cl |
| 035 | CH$_3$ | CN | F | CH$_3$ | COOH |
| 036 | CH$_3$ | CN | F | CH$_3$ | COOCH$_2$CCH |
| 037 | CH$_3$ | CN | F | CN | CH$_3$ |
| 038 | CH$_3$ | CN | F | CN | CH$_2$O(O)CCH$_3$ |
| 039 | CH$_3$ | CN | F | CN | COOH |
| 040 | CH$_3$ | CN | F | CN | COOCH$_3$ |
| 041 | CH$_3$ | CN | F | CN | CONHCH$_3$ |
| 042 | CH$_3$ | CN | Cl | CH$_3$ | CH$_2$OH |
| 043 | CH$_3$ | CN | Cl | CH$_3$ | COOH |
| 044 | CH$_3$ | CN | Cl | CN | CH$_2$OH |
| 045 | CH$_3$ | CN | Cl | CN | COOH |
| 046 | CH$_3$ | CN | Cl | Br | CH$_2$OH |
| 047 | CH$_3$ | CN | Cl | Br | COOCH$_2$CH$_3$ |
| 048 | CH$_2$CH$_3$ | CN | F | Cl | CH$_3$ |
| 049 | CH$_2$CH$_3$ | CN | F | Cl | CH$_2$OH |
| 050 | CH$_2$CH$_3$ | CN | F | Cl | CH$_2$Cl |
| 051 | CH$_2$CH$_3$ | CN | F | Cl | CH$_2$OCH$_3$ |
| 052 | CH$_2$CH$_3$ | CN | F | Cl | COOCH(CH$_3$)$_2$ |
| 053 | CH$_2$CH$_3$ | CN | F | Cl | COOH |
| 054 | CH$_2$CH$_3$ | CN | F | Cl | CH$_2$CH$_3$ |
| 055 | CH$_3$ | CSNH$_2$ | F | Cl | CH$_3$ |
| 056 | CH$_3$ | CSNH$_2$ | F | Cl | CH$_2$OH |
| 057 | CH$_3$ | CSNH$_2$ | F | Cl | CH$_2$O(O)CCH$_3$ |
| 058 | CH$_3$ | CSNH$_2$ | F | Cl | COOH |
| 059 | CH$_3$ | CSNH$_2$ | F | Cl | COOCH$_3$ |
| 060 | CH$_3$ | CSNH$_2$ | F | Cl | CONHCH$_3$ |
| 061 | CH$_3$ | CSNH$_2$ | F | Cl | CON(CH$_2$CH$_3$)$_2$ |
| 062 | CH$_3$ | CSNH$_2$ | F | Cl | CONH$_2$ |
| 063 | CH$_3$ | CSNH$_2$ | Cl | Cl | CH$_2$OH |
| 064 | CH$_3$ | CSNH$_2$ | Cl | Cl | CH$_3$ |
| 065 | CH$_3$ | CSNH$_2$ | Cl | Cl | COOH |
| 066 | CH$_3$ | CSNH$_2$ | Cl | Cl | COOCH$_2$CH$_3$ |
| 067 | CH$_3$ | CSNH$_2$ | F | CN | CH$_3$ |
| 068 | CH$_3$ | CSNH$_2$ | F | CN | COOCH$_2$CHCH$_2$ |
| 069 | CH$_3$ | CSNH$_2$ | F | Br | CH$_3$ |
| 070 | CH$_3$ | CSNH$_2$ | F | Br | CH$_2$OH |
| 071 | CH$_3$ | CSNH$_2$ | F | Br | COOCH$_3$ |
| 072 | CH$_3$ | CSNH$_2$ | F | CH$_3$ | CH$_2$OH |
| 073 | CH$_3$ | CSNH$_2$ | F | CH$_3$ | COOCH$_2$CCH |
| 074 | CH$_3$ | CSNH$_2$ | Cl | Cl | CH$_2$OH |
| 075 | CH$_3$ | CSNH$_2$ | Cl | Cl | COOCH$_3$ |
| 076 | CH$_2$CH$_3$ | CSNH$_2$ | F | Cl | CH$_3$ |
| 077 | CH$_2$CH$_3$ | CSNH$_2$ | F | Cl | CH$_2$OH |
| 078 | CH$_2$CH$_3$ | CSNH$_2$ | F | Cl | CH$_2$Cl |
| 079 | CH$_2$CH$_3$ | CSNH$_2$ | F | Cl | COOH |
| 080 | CH$_2$CH$_3$ | CSNH$_2$ | Cl | Cl | CH$_2$O(O)CCH$_3$ |
| 081 | CH(CH$_3$)$_2$ | CN | F | Cl | CH$_3$ |
| 082 | CH(CH$_3$)$_2$ | CN | F | Cl | CH$_2$Cl |
| 083 | CH(CH$_3$)$_2$ | CN | F | Cl | COOH |
| 084 | CH(CH$_3$)$_2$ | CN | F | Cl | COOCH$_2$CHCH$_2$ |
| 085 | CH(CH$_3$)$_2$ | CN | F | Br | CH$_2$OH |
| 086 | CH(CH$_3$)$_2$ | CN | F | Br | COOH |
| 087 | CH$_3$ | CN | H | Cl | CH$_2$OH |

TABLE 5-continued

Compounds of the formulae $I_{33}$ to $I_{35}$

| | | | | | |
|---|---|---|---|---|---|
| 088 | $CH_3$ | CN | H | Cl | COOH |
| 089 | $CH_3$ | CN | H | Cl | $COOCH_3$ |
| 090 | $CH_3$ | CN | H | Cl | Cl |
| 091 | $CH_2CH_3$ | CN | H | Cl | $CH_2OH$ |
| 092 | $CH_3$ | CN | H | Br | $CH_2OH$ |
| 093 | $CH_2CH_3$ | CN | H | Br | $COOCH_3$ |

TABLE 6

Compounds of the formulae $V_1$, $V_2$, $II_1$ and $III_1$

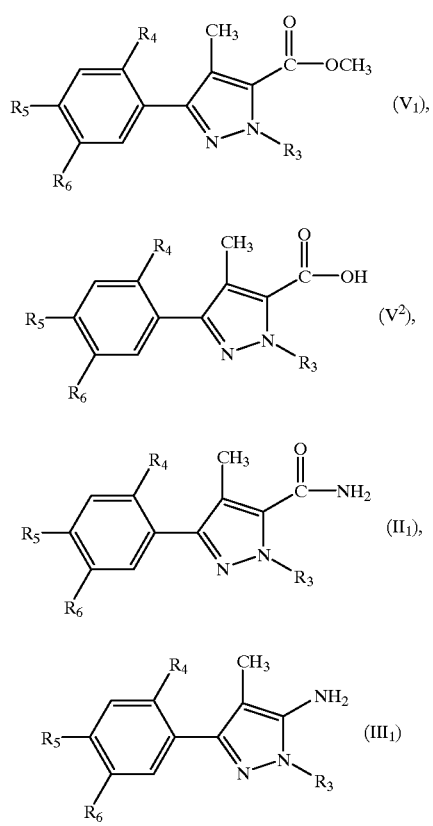

| Comp. No. $V_n$ or $II_1$ and $III_1$ n = 1 or 2 | $R_3$ | $R_4$ | $R_5$ | $R_6$ |
|---|---|---|---|---|
| 001 | $CH_3$ | F | Cl | H |
| 002 | $CH_3$ | F | Br | H |
| 003 | $CH_3$ | F | CN | H |
| 004 | $CH_3$ | F | $CH_3$ | H |
| 005 | $CH_3$ | Cl | Cl | H |
| 006 | $CH_3$ | Cl | Br | H |
| 007 | $CH_3$ | Cl | CN | H |
| 008 | $CH_3$ | Cl | $CH_3$ | H |
| 009 | $CH_3$ | F | F | H |
| 010 | $CH_2CH_3$ | F | Cl | H |
| 011 | $CH_2CH_3$ | F | Br | H |
| 012 | $CH_2CH_3$ | F | CN | H |
| 013 | $CH_2CH_3$ | F | $CH_3$ | H |
| 014 | $CH_2CH_3$ | Cl | Cl | H |
| 015 | $CH_2CH_3$ | Cl | Br | H |
| 016 | $CH_2CH_3$ | Cl | CN | H |
| 017 | $CH_2CH_3$ | Cl | $CH_3$ | H |
| 018 | $CH_2CH_3$ | F | F | H |
| 019 | $CH(CH_3)_2$ | F | Cl | H |
| 020 | $CH(CH_3)_2$ | F | Br | H |
| 021 | $CH(CH_3)_2$ | F | CN | H |
| 022 | $CH(CH_3)_2$ | F | $CH_3$ | H |
| 023 | $CH(CH_3)_2$ | Cl | Cl | H |
| 024 | $CH(CH_3)_2$ | Cl | Br | H |
| 025 | $CH(CH_3)_2$ | Cl | CN | H |
| 026 | $CH(CH_3)_2$ | Cl | $CH_3$ | H |
| 027 | $CH(CH_3)_2$ | F | F | H |
| 028 | $CH_3$ | F | $NO_2$ | H |
| 029 | $CH_3$ | Cl | $NO_2$ | H |
| 030 | $CH_2CH_3$ | F | $NO_2$ | H |
| 031 | $CH_2CH_3$ | Cl | $NO_2$ | H |
| 032 | $CH(CH_3)_2$ | F | $NO_2$ | H |
| 033 | $CH(CH_3)_2$ | Cl | $NO_2$ | H |
| 034 | $CH_3$ | F | $NH_2$ | H |
| 035 | $CH_3$ | Cl | $NH_2$ | H |
| 036 | $CH_2CH_3$ | F | $NH_2$ | H |
| 037 | $CH_2CH_3$ | Cl | $NH_2$ | H |
| 038 | $CH(CH_3)_2$ | F | $NH_2$ | H |
| 039 | $CH(CH_3)_2$ | Cl | $NH_2$ | H |
| 040 | $CH_3$ | F | H | F |
| 041 | $CH_2CH_3$ | F | H | F |
| 042 | $CH(CH_3)_2$ | F | H | F |
| 043 | $CH_3$ | F | OH | H |
| 044 | $CH_2CH_3$ | F | OH | H |
| 045 | $CH(CH_3)_2$ | F | OH | H |
| 046 | $CH_3$ | F | $OCH_3$ | H |
| 047 | $CH_2CH_3$ | F | $OCH_3$ | H |
| 048 | $CH(CH_3)_2$ | F | $OCH_3$ | H |
| 049 | $CH_3$ | Cl | OH | H |
| 050 | $CH_2CH_3$ | Cl | OH | H |
| 051 | $CH(CH_3)_2$ | Cl | OH | H |
| 052 | $CH_3$ | Cl | $OCH_3$ | H |
| 053 | $CH_2CH_3$ | Cl | $OCH_3$ | H |
| 054 | $CH(CH_3)_2$ | Cl | $OCH_3$ | H |
| 055 | $CH_3$ | F | $OCH_2COOCH_3$ | $NO_2$ |
| 056 | $CH_2CH_3$ | F | $OCH_2COOCH_3$ | $NO_2$ |
| 057 | $CH_3$ | Cl | $OCH_2COOCH_3$ | $NO_2$ |
| 058 | $CH_2CH_3$ | Cl | $OCH_2COOCH_3$ | $NO_2$ |
| 059 | $CH_3$ | F | Cl | OH |
| 060 | $CH_2CH_3$ | F | Cl | OH |
| 061 | $CH(CH_3)_2$ | F | Cl | OH |
| 062 | $CH_3$ | Cl | Cl | OH |
| 063 | $CH_2CH_3$ | Cl | Cl | OH |
| 064 | $CH_3$ | F | Br | OH |
| 065 | $CH_3$ | F | $CH_3$ | OH |
| 066 | $CH_3$ | F | CN | OH |
| 067 | $CH_2CH_3$ | F | Br | OH |
| 068 | $CH_2CH_3$ | F | $CH_3$ | OH |
| 069 | $CH_2CH_3$ | F | CN | OH |
| 070 | $CH_3$ | Cl | CN | OH |
| 071 | $CH_3$ | F | Cl | $OCH_3$ |
| 072 | $CH_2CH_3$ | F | Cl | $OCH_3$ |
| 073 | $CH(CH_3)_2$ | F | Cl | $OCH_3$ |
| 074 | $CH_3$ | Cl | Cl | $OCH_3$ |
| 075 | $CH_2CH_3$ | Cl | Cl | $OCH_3$ |
| 076 | $CH_3$ | F | Br | $OCH_3$ |
| 077 | $CH_3$ | F | $CH_3$ | $OCH_3$ |
| 078 | $CH_3$ | F | CN | $OCH_3$ |
| 079 | $CH_2CH_3$ | F | Br | $OCH_3$ |
| 080 | $CH_2CH_3$ | F | $CH_3$ | $OCH_3$ |
| 081 | $CH_2CH_3$ | F | CN | $OCH_3$ |
| 082 | $CH_3$ | Cl | CN | $OCH_3$ |
| 083 | $CH_3$ | F | Cl | $OCH_2CHCH_2$ |
| 084 | $CH_2CH_3$ | F | Cl | $OCH_2CHCH_2$ |
| 085 | $CH(CH_3)_2$ | F | Cl | $OCH_2CHCH_2$ |
| 086 | $CH_3$ | Cl | Cl | $OCH_2CHCH_2$ |
| 087 | $CH_2CH_3$ | Cl | Cl | $OCH_2CHCH_2$ |
| 088 | $CH_3$ | F | Br | $OCH_2CHCH_2$ |
| 089 | $CH_3$ | F | $CH_3$ | $OCH_2CHCH_2$ |
| 090 | $CH_3$ | F | CN | $OCH_2CHCH_2$ |
| 091 | $CH_2CH_3$ | F | Br | $OCH_2CHCH_2$ |
| 092 | $CH_2CH_3$ | F | $CH_3$ | $OCH_2CHCH_2$ |
| 093 | $CH_2CH_3$ | F | CN | $OCH_2CHCH_2$ |
| 094 | $CH_3$ | Cl | CN | $OCH_2CHCH_2$ |
| 095 | $CH_3$ | F | Cl | $OCH_2C(CH_3)CH_2$ |
| 096 | $CH_2CH_3$ | F | Cl | $OCH_2C(CH_3)CH_2$ |
| 097 | $CH(CH_3)_2$ | F | Cl | $OCH_2C(CH_3)CH_2$ |

TABLE 6-continued

Compounds of the formulae $V_1$, $V_2$, $II_1$ and $III_1$

| | | | | |
|---|---|---|---|---|
| 098 | $CH_3$ | Cl | Cl | $OCH_2C(CH_3)CH_2$ |
| 099 | $CH_2CH_3$ | Cl | Cl | $OCH_2C(CH_3)CH_2$ |
| 100 | $CH_3$ | F | Br | $OCH_2C(CH_3)CH_2$ |
| 101 | $CH_3$ | F | $CH_3$ | $OCH_2C(CH_3)CH_2$ |
| 102 | $CH_3$ | F | CN | $OCH_2C(CH_3)CH_2$ |
| 103 | $CH_2CH_3$ | F | Br | $OCH_2C(CH_3)CH_2$ |
| 104 | $CH_2CH_3$ | F | $CH_3$ | $OCH_2C(CH_3)CH_2$ |
| 105 | $CH_2CH_3$ | F | CN | $OCH_2C(CH_3)CH_2$ |
| 106 | $CH_3$ | Cl | CN | $OCH_2C(CH_3)CH_2$ |
| 107 | $CH_3$ | F | Cl | $OCH_2CClCH_2$ |
| 108 | $CH_2CH_3$ | F | Cl | $OCH_2CClCH_2$ |
| 109 | $CH_3$ | F | F | $NO_2$ |
| 110 | $CH_2CH_3$ | F | F | $NO_2$ |
| 111 | $CH(CH_3)_2$ | F | F | $NO_2$ |
| 112 | $CH_3$ | F | Cl | $NO_2$ |
| 113 | $CH_2CH_3$ | F | Cl | $NO_2$ |
| 114 | $CH(CH_3)_2$ | F | Cl | $NO_2$ |
| 115 | $CH_3$ | Cl | Cl | $NO_2$ |
| 116 | $CH_2CH_3$ | Cl | Cl | $NO_2$ |
| 117 | $CH_3$ | F | Br | $NO_2$ |
| 118 | $CH_3$ | F | $CH_3$ | $NO_2$ |
| 119 | $CH_3$ | F | CN | $NO_2$ |
| 120 | $CH_2CH_3$ | F | Br | $NO_2$ |
| 121 | $CH_2CH_3$ | F | $CH_3$ | $NO_2$ |
| 122 | $CH_2CH_3$ | F | CN | $NO_2$ |
| 123 | $CH_3$ | Cl | CN | $NO_2$ |
| 124 | $CH_3$ | F | OH | $NO_2$ |
| 125 | $CH_2CH_3$ | F | OH | $NO_2$ |
| 126 | $CH_3$ | Cl | OH | $NO_2$ |
| 127 | $CH_3$ | F | Cl | $NH_2$ |
| 128 | $CH_2CH_3$ | F | Cl | $NH_2$ |
| 129 | $CH(CH_3)_2$ | F | Cl | $NH_2$ |
| 130 | $CH_3$ | Cl | Cl | $NH_2$ |
| 131 | $CH_2CH_3$ | Cl | Cl | $NH_2$ |
| 132 | $CH_3$ | F | Br | $NH_2$ |
| 133 | $CH_3$ | F | $CH_3$ | $NH_2$ |
| 134 | $CH_3$ | F | CN | $NH_2$ |
| 135 | $CH_2CH_3$ | F | Br | $NH_2$ |
| 136 | $CH_2CH_3$ | F | $CH_3$ | $NH_2$ |
| 137 | $CH_2CH_3$ | F | CN | $NH_2$ |
| 138 | $CH_3$ | Cl | CN | $NH_2$ |
| 139 | $CH_3$ | F | Cl | Br |
| 140 | $CH_2CH_3$ | F | Cl | Br |
| 141 | $CH(CH_3)_2$ | F | Cl | Br |
| 142 | $CH_3$ | Cl | Cl | Br |
| 143 | $CH_2CH_3$ | Cl | Cl | Br |
| 144 | $CH_3$ | F | Br | Br |
| 145 | $CH_3$ | F | $CH_3$ | Br |
| 146 | $CH_3$ | F | CN | Br |
| 147 | $CH_2CH_3$ | F | Br | Br |
| 148 | $CH_2CH_3$ | F | $CH_3$ | Br |
| 149 | $CH_2CH_3$ | F | CN | Br |
| 150 | $CH_3$ | Cl | CN | Br |
| 151 | $CH_3$ | F | Cl | I |
| 152 | $CH_2CH_3$ | F | Cl | I |
| 153 | $CH(CH_3)_2$ | F | Cl | I |
| 154 | $CH_3$ | Cl | Cl | I |
| 155 | $CH_2CH_3$ | Cl | Cl | I |
| 156 | $CH_3$ | F | Br | I |
| 157 | $CH_3$ | F | $CH_3$ | I |
| 158 | $CH_3$ | F | CN | I |
| 159 | $CH_2CH_3$ | F | Br | I |
| 160 | $CH_2CH_3$ | F | $CH_3$ | I |
| 161 | $CH_2CH_3$ | F | CN | I |
| 162 | $CH_3$ | Cl | CN | I |
| 163 | $CH_3$ | F | Cl | $OSO_2CF_3$ |
| 164 | $CH_2CH_3$ | F | Cl | $OSO_2CF_3$ |
| 165 | $CH(CH_3)_2$ | F | Cl | $OSO_2CF_3$ |
| 166 | $CH_3$ | Cl | Cl | $OSO_2CF_3$ |
| 167 | $CH_2CH_3$ | Cl | Cl | $OSO_2CF_3$ |
| 168 | $CH_3$ | F | Br | $OSO_2CF_3$ |
| 169 | $CH_3$ | F | $CH_3$ | $OSO_2CF_3$ |
| 170 | $CH_3$ | F | CN | $OSO_2CF_3$ |
| 171 | $CH_2CH_3$ | F | Br | $OSO_2CF_3$ |
| 172 | $CH_2CH_3$ | F | $CH_3$ | $OSO_2CF_3$ |
| 173 | $CH_2CH_3$ | F | CN | $OSO_2CF_3$ |
| 174 | $CH_3$ | Cl | CN | $OSO_2CF_3$ |
| 175 | $CH_3$ | F | Cl | COOH |
| 176 | $CH_2CH_3$ | F | Cl | COOH |
| 177 | $CH(CH_3)_2$ | F | Cl | COOH |
| 178 | $CH_3$ | Cl | Cl | COOH |
| 179 | $CH_2CH_3$ | Cl | Cl | COOH |
| 180 | $CH_3$ | F | Br | COOH |
| 181 | $CH_3$ | F | $CH_3$ | COOH |
| 182 | $CH_3$ | F | CN | COOH |
| 183 | $CH_2CH_3$ | F | Br | COOH |
| 184 | $CH_2CH_3$ | F | $CH_3$ | COOH |
| 185 | $CH_2CH_3$ | F | CN | COOH |
| 186 | $CH_3$ | Cl | CN | COOH |
| 187 | $CH_3$ | F | Cl | $COOCH_2CH_3$ |
| 188 | $CH_2CH_3$ | F | Cl | $COOCH_2CH_3$ |
| 189 | $CH(CH_3)_2$ | F | Cl | $COOCH_2CH_3$ |
| 190 | $CH_3$ | Cl | Cl | $COOCH_2CH_3$ |
| 191 | $CH_2CH_3$ | Cl | Cl | $COOCH_2CH_3$ |
| 192 | $CH_3$ | F | Br | $COOCH_2CH_3$ |
| 193 | $CH_3$ | F | $CH_3$ | $COOCH_2CH_3$ |
| 194 | $CH_3$ | F | CN | $COOCH_2CH_3$ |
| 195 | $CH_2CH_3$ | F | Br | $COOCH_2CH_3$ |
| 196 | $CH_2CH_3$ | F | $CH_3$ | $COOCH_2CH_3$ |
| 197 | $CH_2CH_3$ | F | CN | $COOCH_2CH_3$ |
| 198 | $CH_3$ | Cl | CN | $COOCH_2CH_3$ |
| 199 | $CH_3$ | F | Cl | $COOCH_2C_6H_5$ |
| 200 | $CH_2CH_3$ | F | Cl | $COOCH_2C_6H_5$ |
| 201 | $CH(CH_3)_2$ | F | Cl | $COOCH_2C_6H_5$ |
| 202 | $CH_3$ | Cl | Cl | $COOCH_2C_6H_5$ |
| 203 | $CH_2CH_3$ | Cl | Cl | $COOCH_2C_6H_5$ |
| 204 | $CH_3$ | F | Br | $COOCH_2C_6H_5$ |
| 205 | $CH_3$ | F | $CH_3$ | $COOCH_2C_6H_5$ |
| 206 | $CH_3$ | F | CN | $COOCH_2C_6H_5$ |
| 207 | $CH_2CH_3$ | F | Br | $COOCH_2C_6H_5$ |
| 208 | $CH_2CH_3$ | F | $CH_3$ | $COOCH_2C_6H_5$ |
| 209 | $CH_2CH_3$ | F | CN | $COOCH_2C_6H_5$ |
| 210 | $CH_3$ | Cl | CN | $COOCH_2C_6H_5$ |
| 211 | $CH_3$ | F | Cl | $CH_3$ |
| 212 | $CH_2CH_3$ | F | Cl | $CH_3$ |
| 213 | $CH(CH_3)_2$ | F | Cl | $CH_3$ |
| 214 | $CH_3$ | Cl | Cl | $CH_3$ |
| 215 | $CH_2CH_3$ | Cl | Cl | $CH_3$ |
| 216 | $CH_3$ | F | Br | $CH_3$ |
| 217 | $CH_3$ | F | $CH_3$ | $CH_3$ |
| 218 | $CH_3$ | F | CN | $CH_3$ |
| 219 | $CH_2CH_3$ | F | Br | $CH_3$ |
| 220 | $CH_2CH_3$ | F | $CH_3$ | $CH_3$ |
| 221 | $CH_2CH_3$ | F | CN | $CH_3$ |
| 222 | $CH_3$ | Cl | CN | $CH_3$ |
| 223 | $CH_3$ | F | Cl | CHO |
| 224 | $CH_2CH_3$ | F | Cl | CHO |
| 225 | $CH(CH_3)_2$ | F | Cl | CHO |
| 226 | $CH_3$ | Cl | Cl | CHO |
| 227 | $CH_2CH_3$ | Cl | Cl | CHO |
| 228 | $CH_3$ | F | Br | CHO |
| 229 | $CH_3$ | F | $CH_3$ | CHO |
| 230 | $CH_3$ | F | CN | CHO |
| 231 | $CH_2CH_3$ | F | Br | CHO |
| 232 | $CH_2CH_3$ | F | $CH_3$ | CHO |
| 233 | $CH_2CH_3$ | F | CN | CHO |
| 234 | $CH_3$ | Cl | CN | CHO |
| 235 | $CH_3$ | F | Cl | $NH_2$ |
| 236 | $CH_2CH_3$ | F | Cl | $NH_2$ |
| 237 | $CH(CH_3)_2$ | F | Cl | $NH_2$ |
| 238 | $CH_3$ | Cl | Cl | $NH_2$ |
| 239 | $CH_2CH_3$ | Cl | Cl | $NH_2$ |
| 240 | $CH_3$ | F | Br | $NH_2$ |
| 241 | $CH_3$ | F | $CH_3$ | $NH_2$ |
| 242 | $CH_3$ | F | CN | $NH_2$ |
| 243 | $CH_2CH_3$ | F | Br | $NH_2$ |
| 244 | $CH_2CH_3$ | F | $CH_3$ | $NH_2$ |
| 245 | $CH_2CH_3$ | F | CN | $NH_2$ |
| 246 | $CH_3$ | Cl | CN | $NH_2$ |
| 247 | $CH_3$ | F | Cl | $CH_3$ |
| 248 | $CH_2CH_3$ | F | Cl | $CH_3$ |
| 249 | $CH(CH_3)_2$ | F | Cl | $CH_3$ |
| 250 | $CH_3$ | Cl | Cl | $CH_3$ |
| 251 | $CH_2CH_3$ | Cl | Cl | $CH_3$ |

TABLE 6-continued

Compounds of the formulae $V_1$, $V_2$, $II_1$ and $III_1$

| | | | | |
|---|---|---|---|---|
| 252 | CH₃ | F | Br | CH₃ |
| 253 | CH₃ | F | CH₃ | CH₃ |
| 254 | CH₃ | F | CN | CH₃ |
| 255 | CH₂CH₃ | F | Br | CH₃ |
| 256 | CH₂CH₃ | F | CH₃ | CH₃ |
| 257 | CH₂CH₃ | F | CN | CH₃ |
| 258 | CH₃ | Cl | CN | CH₃ |
| 259 | CH₃ | F | NO₂ | OH |
| 260 | CH₂CH₃ | F | NO₂ | OH |
| 261 | CH(CH₃)₂ | F | NO₂ | OH |
| 262 | CH₃ | Cl | NO₂ | OH |
| 263 | CH₂CH₃ | Cl | NO₂ | OH |
| 264 | CH₃ | F | NO₂ | OCH₃ |
| 265 | CH₂CH₃ | F | NO₂ | OCH₃ |
| 266 | CH(CH₃)₂ | F | NO₂ | OCH₃ |
| 267 | CH₃ | Cl | NO₂ | OCH₃ |
| 268 | CH₂CH₃ | Cl | NO₂ | OCH₃ |
| 269 | CH₃ | F | NO₂ | Br |
| 270 | CH₂CH₃ | F | NO₂ | Br |
| 271 | CH(CH₃)₂ | F | NO₂ | Br |
| 272 | CH₃ | Cl | NO₂ | Br |
| 273 | CH₂CH₃ | Cl | NO₂ | Br |
| 274 | CH₃ | F | NO₂ | COOH |
| 275 | CH₂CH₃ | F | NO₂ | COOH |
| 276 | CH(CH₃)₂ | F | NO₂ | COOH |
| 277 | CH₃ | Cl | NO₂ | COOH |
| 278 | CH₂CH₃ | Cl | NO₂ | COOH |
| 279 | CH₃ | F | NO₂ | CH₃ |
| 280 | CH₂CH₃ | F | NO₂ | CH₃ |
| 281 | CH(CH₃)₂ | F | NO₂ | CH₃ |
| 282 | CH₃ | Cl | NO₂ | CH₃ |
| 283 | CH₂CH₃ | Cl | NO₂ | CH₃ |
| 284 | CH₃ | F | NO₂ | Cl |
| 285 | CH₂CH₃ | F | NO₂ | Cl |
| 286 | CH(CH₃)₂ | F | NO₂ | Cl |
| 287 | CH₃ | Cl | NO₂ | Cl |
| 288 | CH₂CH₃ | Cl | NO₂ | Cl |
| 289 | CH₃ | F | NO₂ | NH₂ |
| 290 | CH₂CH₃ | F | NO₂ | NH₂ |
| 291 | CH(CH₃)₂ | F | NO₂ | NH₂ |
| 292 | CH₃ | Cl | NO₂ | NH₂ |
| 293 | CH₂CH₃ | Cl | NO₂ | NH₂ |
| 294 | CH₂CH₃ | F | NH₂ | OH |
| 295 | CH(CH₃)₂ | F | NH₂ | OH |
| 296 | CH₃ | Cl | NH₂ | OH |
| 297 | CH₂CH₃ | Cl | NH₂ | OH |
| 298 | CH₃ | F | NH₂ | OCH₃ |
| 299 | CH₂CH₃ | F | NH₂ | OCH₃ |
| 300 | CH(CH₃)₂ | F | NH₂ | OCH₃ |
| 301 | CH₃ | Cl | NH₂ | OCH₃ |
| 302 | CH₂CH₃ | Cl | NH₂ | OCH₃ |
| 303 | CH₃ | F | NH₂ | COOCH₃ |
| 304 | CH₂CH₃ | F | NH₂ | COOCH₃ |
| 305 | CH(CH₃)₂ | F | NH₂ | COOCH₃ |
| 306 | CH₃ | Cl | NH₂ | COOCH₃ |
| 307 | CH₂CH₃ | Cl | NH₂ | COOCH₃ |
| 308 | CH₃ | F | NH₂ | CH₃ |
| 309 | CH₂CH₃ | F | NH₂ | CH₃ |
| 310 | CH(CH₃)₂ | F | NH₂ | CH₃ |
| 311 | CH₃ | Cl | NH₂ | CH₃ |
| 312 | CH₂CH₃ | Cl | NH₂ | CH₃ |
| 313 | CH₃ | F | SH | H |
| 314 | CH₃ | F | SH | NO₂ |
| 315 | CH₃ | F | SH | NH₂ |
| 316 | CH₂CH₃ | F | SH | H |
| 317 | CH₂CH₃ | F | SH | NO₂ |
| 318 | CH₂CH₃ | F | SH | NH₂ |
| 319 | CH₃ | Cl | SH | H |
| 320 | CH₃ | Cl | SH | NO₂ |
| 321 | CH₃ | Cl | SH | NH₂ |
| 322 | CH₂CH₃ | Cl | SH | H |
| 323 | CH₂CH₃ | Cl | SH | NO₂ |
| 324 | CH₂CH₃ | Cl | SH | NH₂ |
| 325 | CH₃ | H | NO₂ | H |
| 326 | CH₂CH₃ | H | NO₂ | H |
| 327 | CH₃ | H | NH₂ | H |
| 328 | CH₂CH₃ | H | NH₂ | H |
| 329 | CH₃ | H | NH₂ | Br |
| 330 | CH₂CH₃ | H | NH₂ | Br |
| 331 | CH₃ | H | NO₂ | F |
| 332 | CH₂CH₃ | H | NO₂ | F |
| 333 | CH₃ | H | NO₂ | Cl |
| 334 | CH₂CH₃ | H | NO₂ | Cl |
| 335 | CH₃ | H | NO₂ | Br |
| 336 | CH₂CH₃ | H | NO₂ | Br |
| 337 | CH₃ | H | NO₂ | NH₂ |
| 338 | CH₂CH₃ | H | NO₂ | NH₂ |
| 339 | CH₃ | H | OH | H |
| 340 | CH₂CH₃ | H | OH | H |
| 341 | CH₃ | H | OH | NO₂ |
| 342 | CH₂CH₃ | H | OH | NO₂ |
| 343 | CH₃ | H | OH | NH₂ |
| 344 | CH₂CH₃ | H | OH | NH₂ |
| 345 | CH₃ | H | F | NO₂ |
| 346 | CH₂CH₃ | H | F | NO₂ |
| 347 | CH₃ | H | Cl | NO₂ |
| 348 | CH₂CH₃ | H | Cl | NO₂ |
| 349 | CH₃ | H | SH | NO₂ |
| 350 | CH₂CH₃ | H | SH | NO₂ |
| 351 | H | F | Cl | H |
| 352 | H | Cl | Cl | H |
| 353 | H | F | H | F |
| 354 | H | Cl | H | Cl |
| 355 | H | F | Br | H |
| 356 | H | F | CH₃ | H |
| 357 | H | Cl | Br | H |
| 358 | H | F | Cl | OCH₃ |
| 359 | H | Cl | Cl | OCH₃ |
| 360 | H | F | Cl | COOCH₂CH₃ |
| 361 | H | Cl | Cl | COOCH₃ |
| 362 | H | F | Br | COOCH₂CH₃ |
| 363 | H | F | Cl | NO₂ |
| 364 | H | Cl | Cl | NO₂ |
| 365 | H | F | NO₂ | F |
| 366 | H | F | Cl | CH₃ |
| 367 | H | Cl | NO₂ | Cl |
| 368 | H | F | NH₂ | OCH₃ |
| 369 | H | F | Cl | NH₂ |
| 370 | H | Cl | Cl | NH₂ |
| 371 | H | F | Br | NO₂ |
| 372 | H | F | Cl | Br |
| 373 | H | F | Cl | I |
| 374 | H | Cl | Cl | Br |
| 375 | H | F | Cl | OH |
| 376 | H | Cl | Cl | OH |
| 377 | H | F | NH₂ | H |
| 378 | H | F | Cl | SH |
| 379 | H | F | OCH₃ | H |
| 380 | H | Cl | OCH₃ | H |
| 381 | H | F | OH | NO₂ |
| 382 | H | H | NH₂ | H |
| 383 | H | H | Cl | H |
| 384 | H | H | F | NO₂ |
| 385 | H | H | Cl | NO₂ |
| 386 | H | H | H | NH₂ |

TABLE 7

Compounds of the formula $I_{36}$ $(I_{36})$

| Comp. No. | $R_3$ | $R_4$ | $R_5$ | $R_6$ |
|---|---|---|---|---|
| $I_{36}$.001 | $CH_3$ | F | F | H |
| $I_{36}$.002 | $CH_2CH_3$ | F | F | H |
| $I_{36}$.003 | $CH_3$ | F | F | $NO_2$ |
| $I_{36}$.004 | $CH_2CH_3$ | F | F | $NO_2$ |
| $I_{36}$.005 | $CH_3$ | F | H | F |
| $I_{36}$.006 | $CH_2CH_3$ | F | H | F |
| $I_{36}$.007 | $CH_3$ | F | $NO_2$ | F |
| $I_{36}$.008 | $CH_2CH_3$ | F | $NO_2$ | F |
| $I_{36}$.009 | $CH_3$ | F | $NO_2$ | OH |
| $I_{36}$.010 | $CH_2CH_3$ | F | $NO_2$ | OH |
| $I_{36}$.011 | $CH_3$ | F | $NO_2$ | SH |
| $I_{36}$.012 | $CH_2CH_3$ | F | $NO_2$ | SH |
| $I_{36}$.013 | $CH_3$ | F | $NO_2$ | $NH_2$ |
| $I_{36}$.014 | $CH_2CH_3$ | F | $NO_2$ | $NH_2$ |
| $I_{36}$.015 | $CH_3$ | Cl | Cl | $NO_2$ |
| $I_{36}$.016 | $CH_2CH_3$ | Cl | Cl | $NO_2$ |
| $I_{36}$.017 | $CH_3$ | Cl | H | Cl |
| $I_{36}$.018 | $CH_2CH_3$ | Cl | H | Cl |
| $I_{36}$.019 | $CH_3$ | Cl | $NO_2$ | Cl |
| $I_{36}$.020 | $CH_2CH_3$ | Cl | $NO_2$ | Cl |
| $I_{36}$.021 | $CH_3$ | Cl | $NO_2$ | OH |
| $I_{36}$.022 | $CH_2CH_3$ | Cl | $NO_2$ | OH |
| $I_{36}$.023 | $CH_3$ | Cl | $NO_2$ | SH |
| $I_{36}$.024 | $CH_2CH_3$ | Cl | $NO_2$ | SH |
| $I_{36}$.025 | $CH_3$ | Cl | $NO_2$ | $NH_2$ |
| $I_{36}$.026 | $CH_2CH_3$ | Cl | $NO_2$ | $NH_2$ |
| $I_{36}$.027 | $CH_3$ | F | $NO_2$ | $OCH_3$ |
| $I_{36}$.028 | $CH_2CH_3$ | F | $NO_2$ | $OCH_3$ |
| $I_{36}$.029 | $CH_3$ | Cl | $NO_2$ | $OCH_3$ |
| $I_{36}$.030 | $CH_2CH_3$ | Cl | $NO_2$ | $OCH_3$ |
| $I_{36}$.031 | $CH_3$ | F | $NH_2$ | $OCH_3$ |
| $I_{36}$.032 | $CH_2CH_3$ | F | $NH_2$ | $OCH_3$ |
| $I_{36}$.033 | $CH_3$ | Cl | $NH_2$ | $OCH_3$ |
| $I_{36}$.034 | $CH_2CH_3$ | Cl | $NH_2$ | $OCH_3$ |
| $I_{36}$.035 | $CH_3$ | F | $NH_2$ | OH |
| $I_{36}$.036 | $CH_2CH_3$ | Cl | $NH_2$ | OH |
| $I_{36}$.037 | $CH_2CH_3$ | F | $NH_2$ | OH |
| $I_{36}$.038 | $CH_3$ | Cl | $NH_2$ | OH |
| $I_{36}$.039 | $CH_3$ | F | Cl | $NH_2$ |
| $I_{36}$.040 | $CH_2CH_3$ | F | Cl | $NH_2$ |
| $I_{36}$.041 | $CH_3$ | Cl | Cl | $NH_2$ |
| $I_{36}$.042 | $CH_2CH_3$ | Cl | Cl | $NH_2$ |
| $I_{36}$.043 | $CH_3$ | F | Br | $NO_2$ |
| $I_{36}$.044 | $CH_2CH_3$ | F | Br | $NO_2$ |
| $I_{36}$.045 | $CH_3$ | F | $CH_3$ | $NO_2$ |
| $I_{36}$.046 | $CH_2CH_3$ | F | $CH_3$ | $NO_2$ |
| $I_{36}$.047 | $CH_3$ | F | Br | $NH_2$ |
| $I_{36}$.048 | $CH_2CH_3$ | F | Br | $NH_2$ |
| $I_{36}$.049 | $CH_3$ | F | $CH_3$ | $NH_2$ |
| $I_{36}$.050 | $CH_2CH_3$ | F | $CH_3$ | $NH_2$ |
| $I_{36}$.051 | $CH_3$ | F | OH | $NO_2$ |
| $I_{36}$.052 | $CH_3$ | Cl | OH | $NO_2$ |
| $I_{36}$.053 | $CH_2CH_3$ | F | OH | $NO_2$ |
| $I_{36}$.054 | $CH_2CH_3$ | Cl | OH | $NO_2$ |
| $I_{36}$.055 | $CH_3$ | F | SH | $NO_2$ |
| $I_{36}$.056 | $CH_3$ | Cl | SH | $NO_2$ |
| $I_{36}$.057 | $CH_2CH_3$ | F | SH | $NO_2$ |
| $I_{36}$.058 | $CH_2CH_3$ | Cl | SH | $NO_2$ |
| $I_{36}$.059 | $CH_3$ | F | OH | $NH_2$ |
| $I_{36}$.060 | $CH_3$ | Cl | OH | $NH_2$ |
| $I_{36}$.061 | $CH_2CH_3$ | F | OH | $NH_2$ |
| $I_{36}$.062 | $CH_2CH_3$ | Cl | OH | $NH_2$ |
| $I_{36}$.063 | $CH_3$ | F | SH | $NH_2$ |
| $I_{36}$.064 | $CH_3$ | Cl | SH | $NH_2$ |
| $I_{36}$.065 | $CH_2CH_3$ | F | SH | $NH_2$ |
| $I_{36}$.066 | $CH_2CH_3$ | Cl | SH | $NH_2$ |
| $I_{36}$.067 | $CH_3$ | F | $NO_2$ | Br |
| $I_{36}$.068 | $CH_2CH_3$ | F | $NO_2$ | Br |
| $I_{36}$.069 | $CH_3$ | F | $NO_2$ | COOH |
| $I_{36}$.070 | $CH_2CH_3$ | F | $NO_2$ | COOH |
| $I_{36}$.071 | $CH_3$ | Cl | $NO_2$ | Br |
| $I_{36}$.072 | $CH_2CH_3$ | Cl | $NO_2$ | Br |
| $I_{36}$.073 | $CH_3$ | Cl | $NO_2$ | COOH |
| $I_{36}$.074 | $CH_2CH_3$ | Cl | $NO_2$ | COOH |
| $I_{36}$.075 | $CH_3$ | F | $NH_2$ | COOH |
| $I_{36}$.076 | $CH_2CH_3$ | F | $NH_2$ | COOH |
| $I_{36}$.077 | $CH_3$ | Cl | $NH_2$ | COOH |
| $I_{36}$.078 | $CH_2CH_3$ | Cl | $NH_2$ | COOH |
| $I_{36}$.079 | $CH_3$ | H | F | H |
| $I_{36}$.080 | $CH_2CH_3$ | H | F | H |
| $I_{36}$.081 | $CH_3$ | H | F | $NO_2$ |
| $I_{36}$.082 | $CH_2CH_3$ | H | F | $NO_2$ |
| $I_{36}$.083 | $CH_3$ | H | Cl | H |
| $I_{36}$.084 | $CH_2CH_3$ | H | Cl | H |
| $I_{36}$.085 | $CH_3$ | H | Cl | $NO_2$ |
| $I_{36}$.086 | $CH_2CH_3$ | H | Cl | $NO_2$ |
| $I_{36}$.087 | $CH_3$ | H | $NO_2$ | H |
| $I_{36}$.088 | $CH_2CH_3$ | H | $NO_2$ | H |
| $I_{36}$.089 | $CH_3$ | H | $NO_2$ | F |
| $I_{36}$.090 | $CH_2CH_3$ | H | $NO_2$ | F |
| $I_{36}$.091 | $CH_3$ | H | $NO_2$ | Cl |
| $I_{36}$.092 | $CH_2CH_3$ | H | $NO_2$ | Cl |
| $I_{36}$.093 | $CH_3$ | H | $NO_2$ | OH |
| $I_{36}$.094 | $CH_2CH_3$ | H | $NO_2$ | OH |
| $I_{36}$.095 | $CH_3$ | H | $NH_2$ | H |
| $I_{36}$.096 | $CH_2CH_3$ | H | $NH_2$ | H |
| $I_{36}$.097 | $CH_3$ | H | $NO_2$ | $NH_2$ |
| $I_{36}$.098 | $CH_2CH_3$ | H | $NO_2$ | $NH_2$ |
| $I_{36}$.099 | $CH_3$ | H | $NH_2$ | H |
| $I_{36}$.100 | $CH_2CH_3$ | H | $NH_2$ | H |
| $I_{36}$.101 | $CH_3$ | F | Cl | OH |
| $I_{36}$.102 | $CH_2CH_3$ | F | Cl | OH |
| $I_{36}$.103 | $CH_3$ | Cl | Cl | OH |
| $I_{36}$.104 | $CH_2CH_3$ | Cl | Cl | OH |
| $I_{36}$.105 | $CH_3$ | H | Cl | OH |
| $I_{36}$.106 | $CH_2CH_3$ | H | Cl | OH |
| $I_{36}$.107 | $CH_3$ | F | Cl | $NO_2$ |
| $I_{36}$.108 | $CH_2CH_3$ | F | Cl | $NO_2$ |
| $I_{36}$.109 | $CH_3$ | F | Cl | I |
| $I_{36}$.110 | $CH_2CH_3$ | F | Cl | I |
| $I_{36}$.111 | $CH_3$ | Cl | Cl | I |
| $I_{36}$.112 | $CH_2CH_3$ | Cl | Cl | I |

TABLE 8

Compounds of the formulae $V_3$, $V_4$, $II_2$ and $III_2$ ($V_3$)
($V_4$)
($II_2$)
($III_2$)

| Comp. No. $V_n$ or $II_2$ and $III_2$ n = 3 or 4 | $R_3$ | $R_4$ | $R_{61}$ |
|---|---|---|---|
| 001 | H | F | H |
| 002 | $CH_3$ | F | H |
| 003 | $CH_2CH_3$ | F | H |
| 004 | $CH(CH_3)_2$ | F | H |
| 005 | H | Cl | H |
| 006 | $CH_3$ | Cl | H |
| 007 | $CH_2CH_3$ | Cl | H |
| 008 | $CH(CH_3)_2$ | Cl | H |
| 009 | $CH_2CCH$ | F | H |
| 010 | H | F | $CH(CH_3)_2$ |
| 011 | $CH_3$ | F | $CH(CH_3)_2$ |
| 012 | $CH_2CH_3$ | F | $CH(CH_3)_2$ |
| 013 | $CH(CH_3)_2$ | F | $CH(CH_3)_2$ |
| 014 | H | Cl | $CH(CH_3)_2$ |
| 015 | $CH_3$ | Cl | $CH(CH_3)_2$ |
| 016 | $CH_2CH_3$ | Cl | $CH(CH_3)_2$ |
| 017 | $CH(CH_3)_2$ | Cl | $CH(CH_3)_2$ |
| 018 | H | F | $CH_2CHCH_2$ |
| 019 | $CH_3$ | F | $CH_2CHCH_2$ |
| 020 | $CH_2CH_3$ | F | $CH_2CHCH_2$ |
| 021 | $CH(CH_3)_2$ | F | $CH_2CHCH_2$ |
| 022 | H | Cl | $CH_2CHCH_2$ |
| 023 | $CH_3$ | Cl | $CH_2CHCH_2$ |
| 024 | $CH_2CH_3$ | Cl | $CH_2CHCH_2$ |
| 025 | $CH(CH_3)_2$ | Cl | $CH_2CHCH_2$ |
| 026 | $CH_3$ | F | $CH_2CCH$ |
| 027 | $CH_2CH_3$ | F | $CH_2CCH$ |
| 028 | $CH(CH_3)_2$ | F | $CH_2CCH$ |
| 029 | $CH_3$ | Cl | $CH_2CCH$ |
| 030 | $CH_2CH_3$ | Cl | $CH_2CCH$ |
| 031 | $CH(CH_3)_2$ | Cl | $CH_2CCH$ |
| 032 | $CH_3$ | F | $CH_2C_6H_5$ |
| 033 | $CH_2CH_3$ | F | $CH_2C_6H_5$ |
| 034 | H | F | $CH_2COOH$ |
| 035 | $CH_3$ | F | $CH_2COOH$ |
| 036 | $CH_2CH_3$ | F | $CH_2COOH$ |
| 037 | $CH(CH_3)_2$ | F | $CH_2COOH$ |
| 038 | H | Cl | $CH_2COOH$ |
| 039 | $CH_3$ | Cl | $CH_2COOH$ |
| 040 | $CH_2CH_3$ | Cl | $CH_2COOH$ |
| 041 | $CH(CH_3)_2$ | Cl | $CH_2COOH$ |
| 042 | $CH_3$ | F | $CH(CH_3)COOCH_3$ |
| 043 | $CH_2CH_3$ | F | $CH(CH_3)COOCH_3$ |
| 044 | $CH(CH_3)_2$ | F | $CH(CH_3)COOCH_3$ |
| 045 | $CH_3$ | Cl | $CH(CH_3)COOCH_3$ |
| 046 | $CH_2CH_3$ | Cl | $CH(CH_3)COOCH_3$ |
| 047 | $CH(CH_3)_2$ | Cl | $CH(CH_3)COOCH_3$ |
| 048 | H | H | H |
| 049 | $CH_3$ | H | H |
| 050 | $CH_2CH_3$ | H | H |
| 051 | $CH(CH_3)_3$ | H | H |
| 052 | H | H | $CH_2COOH$ |
| 053 | $CH_3$ | H | $CH_2COOH$ |
| 054 | $CH_2CH_3$ | H | $CH_2COOH$ |
| 055 | $CH(CH_3)_2$ | H | $CH_2COOH$ |

TABLE 9

Compounds of the formulae $II_3$, $V_5$, $V_6$ and $III_3$

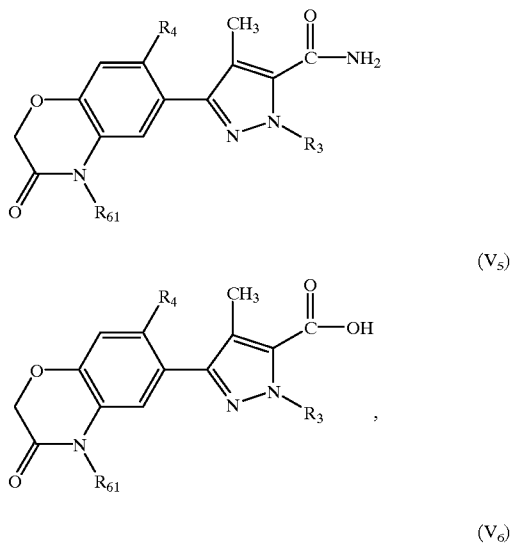

($II_3$)
($V_5$)
($V_6$)

TABLE 9-continued

Compounds of the formulae II₃, V₅, V₆ and III₃

(Structure III₃ shown: benzoxazinone fused to pyrazole with R₄, CH₃, COOCH₃, R₃, R₆₁ substituents)

(Structure shown with NH₂ group: benzoxazinone-pyrazole with R₄, CH₃, NH₂, R₃, R₆₁ substituents)

| Comp. No. V_n or II₃ and III₃ n = 5 or 6 | R₃ | R₄ | R₆₁ |
|---|---|---|---|
| 001 | H | F | H |
| 002 | CH₃ | F | H |
| 003 | CH₂CH₃ | F | H |
| 004 | CH(CH₃)₂ | F | H |
| 005 | H | Cl | H |
| 006 | CH₃ | Cl | H |
| 007 | CH₂CH₃ | Cl | H |
| 008 | CH(CH₃)₂ | Cl | H |
| 009 | H | F | CH(CH₃)₂ |
| 010 | CH₃ | F | CH(CH₃)₂ |
| 011 | CH₂CH₃ | F | CH(CH₃)₂ |
| 012 | CH(CH₃)₂ | F | CH(CH₃)₂ |
| 013 | H | Cl | CH(CH₃)₂ |
| 014 | CH₃ | Cl | CH(CH₃)₂ |
| 015 | CH₂CH₃ | Cl | CH(CH₃)₂ |
| 016 | CH(CH₃)₂ | Cl | CH(CH₃)₂ |
| 017 | H | F | CH₂CHCH₂ |
| 018 | CH₃ | F | CH₂CHCH₂ |
| 019 | CH₂CH₃ | F | CH₂CHCH₂ |
| 020 | CH(CH₃)₂ | F | CH₂CHCH₂ |
| 021 | H | Cl | CH₂CHCH₂ |
| 022 | CH₃ | Cl | CH₂CHCH₂ |
| 023 | CH₂CH₃ | Cl | CH₂CHCH₂ |
| 024 | CH(CH₃)₂ | Cl | CH₂CHCH₂ |
| 025 | CH₃ | F | CH₂CCH |
| 026 | CH₂CH₃ | F | CH₂CCH |
| 027 | CH(CH₃)₂ | F | CH₂CCH |
| 028 | CH₃ | Cl | CH₂CCH |
| 029 | CH₂CH₃ | Cl | CH₂CCH |
| 030 | CH(CH₃)₂ | Cl | CH₂CCH |
| 031 | H | F | CH₂COOH |
| 032 | CH₃ | F | CH₂COOH |
| 033 | CH₂CH₃ | F | CH₂COOH |
| 034 | CH(CH₃)₂ | F | CH₂COOH |
| 035 | H | Cl | CH₂COOH |
| 036 | CH₃ | Cl | CH₂COOH |
| 037 | CH₂CH₃ | Cl | CH₂COOH |
| 038 | CH(CH₃)₂ | Cl | CH₂COOH |
| 039 | CH₃ | F | CH(CH₃)COOCH₃ |
| 040 | CH₂CH₃ | F | CH(CH₃)COOCH₃ |
| 041 | CH(CH₃)₂ | F | CH(CH₃)COOCH₃ |
| 042 | CH₃ | Cl | CH(CH₃)COOCH₃ |
| 043 | CH₂CH₃ | Cl | CH(CH₃)COOCH₃ |
| 044 | CH(CH₃)₂ | Cl | CH(CH₃)COOCH₃ |
| 045 | H | H | H |
| 046 | CH₃ | H | H |
| 047 | CH₂CH₃ | H | H |
| 048 | CH(CH₃)₂ | H | H |
| 049 | H | H | CH₂COOH |
| 050 | CH₃ | H | CH₂COOH |
| 051 | CH₂CH₃ | H | CH₂COOH |
| 052 | CH(CH₃)₂ | H | CH₂COOH |

TABLE 10

Compounds of the formulae III₄, III₅ and III₆

(III₄) (Structure: dihydrobenzofuran-pyrazole with R₄, R₅, CH₃, NH₂, R₃, R₇₂)

(III₅) (Structure: benzofuran-pyrazole with R₄, R₅, CH₃, NH₂, R₃, R₇₂)

(III₆) (Structure: dimethyl dihydrobenzofuran-pyrazole with R₄, R₅, CH₃, NH₂, R₃, R₇₂, CH₃)

| Comp. No. III_n n = 4–6 | R₃ | R₄ | R₅ | R₇₂ |
|---|---|---|---|---|
| 001 | CH₃ | H | Cl | CH₃ |
| 002 | CH₃ | H | Cl | CH₂OH |
| 003 | CH₃ | H | Cl | COOH |
| 004 | CH₃ | F | Cl | CH₃ |
| 005 | CH₃ | F | Cl | CH₂OH |
| 006 | CH₃ | F | Cl | CH₂Cl |
| 007 | CH₃ | F | Cl | COOH |
| 008 | CH₃ | F | Cl | COOCH₃ |
| 009 | CH₃ | F | Br | CH₂OH |
| 010 | CH₃ | F | Br | COOH |
| 011 | C₂H₅ | F | Cl | CH₃ |
| 012 | C₂H₅ | F | Cl | CH₂OH |
| 013 | CH₃ | Cl | Cl | CH₃ |
| 014 | CH₃ | Cl | Cl | CH₂OH |
| 015 | CH₃ | Cl | Cl | COOH |

TABLE 11

Prepared compounds from the above Tables 1–10 together with physicochemical data.

| Comp No. | Physicochemical data |
|---|---|
| I$_1$.001 | m.p. 152–153° C. |
| I$_1$.006 | m.p. 155–156° C. |
| I$_1$.027 | m.p. 145–146° C. |
| I$_1$.108 | oil (recem.) |
| I$_1$.118 | resin |
| I$_1$.130 | m.p. 240–242° C. |
| I$_1$.134 | m.p. 127–128° C. |
| I$_1$.140 | m.p. 88–89° C. |
| I$_1$.151 | m.p. 129–131° C. |
| I$_1$.159 | m.p. 57–58° C. |
| I$_1$.219 | m.p. 57–58° C. |
| I$_1$.220 | m.p. 183–184° C. |
| I$_1$.221 | resin |
| I$_1$.222 | m.p. 57–58° C. |
| I$_1$.223 | m.p. 151–152° C. |
| I$_3$.001 | resin |
| I$_3$.006 | m.p. 227–228° C. |
| I$_3$.027 | m.p. 256–257° C. |
| I$_3$.130 | m.p. 179–185° C. |
| I$_3$.140 | m.p. 92–93° C. |
| I$_3$.151 | m.p. 149–151° C. |
| I$_3$.159 | oil |
| I$_3$.219 | resin |
| I$_5$.001 | m.p. 174–175° C. |
| I$_6$.001 | m.p. 163–164° C. |
| I$_{36}$.015 | m.p. 119–120° C. |
| I$_{36}$.017 | m.p. 113–114° C. |
| I$_{36}$.019 | m.p. 234–235° C. |
| I$_{36}$.033 | m.p. 243–244° C. |
| I$_{36}$.039 | m.p. 133–134° C. |
| I$_{36}$.041 | m.p. 90–91° C. |
| I$_{36}$.101 | m.p. 172–173° C. |
| I$_{36}$.103 | m.p. 263–265° C. |
| I$_{36}$.107 | m.p. 137–138° C. |
| I$_{36}$.109 | m.p. 144–145° C. |
| V$_1$.071 | m.p. 135–137° C. |
| V$_1$.358 | solid |
| V$_2$.071 | solid |
| II$_1$.071 | m.p. 224–226° C. |

Formulation Examples of Active Ingredients of the Formula I (%=per cent by weight)

| F1. Emulsion concentrates | a) | b) | c) | d) |
|---|---|---|---|---|
| Active ingredient of Tables 1–5 and 7 | 5% | 10% | 25% | 50% |
| Calcium dodecylbenzenesulfonate | 6% | 8% | 6% | 8% |
| Castor oil polyglycol ether (36 mol of EO) | 4% | — | 4% | 4% |
| Octylphenol polyglycol ether (7–8 mol of EO) | — | 4% | — | 2% |
| Cyclohexanone | — | — | 10% | 20% |
| Aromatic hydrocarbon mixture C$_9$–C$_{12}$ | 85% | 78% | 55% | 16% |

Emulsions of any desired concentration can be prepared from such concentrates by diluting them with water.

| F2. Solutions | a) | b) | c) | d) |
|---|---|---|---|---|
| Active ingredient of Tables 1–5 and 7 | 5% | 10% | 50% | 90% |
| 1-methoxy-3-(3-methoxypropoxy)propane | — | 20% | 20% | — |
| Polyethylene glycol MW 400 | 20% | 10% | — | — |
| N-methyl-2-pyrrolidone | — | — | 30% | 10% |
| Aromatic hydrocarbon mixture C$_9$–C$_{12}$ | 75% | 60% | — | — |

The solutions are suitable for use in the form of microdrops.

| F3. Wettable powders | a) | b) | c) | d) |
|---|---|---|---|---|
| Active ingredient of Tables 1–5 and 7 | 5% | 25% | 50% | 80% |
| Sodium lignosulfonate | 4% | — | 3% | — |
| Sodium lauryl sulfate | 2% | 3% | — | 4% |
| Sodium diisobutylnaphthalenesulfonate | — | 6% | 5% | 6% |
| Octylphenyl polyglycol ether (7–8 Mol EO) | — | 1% | 2% | — |
| Highly disperse silica | 1% | 3% | 5% | 10% |
| Kaolin | 88% | 62% | 35% | — |

The active ingredient is mixed thoroughly with the additives and the mixture is ground thoroughly in a suitable mill. This gives wettable powders which can be diluted with water to give suspensions of any desired concentration.

| F4. Coated granules | a) | b) | c) |
|---|---|---|---|
| Active ingredient of Tables 1–5 and 7 | 0.1% | 5% | 15% |
| Hghly-disperse silica | 0.9% | 2% | 2% |
| Inorganic carrier material (Ø 0.1–1 mm), for example CaCO$_3$ or SiO$_2$ | 99.0% | 93% | 83% |

The active ingredient is dissolved in methylene chloride, the solution is sprayed onto the carrier, and the solvent is subsequently evaporated in vacuo.

| F5. Coated granules | a) | b) | c) |
|---|---|---|---|
| Active ingredient of Tables 1–5 and 7 | 0.1% | 5% | 15% |
| Polyethylene glycol MW 200 | 1.0% | 2% | 3% |
| Highiy disperse silica | 0.9% | 1% | 2% |
| Inorganic carrier material (Ø 0.1–1 mm), for example CaCO$_3$ or SiO$_2$ | 98.0% | 92% | 80% |

In a mixer, the finely ground active ingredient is applied uniformly to the carrier material which has been moistened with polyethylene glycol. In this manner, dust-free coated granules are obtained.

| F6. Extruder granules | a) | b) | c) | d) |
|---|---|---|---|---|
| Active ingredient of Tables 1–5 and 7 | 0.1% | 3% | 5% | 15% |
| Sodium lignosulfonate | 1.5% | 2% | 3% | 4% |
| Carboxymethylcellulose | 1.4% | 2% | 2% | 2% |
| Kaolin | 97.0% | 93% | 90% | 79% |

The active ingredient is mixed with the additives, and the mixture is ground and moistened with water. This mixture is extruded and subsequently dried in a stream of air.

| F7. Dusts | a) | b) | c) |
|---|---|---|---|
| Active ingredient of Tables 1–5 and 7 | 0.1% | 1% | 5% |
| Talc | 39.9% | 49% | 35% |
| Kaolin | 60.0% | 50% | 60% |

Ready-to-use dusts obtained by mixing the active ingredient with the carriers and grinding the mixture on a suitable mill.

| F8. Suspensions concentrates | a) | b) | c) | d) |
|---|---|---|---|---|
| Active ingredient of Tables 1–5 and 7 | 3% | 10% | 25% | 50% |
| Ethylene glycol | 5% | 5% | 5% | 5% |
| Nonylphenyl polyglycol ether (15 mols of EO) | — | 1% | 2% | — |
| Sodium lignosulfonate | 3% | 3% | 4% | 5% |
| Carboxymethylcellulose | 1% | 1% | 1% | 1% |
| 37% aqueous formladehyde solution | 0.2% | 0.2% | 0.2% | 0.2% |
| Silicone oil emulsion | 0.8% | 0.8% | 0.8% | 0.8% |
| Water | 87% | 79% | 62% | 38% |

The finely ground active ingredient is mixed intimately with the additives. This gives a suspension concentrate from which suspensions of any desired concentration can be prepared by diluting it with water.

Biological Examples

EXAMPLE B1
Herbicidal Action Before Emergence of the Plants (Pre-emergence Action)

Monocotyledoneous and dicotyledoneous test plants are grown in standard soil in plastic pots. Immediately after sowing, the test substances are sprayed on in the form of an aqueous suspension or emulsion, prepared from a 25% emulsion concentrate (Example F1, c)), which corresponds to a dosage of 500 g of a.i./ha (500 l of water/ha). The test plants are subsequently grown in the greenhouse under optimal conditions. After a test period of 3 weeks, the experiment is evaluated on a nine-step scale (1=complete damage, 9=no action). Score figures of 1 to 4 (in particular 1 to 3) denote a good to very good herbicidal action.

Test plants: Avena, Setaria, Solanum, Stellaria, Ipomoea.

The compounds according to the invention have good herbicidal activity.

Examples of the good herbicidal activity of the compounds of the formula I are given in Table B1.

TABLE B1

| | Pre-emergence action: | | | | | |
|---|---|---|---|---|---|---|
| Active ingredient No. | Test plant: | | | | | Dose [g of a.i./ha] |
| | Avena | Setaria | Solanum | Stellaria | Ipomoea | |
| $I_1$.001 | 4 | 1 | 1 | 6 | 3 | 500 |
| $I_1$.006 | 4 | 1 | 1 | 1 | 4 | 500 |
| $I_1$.027 | 3 | 2 | 1 | 1 | 4 | 500 |
| $I_1$.140 | 3 | 1 | 2 | 1 | 4 | 500 |
| $I_3$.027 | 6 | 1 | 1 | 2 | 6 | 500 |
| $I_5$.001 | 6 | 1 | 1 | 7 | 6 | 500 |

The same results are obtained when the compounds of the formula I are formulated in accordance with Examples F2 to F8.

EXAMPLE B2
Post-emergence Herbicidal Action

In the greenhouse, monocotyledoneous and dicotyledoneous test plants are grown in standard soil in plastic pots and, in the 4- to 6-leaf stage, sprayed with an aqueous suspension or emulsion of the test substances of the formula I, prepared from a 25% emulsion concentrate (Example F1, c)), which corresponds to a dosage of 500 g of a.i./ha (500 l of water/ha). The test plants are subsequently grown on in the greenhouse under optimal conditions. After a test period of approximately 18 days, the experiment is evaluated on a nine-step scale (1=complete damage, 9=no action). Score figures of 1 to 4 (in particular 1 to 3) denote a good to very good herbicidal action.

Test plants: Setaria, Sinapis, Solanum, Stellaria, Ipomoea.

In this test too, the compounds of the formula I show a potent herbicidal activity.

Examples of the good herbicidal activity of the compounds of formula I are given in Table B2.

TABLE B2

| | Post-emergence action: | | | | | |
|---|---|---|---|---|---|---|
| Test plant: | Setaria | Sinapis | Solanum | Stellaria | Ipomoea | Dose [g of a.i./ha] |
| Active ingredient No. | | | | | | |
| $I_1$, 001 | 3 | 4 | 2 | 5 | 1 | 500 |
| $I_1$, 006 | 2 | 3 | 1 | 3 | 1 | 500 |
| $I_1$, 027 | 3 | 3 | 1 | 1 | 1 | 500 |
| $I_1$, 122 | 4 | 1 | 1 | 1 | 1 | 500 |
| $I_1$, 130 | 3 | 1 | 1 | 1 | 1 | 500 |
| $I_1$, 134 | 5 | 3 | 1 | 1 | 1 | 500 |
| $I_1$, 140 | 2 | 4 | 1 | 1 | 1 | 500 |
| $I_1$, 151 | 3 | 1 | i | 1 | 1 | 500 |
| $I_3$, 027 | 6 | 3 | 1 | 3 | 3 | 500 |
| $I_5$, 001 | 6 | 7 | 1 | 7 | 1 | 500 |

The same results are obtained when the compounds of the formula I are formulated in accordance with Examples F2 to F8.

What is claimed is:

1. A compound of the formula I

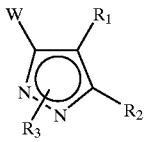

(I)

in which

R$_1$ is C$_1$–C$_4$alkyl;

R$_2$ is cyano;

R$_3$ is hydrogen, C$_1$–C$_4$alkyl, C$_1$–C$_4$haloalkyl, C$_3$- or C$_4$alkenyl, C$_3$- or C$_4$alkynyl, C$_3$–C$_8$haloalkenyl, NC—CH$_2$—, HOC(O)—CH$_2$— or C$_1$–C$_4$alkoxy-C(O)—CH$_2$—;

W is a group W$_1$

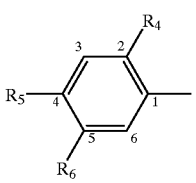

(W$_1$)

R$_4$ is fluorine, chlorine, or bromine;

R$_5$ is halogen;

R$_6$ is OR$_{20}$;

R$_{20}$ is C$_3$–C$_8$alkynyl;

or an agronomically acceptable salt or steroisomer thereof.

2. A compound according to claim 1 in which R$_1$ is methyl and R$_3$ is methyl or ethyl.

3. A compound according to claim 2 in which R$_4$ is fluorine.

4. A compound according to claim 2 in which R$_4$ is chlorine.

5. A compound according to claim 1 in which R$_5$ is chlorine or bromine.

6. A compound according to claim 1, of the formula I$_a$

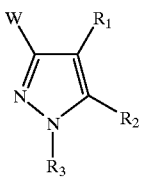

(I$_a$)

in which W and R$_1$ to R$_3$ are as defined in claim 1.

7. A compound according to claim 6 in which R$_1$ is methyl; R$_2$ is cyano; and R$_3$ is methyl or ethyl.

8. A compound according to claim 7 in which W is a group

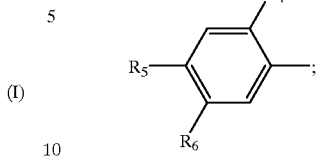

(W$_1$)

and R$_4$ is fluorine or chlorine.

9. A process for the preparation of a compound of the formula I

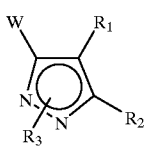

(I)

in which W, R$_1$ and R$_3$ are as defined in claim 1; and R$_2$ is cyano; which comprises a) dehydrating a compound of the formula IIa or IIb

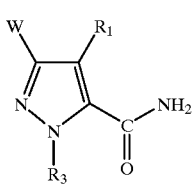

(IIa)

or

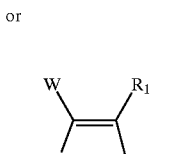

(IIb)

in which W, R$_1$ and R$_3$ are as defined above; or b) first diazotizing a compound of the formula IIIa or IIIb

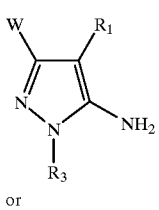

(IIIa)

or

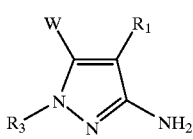

(IIIb)

in which W, $R_1$ and $R_3$ are as defined above and subsequently reacting the diazonium salt formed with a salt of the formula X $$M^+CN^- \qquad (X)$$

in which $M^+$ is an alkali metal, alkaline earth metal or transition metal ion; or c) reacting a compound of the formula IVa or IVb

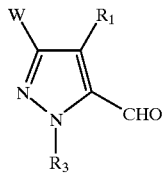

(IVa)

or

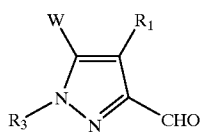

(IVb)

in which W, $R_1$ and $R_3$ are as defined above with hydroxylamine or a salt thereof and dehydrating the oxime formed as an intermediate; or d) reacting a compound of the formula Va or Vb

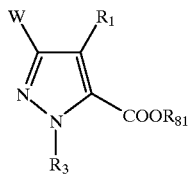

(Va)

or

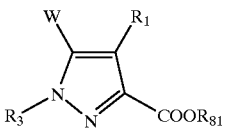

(Vb)

in which W, $R_1$ and $R_3$ are as defined in claim 1 and $R_{81}$ is $C_1$–$C_4$alkyl, $C_3$- or $C_4$alkenyl or benzyl with dimethylaluminium amide in the presence of an inert organic solvent.

10. A herbicidal and plant growth-inhibiting composition which comprises a herbicidally effective content of a compound of the formula 1 of claim 1 and an inert carrier.

11. A composition according to claim 10 which comprises between 0.1% and 95% of active ingredient of the formula I.

12. A method of controlling undesirable plant growth, which comprises applying a herbicidally effective amount of an active ingredient of the formula 1 of claim 1 or a composition comprising this active ingredient to the crops of the useful plants or their environment.

13. A method according to claim 12, which comprises applying an amount of active ingredients of between 0.001 and 4 kg per hectare.

14. A method of inhibiting plant growth, which comprises applying an effective amount of an active ingredient of the formula 1 of claim 1 or of a composition comprising this active ingredient to the plants or their environment.

15. A method according to claim 12, wherein the crops of useful plants are cereals, maize, rice, cotton, soya, oilseed rape, sorghum, sugar cane, sugar beet, sunflowers, vegetables and fodder plants.

* * * * *